United States Patent
Woodside et al.

(10) Patent No.: US 11,312,685 B2
(45) Date of Patent: Apr. 26, 2022

(54) TARGETING NANOPARTICLES

(71) Applicants: Texas Children's Hosptial, Houston, TX (US); Texas Heart Institute, Houston, TX (US)

(72) Inventors: Darren Woodside, Pearland, TX (US); Peter Vanderslice, Houston, TX (US); Robert Market, Houston, TX (US); Ronald Biediger, Houston, TX (US); Richard Dixon, Houston, TX (US); James T. Willerson, Houston, TX (US); Ananth Annapragada, Houston, TX (US); Eric Tanifum, Houston, TX (US)

(73) Assignees: Texas Heart Institute, Houston, TX (US); Texas Children's Hospital, Houston, TX (US)

( * ) Notice: Subject to any disclaimer, the term of this patent is extended or adjusted under 35 U.S.C. 154(b) by 20 days.

(21) Appl. No.: 16/607,554

(22) PCT Filed: Apr. 27, 2018

(86) PCT No.: PCT/US2018/029991
§ 371 (c)(1),
(2) Date: Oct. 23, 2019

(87) PCT Pub. No.: WO2018/201069
PCT Pub. Date: Nov. 1, 2018

(65) Prior Publication Data
US 2021/0188774 A1    Jun. 24, 2021

Related U.S. Application Data

(60) Provisional application No. 62/491,349, filed on Apr. 28, 2017.

(51) Int. Cl.
| | |
|---|---|
| C07D 213/69 | (2006.01) |
| A61K 49/00 | (2006.01) |
| A61K 49/10 | (2006.01) |
| A61K 49/18 | (2006.01) |

(52) U.S. Cl.
CPC ........ *C07D 213/69* (2013.01); *A61K 49/0002* (2013.01); *A61K 49/0084* (2013.01); *A61K 49/106* (2013.01); *A61K 49/1812* (2013.01)

(58) Field of Classification Search
CPC .. C07D 213/64; C07D 213/69; C07D 213/75; A61K 49/00
See application file for complete search history.

(56) References Cited

U.S. PATENT DOCUMENTS

| | | | |
|---|---|---|---|
| 6,224,903 | B1 | 5/2001 | Martin et al. |
| 6,972,296 | B2 | 12/2005 | Biediger et al. |
| 2003/0082103 | A1 | 5/2003 | Wartchow et al. |
| 2013/0079383 | A1 | 3/2013 | Bennett et al. |

FOREIGN PATENT DOCUMENTS

WO    2000067746 A1    11/2000

OTHER PUBLICATIONS

Wissam Beaino et al., PET Imaging of very Late Antigen-4 in Melanoma: Comparison of 68Ga- and 64Cu-Labeled NODAGA and CB-TE1A1P-LLP2A Conjugates, J Nucl Med 55, 1856-1863. (Year: 2014).*
March, J., Advanced Organic Chemistry, Localized Chemical Bonding (1985), pp. 16-18.
Woodside, Darren, et al., Magnetic Resonance Imaging of Atherosclerotic Plaque at Clinically Relevant Field Strengths, Scientific Reports (2018) 8:3733.
Koley, D., et al., Chemoselective Nitration of Phenols with tert-Butyl Nitrite in Solution and on Solid Support, Organic Letters (2009), vol. 11, No. 18, pp. 4172-4175.
List, Benjamin, et al. Practical Synthesis—Unsaturated Esters From Aldehydes, Advanced Synthesis Catalysis (2005), vol. 347, pp. 1558-1560.
Ghaghada, Ketan B., et al. New Dual Mode Gadolinium Nanoparticle Contrast Agent for Magnetic Resonance Imaging. Yang S, editor. PLoS ONE. Oct. 29, 2009;4(10):e7628.
Beaino, W., and Anderson, C.J. (2014). PET imaging of very late antigen-4 in melanoma: comparison of 68Ga- and 64Cu-labeled NODAGA and CB-TE1A1P-LLP2A conjugates. J Nucl Med 55, 1856-1863.
Beaino, W., Nedrow, J.R., and Anderson, C.J. (2015). Evaluation of (68)Ga- and (177)Lu-DOTA-PEG4-LLP2A for VLA-4-Targeted PET Imaging and Treatment of Metastatic Melanoma. Mol Pharm 12, 1929-1938.
Carpenter, R.D., Andrei, M., Lau, E.Y., Lightstone, F.C., Liu, R., Lam, K.S., and Kurth, M.J. (2007). Highly potent, water soluble benzimidazole antagonist for activated alpha 4 beta 1 integrin. J Med Chem 50, 5863-5867.
Carpenter, R.D., Natarajan, A., Lau, E.Y., Andrei, M., Solano, D.M., Lightstone, F.C., Denardo, S.J., Lam, K.S., and Kurth, M.J. (2010). Halogenated benzimidazole carboxamides target integrin alpha4beta1 on T-cell and B-cell lymphomas. Cancer Res 70, 5448-5456.
Denardo, S.J., Liu, R., Albrecht, H., Natarajan, A., Sutcliffe, J.L., Anderson, C., Peng, L., Ferdani, R., Cherry, S.R., and Lam, K.S. (2009). 111In-LLP2A-DOTA Polyethylene Glycol-Targeting {alpha}4{beta}1 Integrin: Comparative Pharmacokinetics for Imaging and Therapy of Lymphoid Malignancies. J Nucl Med 50, 625-634.

(Continued)

*Primary Examiner* — Michael G. Hartley
*Assistant Examiner* — Jagadishwar R Samala
(74) *Attorney, Agent, or Firm* — Jonathan Pierce; Pierre Campanac; Porter Hedges LLP

(57) ABSTRACT

Disclosed herein is a composition comprising a plurality of liposomes having an average diameter of less than 400 nanometers, wherein the plurality of liposomes comprise: a first lipid or phospholipid; a second lipid or phospholipid which is derivatized with a polymer; and a sterically bulky excipient capable of stabilizing the liposomes; a third lipid or phospholipid derivatized with a polymer terminated with an integrin targeting component; DSPE or a fourth lipid or phospholipid derivatized with a group binding a contrast enhancing agent wherein the plurality of liposomes optionally encapsulates a payload component consisting of one or more bioactive agents.

56 Claims, 13 Drawing Sheets

(56) References Cited

OTHER PUBLICATIONS

Jiang, M., Ferdani, R., Shokeen, M., and Anderson, C.J. (2013). Comparison of two cross-bridged macrocyclic chelators for the evaluation of 64Cu-labeled-LLP2A, a peptidomimetic ligand targeting VLA-4-positive tumors. Nucl Med Biol 40, 245-251.

Peng, L., Liu, R., Andrei, M., Xiao, W., and Lam, K.S. (2008). In vivo optical imaging of human lymphoma xenograft using a library-derived peptidomimetic against alpha4beta1 integrin. Mol Cancer Ther 7, 432-437.

Peng, L., Liu, R., Marik, J., Wang, X., Takada, Y., and Lam, K.S. (2006). Combinatorial chemistry identifies high-affinity peptidomimetics against alpha4beta1 integrin for in vivo tumor imaging. Nat Chem Biol 2, 381-389.

Shokeen, M., Zheleznyak, A., Wilson, J.M., Jiang, M., Liu, R., Ferdani, R., Lam, K.S., Schwarz, J.K., and Anderson, C.J. (2012). Molecular imaging of very late antigen-4 (alpha4beta1 integrin) in the premetastatic niche. J Nucl Med 53, 779-786.

Soodgupta, D., Hurchla, M.A., Jiang, M., Zheleznyak, A., Weilbaecher, K.N., Anderson, C.J., Tomasson, M.H., and Shokeen, M. (2013). Very late antigen-4 (alpha(4)beta(1) Integrin) targeted PET imaging of multiple myeloma. PLoS One 8, e55841.

Zwingenberger, A.L., Kent, M.S., Liu, R., Kukis, D.L., Wisner, E.R., DeNardo, S.J., Taylor, S.L., Chen, X., and Lam, K.S. (2012a). In-vivo biodistribution and safety of 99mTc-LLP2A-HYNIC in canine non-Hodgkin lymphoma. PLoS One 7, e34404.

Zwingenberger, A.L., Kent, M.S., Shi, C., Taylor, S.L., Chen, X., and Lam, K.S. (2012b). Affinity of the alpha4-beta1 integrin-targeting peptide LLP2A to canine lymphoma. Vet Immunol Immunopathol 145, 298-304.

International Search Report and Written Opinion dated Sep. 18, 2018 for PCT/US2018/029991, 12 pages.

Jung et al. "Gd (III)-DOTA-modified sonosensitive liposomes for ultrasound-triggered release and MR imaging" Nanoscale Research Letters, Aug. 17, 2012, vol. 7, 10 pages.

\* cited by examiner

Figure 2A THI565

Figure 2B THI567

THIO565

TARGETING NANOPARTICLES

CROSS-REFERENCE TO RELATED APPLICATIONS

This application is a National Stage Entry of International Application serial number PCT/US2018/029991, filed on Apr. 27, 2018. International Application serial number PCT/US2018/029991 claims priority to provisional application Ser. No. 62/491,349, filed on Apr. 28, 2017. All priority applications are included herein by reference.

STATEMENT REGARDING FEDERALLY SPONSORED RESEARCH OR DEVELOPMENT

Not Applicable.

BACKGROUND

Field of the Invention

This invention relates generally to the field of nanotechnology in medical applications. Specifically, the invention relates to targeting nanoparticles for the diagnosis and treatment of pathologies.

Background of the Invention

Monitoring of and delivering payloads to activated immune cells is a critically important process in the diagnosis and treatment of several pathologies. For example, in atherosclerotic plaques, it is known that a high prevalence of activated macrophages correlates with plaque maturity and potential for vulnerability. Imaging nanoparticles targeted to these macrophages is recognized as a method to identify the plaques. Imaging other immune cells in the plaques would greatly enhance sensitivity and potentially specificity of the method.

It is accepted that tumors divert the function of tumor associated immune cells to enable tumor cell escape. A key goal in the field of cancer immunotherapy is the ability to monitor intratumoral immune cell prevalence, as a gauge of therapeutic efficacy.

There is continuing need to develop effective targeting methods and systems for improved diagnosis and treatment of various diseases.

SUMMARY

Herein described is a compound or an integrin targeting agent, including optical isomers and pharmaceutically acceptable salts thereof, of the formula:

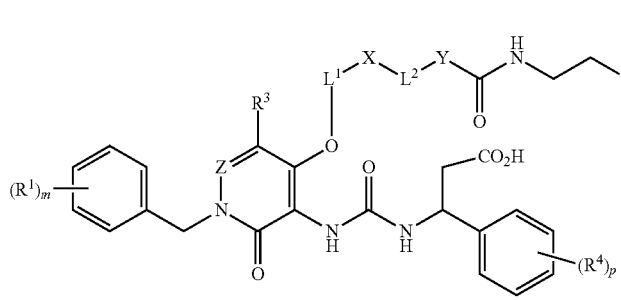

wherein, $R^1$, at each occurrence, is independently selected horn the group consisting of halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), —N($C_1$-$C_3$ alkyl)$SO_2$($C_1$-$C_3$ alkyl), —N($C_1$-$C_3$ alkyl)$SO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl, $OCF_2$, $OCH_2CF_3$, aliphatic acyl, O(cycloalkylalkyl), O(aralkyl), —$SO_2$(1-pyrolidinyl), $SO_2$(1-piperidinyl), piperidinyl, pyrrolidinyl, and —C(O)NH(benzyl) groups; Z is N or $CR^2$; $R^2$, when present, and $R^3$ are each independently selected from the group consisting of hydrogen, halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl), —C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkyl alkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$($C_1$-$C_3$ alkyl), sulfonamido, carbamate, aryloxyalkyl and —C(O)NH(benzyl) groups; and wherein $R^2$, when present, and $R^1$ may be taken together to form a ring; $R^4$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, hydroxyalkoxy, alkylamino, alkenylamino, di($C_1$-$C_3$ alkyl)amino, —C(O)O—($C_1$-$C_3$)alkyl, —C(O)NH—($C_1$-$C_3$ alkyl), —C(O)N($C_1$-$C_3$ alkyl)$_2$, —CH—NOH, —$PO_3H_2$, —$OP_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—(C$_1$-C$_3$ alkyl), —SO$_3$—(C$_1$-C$_3$ alkyl), sulfonamido, carbamate, aryloxyalkyl, O(haloalkyl), O(cycloalkyl), O(cycloalkylalkyl), piperidinyl, pyrrolidinyl and —C(O)NH(benzyl) groups; R$^1$, R$^2$, R$^3$ and R$^4$ are independently unsubstituted or substituted with at least one electron donating or electron withdrawing group; R$^5$ at each occurrence, is independently selected from a C$_7$-C$_{21}$ chain consisting of alkyl or alkenyl group; m and p are independently at each occurrence an integer from 0 to 5; L$^1$ is a chain of 3-14 atoms, containing any combination of —CH$_2$—, —C(O)—, —NH—, —S—, —S(O)—, —O, —C(O)O— or —S(O)$_2$—; X is selected from a group consisting of:

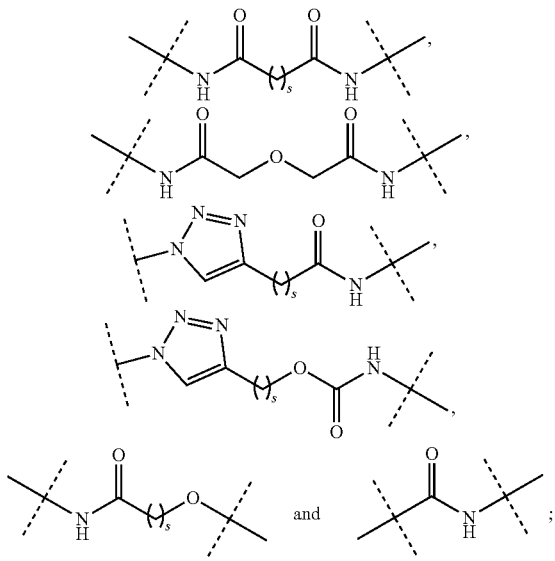

s is an integer from 1-2; L$^2$ is a —(CH$_2$CH$_2$O)$_n$— chain where n is an integer in the range of 7-115; and Y is (CH$_2$)$_q$ where q is an integer from D to 2; wherein said compound has an average molecular weight of from 2000 to 7000.

In an embodiment, the compound has the formula:

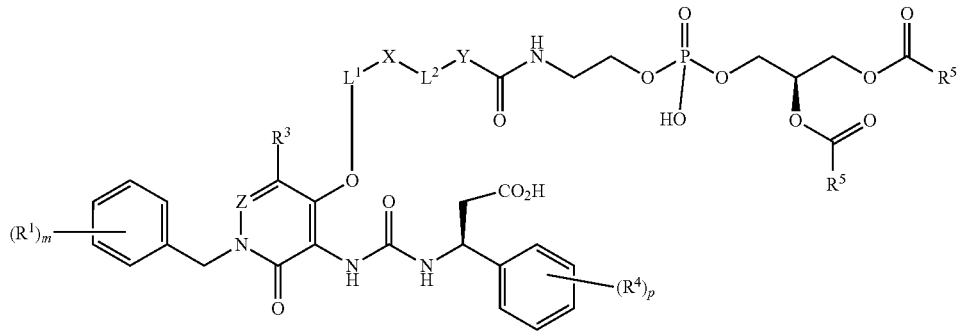

wherein, R$^1$, at each occurrence, is independently selected from the group consisting of halogen, lower alkyl, alkoxy, thioalkoxy, hydroxyalkyl, —CF$_3$, —CN, —NO$_2$, —NH$_2$, —OH, —NHSO$_2$(C$_1$-C$_3$ alkyl), alkoxyalkyl, alkylamino, cycloalkyl, aralkyl, —SO$_2$(alkyl), —OCF$_2$, aliphatic acyl, —OCH$_2$CF$_3$, alkoxyalkoxy, —O(cycloalkylalkyl), —O(aralkyl), —SO$_2$(1-pyrrolidinyl), —SO$_2$(1-piperidinyl) piperidinyl, and pyrrolidinyl groups and wherein each R$^1$ is independently unsubstituted or substituted with at least one electron donating or electron withdrawing group; Z is N or CR$^2$; R$^2$, when present, and R$^3$ are each independently selected from the group consisting of hydrogen, halogen, and lower alkyl, groups; and wherein R$^2$, when present, and R$^3$ may be taken together to form a ring and wherein each R$^2$, when present, and R$^3$ are independently unsubstituted or substituted with at least one electron donating or electron withdrawing group; R$^4$, at each occurrence, is independently selected from the group consisting of halogen, lower alkyl, alkoxy, thioalkoxy, hydroxyalkyl, hydroxyalkoxy, —CF$_3$, —NH$_2$, —OH, —NHSO$_2$(C$_1$-C$_3$ alkyl), —NHSO$_2$(aryl), alkoxyalkyl, alkylamino, di(C$_1$-C$_3$ alkyl)amino, —C(O)O—(C$_1$-C$_3$)alkyl, —C(O)NH—(C$_1$-C$_3$ alkyl), —C(O)N(C$_1$-C$_3$ alkyl)$_2$, haloalkyl, alkoxyalkoxy, cycloalkyl, aryl, sulfonamido, O(haloalkyl), O(cycloalkyl), O(cycloalkylalkyl), piperidinyl, and pyrrolidinyl groups, wherein each R$^4$ is independently unsubstituted or substituted with at least one electron donating or electron withdrawing group; R$^5$ at each occurrence, is independently selected from a C$_7$-C$_{21}$ chain consisting of alkyl or alkenyl group; m and p are independently at each occurrence an integer from 0 to 5; L$^1$ is a chain of 3-14 atoms, containing any combination of —CH$_2$—, —C(O)—, —NH—, —S—, —S(O)—, —O—, —C(O)O— or —S(O)$_2$—; X is selected from a group consisting of:

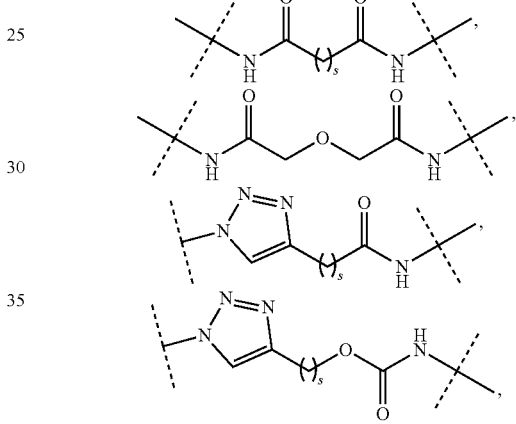

-continued

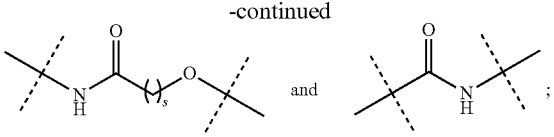

s is an integer from 1-2; L$^2$ is a —(CH$_2$CH$_2$O)$_n$— chain where n is an integer in the range of 38 to 115; and Y is (CH$_2$)$_q$ where q is an integer from 0 to 2. In an embodiment, each R$^5$ is (CH$_2$)$_r$CH$_3$ wherein r is 10-20.

In an embodiment, the compound has the formula:

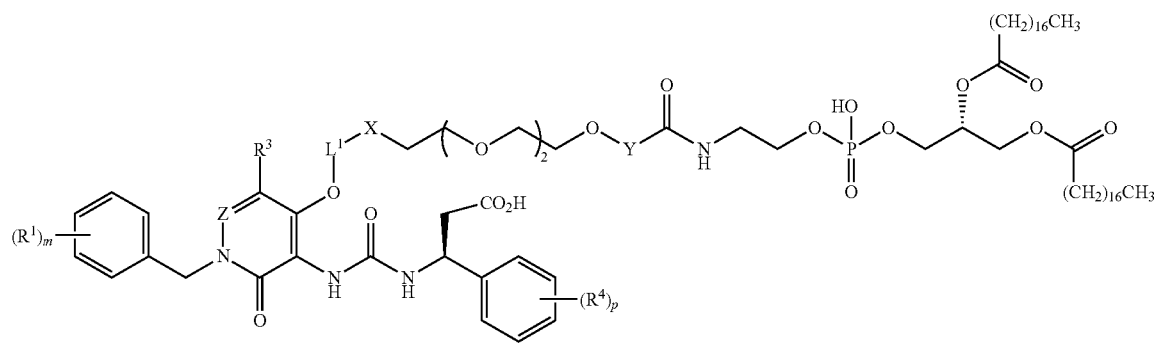

wherein n is an integer in the range of 38 to 115.

In an embodiment, $L^1$ is a 1,8-(3,6-dioxa)octan-di-yl radical, 1,5-(3-oxa)pentan-di-yl radical, or $C_3$-$C_{12}$ alkan-di-yl radical.

In an embodiment, the compound has the formula:

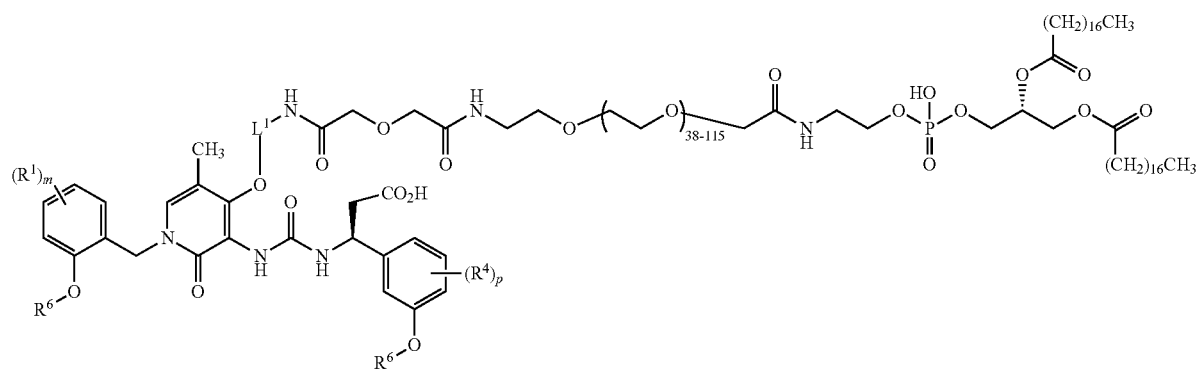

wherein each $R_6$ is independently selected from the group consisting of hydrogen, lower alkyl and hydroxyalkyl; wherein m and p are each independently an integer from 0-4.

In an embodiment, the compound has a structure as follows:

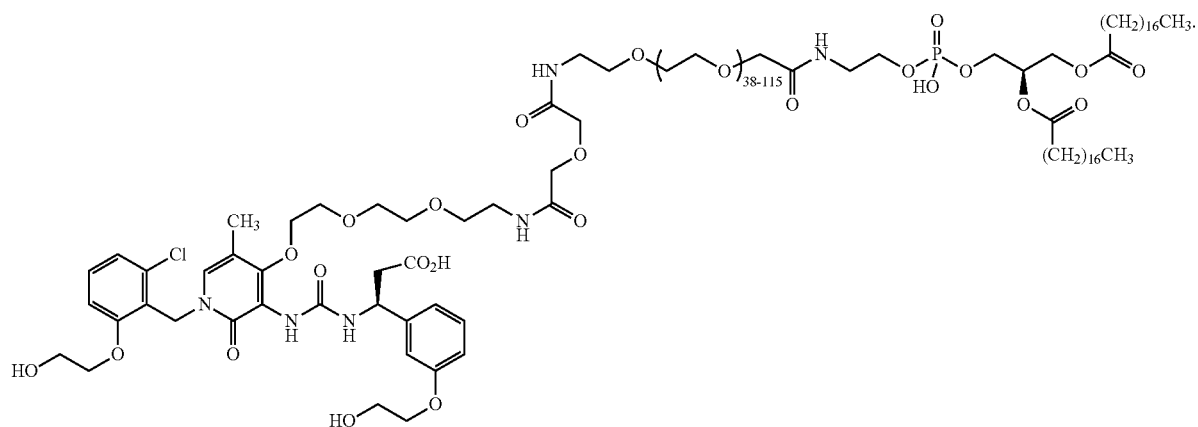

In an embodiment, the compound has a structure as follows:

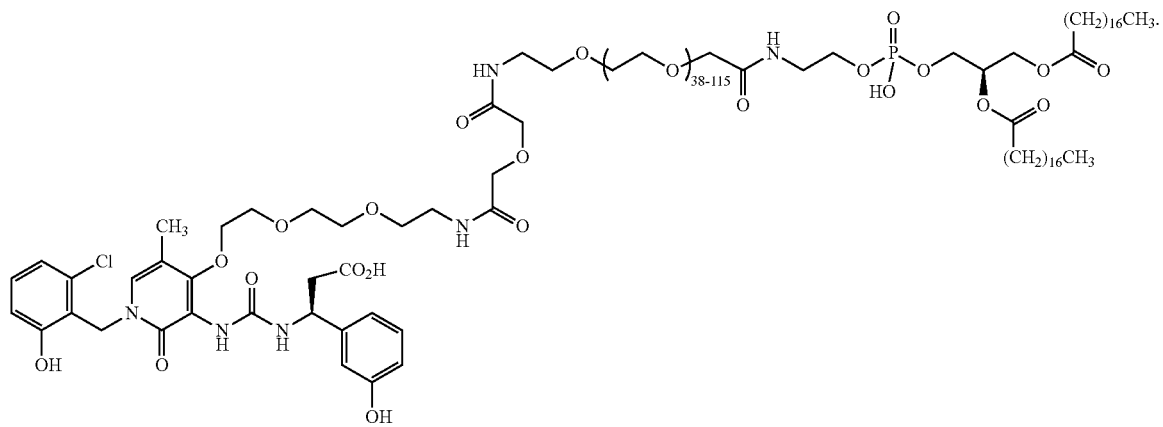

In an embodiment, the compound has the formula:

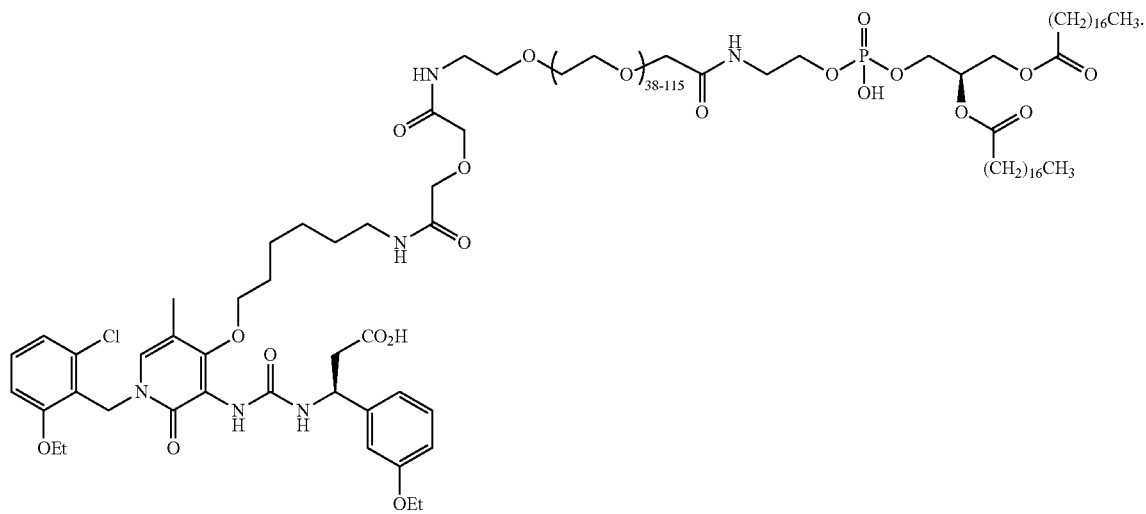

In an embodiment, the compound of this disclosure enables the generation of MRI images. In cases, these MRI images are generated at clinically relevant field strength, e.g., 1 Tesla Held strength.

Also disclosed herein is a composition comprising a plurality of liposomes having an average diameter of less than 400 nanometers, wherein the plurality of liposomes comprise: a first lipid or phospholipid; a second lipid or phospholipid which is derivatized with a polymer; a sterically bulky excipient capable of stabilizing the liposomes; a third lipid or phospholipid derivatized with a polymer terminated with an integrin targeting component; and optionally DSPE or a fourth lipid or phospholipid derivatized with a group binding a contrast enhancing agent wherein the plurality of liposomes optionally encapsulates a payload component consisting of one or more bioactive agents. In an embodiment (e.g., the doxorubicin formulation), wherein the fourth lipid or phospholipid is not present, the balance is DPPC, which is the same as the first lipid or phospholipid. As used herein, a contrast enhancing agent is one that allows for obtaining or generating images or enhancing the quality of an image obtained in a clinical setting.

In an embodiment, a composition comprises a plurality of liposomes, said liposomes comprising: a first lipid or phospholipid; a second lipid or phospholipid which is derivatized with a polymer, a stoically bulky excipient capable of stabilizing the liposomes; a third lipid or phospholipid derivatized with a polymer terminated with an integrin targeting component; and DSPE or a fourth lipid or phospholipid derivatized with a group binding a contrast enhancing agent, wherein the plurality of liposomes optionally encapsulates a payload component consisting of one or more bioactive agents, rhodamine, DHPE or iodine contrast agent; wherein the plurality of liposomes have an average diameter of less than 400 nanometers.

In an embodiment, the first lipid or phospholipid comprises DPPC or HSPC. HSPC represents hydrogenated soybean phosphatidylcholine. In an embodiment, the second lipid or phospholipid which is derivatized with a polymer comprises mPEG (2000)-DSPE. In an embodiment, the third lipid or phospholipid derivatized with a polymer terminated with an integrin targeting component is a compound as discussed herein.

In an embodiment, the optional fourth lipid or phospholipid derivatized with a group binding a nonradioactive contrast enhancing agent is bis stearylamine-DTPA-Gd. In an embodiment, the optional fourth lipid or phospholipid derivatized with a group binding a nonradioactive contrast enhancing agent is Gd-DOTA-DSPE. DOTA represents 1,4,7,10-Tetraazacyclododecane-1,4,7,10-tetraacetic acid. DSPE represents 1,2-Distearoyl-sn-glycero-3-phosphoethanolamine. In an embodiment, the first lipid or phospholipid, the second lipid or phospholipid which is derivatized with a polymer, and the sterically bulky excipient capable of stabilizing the liposomes, and the fourth lipid or phospholipid derivatized with a group binding a nonradioactive contrast enhancing agent are present in a molar ratio of about 30-32:3:40:25.

In an embodiment, the lipid or phospholipid derivatized with a polymer terminated with an integrin targeting component consists of 0.05 to 2.0% (mole percent) the compound as discussed herein. In an embodiment, the optional fourth lipid capable of binding a non-radioactive gadolinium salt is replaced with 1,2-distearoyl-sn-glycero-3-phosphoethanolamine (DSPE). In an embodiment, the bio-active agent is selected from a group comprising: doxorubicin, paclitaxel, daunorubicin, vincristine, tretinoin, cisplatin, annamycin, vinorelbine, irinotecan HCl, or floxuridine. In an embodiment, the liposomes have an average diameter of about 150 nm. In an embodiment, the liposomes have an average diameter of less than 250 nm. In an embodiment, the bio-active agent comprises at least one selected from the group consisting of a chemotherapeutic, a gene, a protein, a small molecule, and a peptide.

In an embodiment, the composition is capable of being detected using at least one selected from the group consisting of CT, micro-CT, mammography, X-ray, MRI, magnetic resonance spectroscopy, bioluminescence imaging, ultrasound, optical imaging, optical spectroscopy, fluorescence spectroscopy, fluorescence imaging, near-infrared spectroscopy, and near-infrared imaging. In various embodiments, the composition is used in an imaging modality or used for drug delivery. In an embodiment, the composition of this disclosure enables generation of MRI images. In an embodiment, the composition of this disclosure enables generation of MRI images at clinically relevant field strength, e.g., 1 Tesla field strength.

Herein also disclosed is a method of producing a liposome comprising combining a first lipid or phospholipid with a second lipid or phospholipid derivatized with a polymer, a sterically bulky excipient to stabilize the liposome, a third lipid or phospholipid derivatized with a polymer terminated with an integrin targeting component, and DSPE or a fourth lipid or phospholipid capable of binding a non-radioactive contrasting agent, and extruding to form particles of less than 400 nm.

In an embodiment, the liposome comprises a contrast enhancing agent. In an embodiment the liposome encapsulates a payload component consisting of one or more bioactive agents.

In an embodiment, the integrin targeting component has a molecular weight of from 2000 to 7000, includes optical isomers and pharmaceutically acceptable salts thereof, and is of the formula:

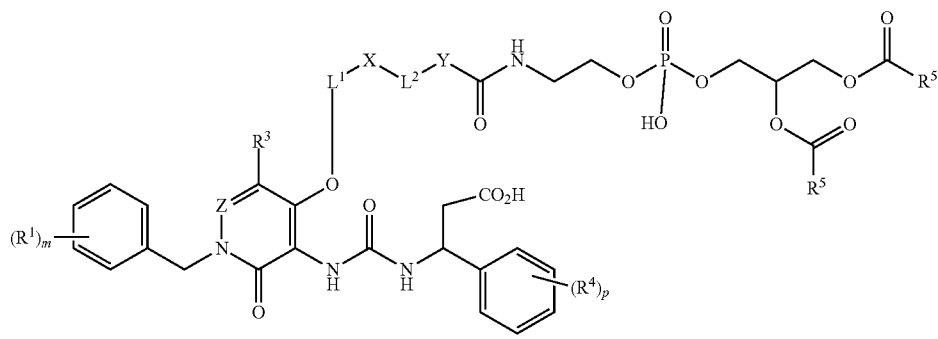

wherein $R^1$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_5$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), —N($C_1$-$C_3$ alkyl)$SO_2$($C_1$-$C_3$ alkyl), —N($C_1$-$C_3$ alkyl)$SO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryi, diarylamino, heterocyclyl, alkylaryl, aralkenyl, aralkyl, alkylheterocyclyl, heterocyclylalkyl, sulfonyl, —$SO_2$—($C_1$-$C_3$ alkyl), alkyl), sulfonamido, carbamate, aryloxyalkyl, $OCF_2$, $OCH_2CF_3$, aliphatic acyl, O(cycloalkylalkyl), O(aralkyl), —$SO_2$(1-pyrolidinyl), $SO_2$(1-piperidinyl), piperidinyl, pyrrolidinyl, and —C(O)NH(benzyl) groups; Z is N or $CR^2$; $R^2$, when present, and $R^3$ are each independently selected from the group consisting of hydrogen, halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl), —C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryi, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$($C_1$-$C_3$ alkyl), sulfonamido, carbamate, aryloxyalkyl and —C(O)NH(benzyl) groups; and wherein $R^2$, when present, and $R^3$ may be taken together to form a ring; $R^4$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N(C$_1$-C$_3$ alkyl)-C(O)(C$_1$-C$_3$ alkyl), —NHC(O)N(C$_1$-C$_3$ alkyl)C(O)NH(C$_1$-C$_3$ alkyl), —NHC(O)NH(C$_1$-C$_6$ alkyl), —NHSO$_2$(C1-C$_3$ alkyl), —NHSO$_2$(aryl), alkoxyalkyl, alkylamino, alkenylamino, di(C$_1$-C$_3$ alkyl)amino, —C(O)O—(C$_1$-C$_3$)alkyl, —C(O)NH—(C$_1$-C$_3$ alkyl), —C(O)N(C$_1$-C$_3$ alkyl)$_2$, —CH—NOH, —PO$_3$H$_2$, —OPO$_3$H$_2$, haloalkyl, alkoxyalkoxy, hydroxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—(C$_1$-C$_3$ alkyl), —SO$_3$—(C$_1$-C$_3$ alkyl), sulfonamido, carbamate, aryloxyalkyl, O(haloalkyl), O(cycloalkyl), O(cycloalkylalkyl), piperidinyl, pyrrolidinyl and —C(O)NH(benzyl) groups; R$^1$, R$^2$, R$^3$ and R$^4$ are independently unsubstituted or substituted with at least one electron donating or electron withdrawing group; R$^5$ at each occurrence, is independently selected from a C$_7$-C$_{21}$ chain consisting of alkyl or alkenyl group; m and p are independently at each occurrence an integer from 0 to 5; L$^1$ is a chain of 3-14 atoms, containing any combination of —CH$_2$—, —C(O)—, —NH—, —S—, —S(O)—, —O—, —C(O)O— or —S(O)$_2$—;

X is selected from a group consisting of:

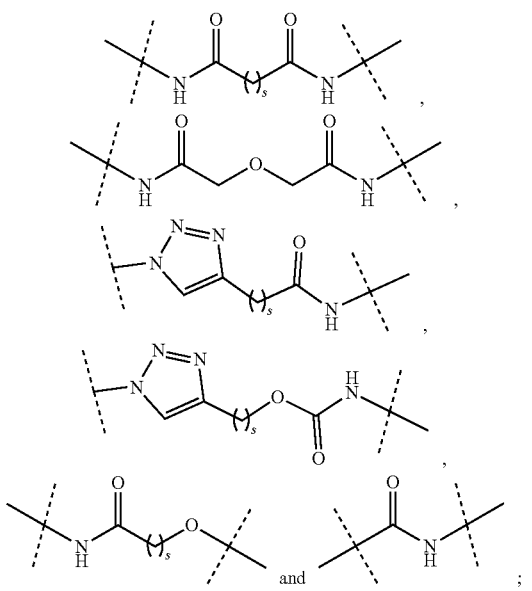

and ;

s is an integer from 1-2; L$^2$ is a —(CH$_2$CH$_2$O)$_n$— chain where n is an integer in the range of 38 to 115 and Y is (CH$_2$)$_q$ where q is an integer from 0 to 2.

In an embodiment, the integrin targeting component is of the formula:

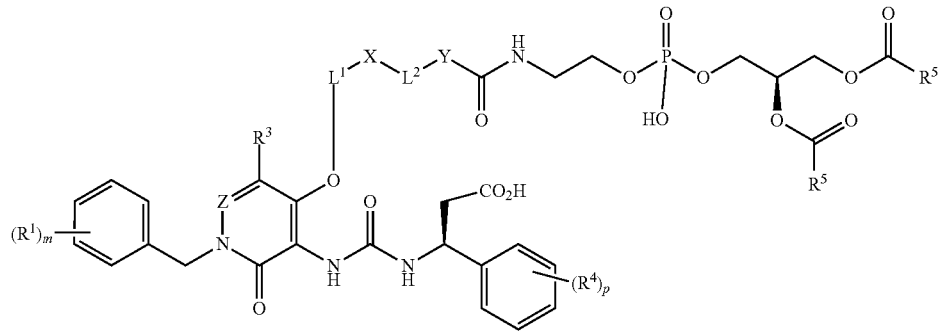

wherein R$^1$, at each occurrence, is independently selected from the group consisting of halogen, lower alkyl, alkoxy, thioalkoxy, hydroxyalkyl, —CF$_3$, —CN, —NO$_2$, —NH$_2$, —OH, —NHSO$_2$(C$_1$-C$_3$ alkyl), alkoxyalkyl, alkylamino, cycloalkyl, aralkyl, —SO$_2$(alkyl), —OCF$_2$, aliphatic acyl, —OCH$_2$CF$_3$, alkoxyalkoxy, —O(cycloalkylalkyl), —O(aralkyl), —SO$_2$(1-pyrrolidinyl), —SO$_2$(1-piperidinyl) piperidinyl, and pyrrolidinyl groups and wherein each R$^1$ is independently unsubstituted or substituted with at least one electron donating or electron withdrawing group; Z is N or CR$^2$; R$^2$, when present, and R$^3$ are each independently selected from the group consisting of hydrogen, halogen, and lower alkyl, groups; and wherein R$^2$, when present, and R$^3$ may be taken together to form a ring and wherein each R$^2$, when present, and R$^3$ are independently unsubstituted or substituted with at least one electron donating or electron withdrawing group; R$^4$, at each occurrence, is independently selected from the group consisting of halogen, lower alkyl, alkoxy, thioalkoxy, hydroxyalkyl, hydroxyalkoxy, —CF$_3$, —NH$_2$, —OH, —NHSO$_2$(C1-C$_3$ alkyl), —NHSO$_2$(aryl), alkoxyalkyl, alkylamino, di(C$_1$-C$_3$ alkyl)amino, —C(O)O—(C$_1$-C$_3$)alkyl, —C(O)NH—(C$_1$-C$_3$ alkyl), —C(O)N(C$_1$-C$_3$ alkyl)$_2$, haloalkyl, alkoxyalkoxy, cycloalkyl, aryl, sulfonamido, O(haloalkyl), O(cycloalkyl), O(cycloalkylalkyl), piperidinyl, and pyrrolidinyl groups, wherein each R$^4$ is independently unsubstituted or substituted with at least one electron donating or electron withdrawing group; R$^5$ at each occurrence, is independently selected from a C$_7$-C$_{21}$ chain consisting of alkyl or alkenyl group; m and p are independently at each occurrence an integer from 0 to 5; L$^1$ is a chain of 3-14 atoms, containing any combination of —CH$_2$—, —C(O)—, —NH—, —S—, —S(O)—, —O—, —C(O)O— or —S(O)$_2$;

X is selected from a group consisting of:

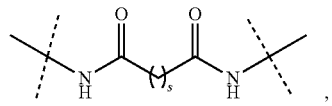

-continued

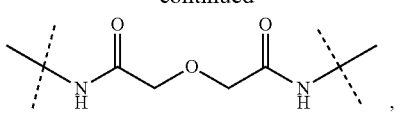

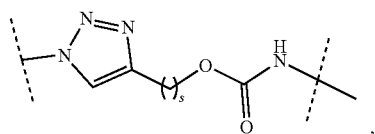

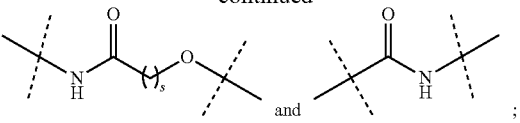

s is an integer from 1-2; $L^2$ is a —$(CH_2CH_2O)_n$— chain where n is an integer in the range of 38 to 115; and Y is $(CH_2)_q$ where q is an integer from 0 to 2.

In an embodiment, each $R^5$ is $(CH_2)_rCH_3$ wherein r is 10-20.

In an embodiment, the interim targeting component is of the formula:

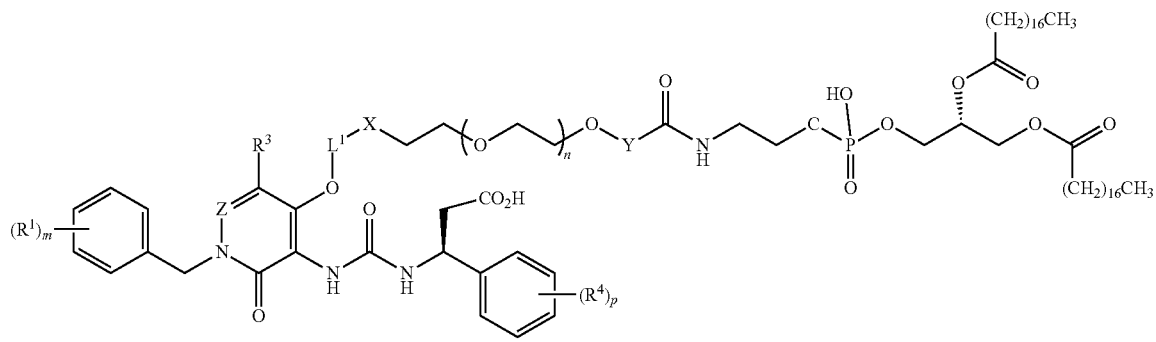

wherein n is an integer in the range of 38 to 115.

In an embodiment, $L^1$ is a 1,8-(3,6-dioxa)octan-di-yl radical, 1,5-(3-oxa)pentan-di-yl radical, or $C_3$-$C_{12}$ alkan-di-yl radical.

In an embodiment, the integrin targeting component is of the formula:

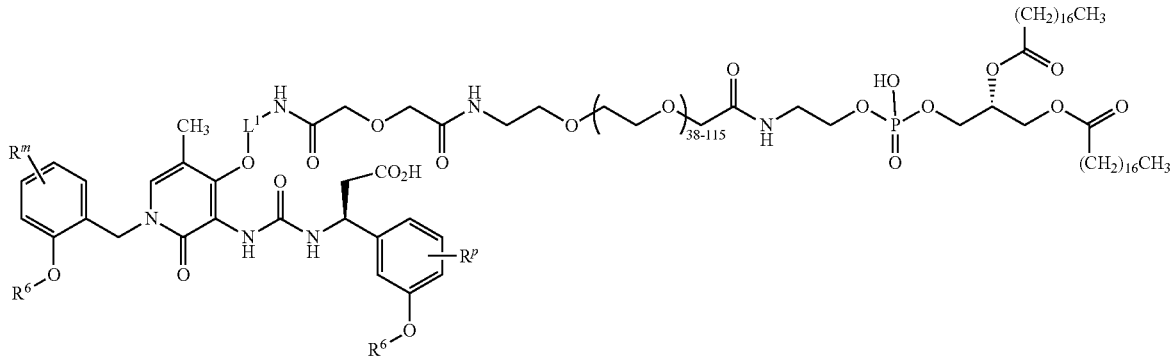

wherein each $R^6$ is independently selected from the group consisting of hydrogen, lower alkyl and hydroxyalkyl.

In an embodiment, the integrin targeting component has a structure as follows:
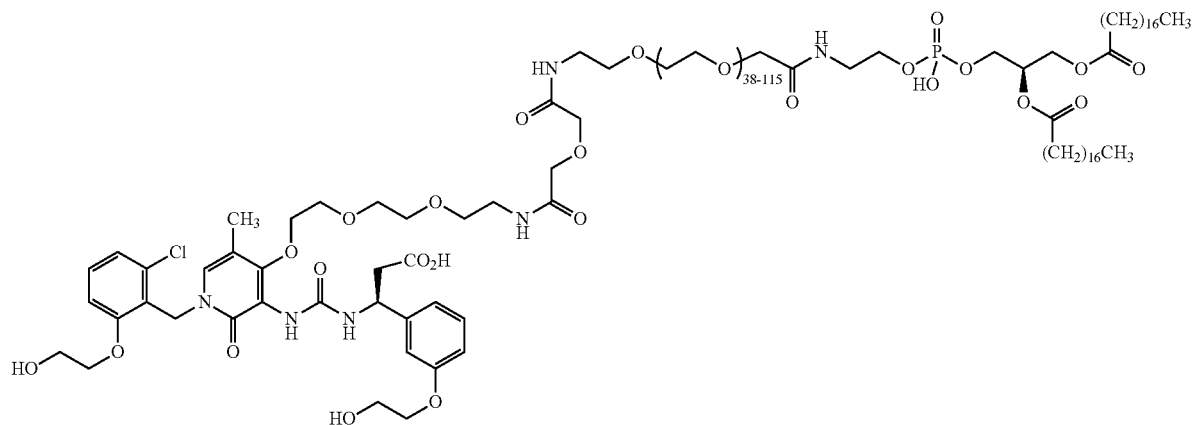
In an embodiment, the integrin targeting component has a structure as follows:
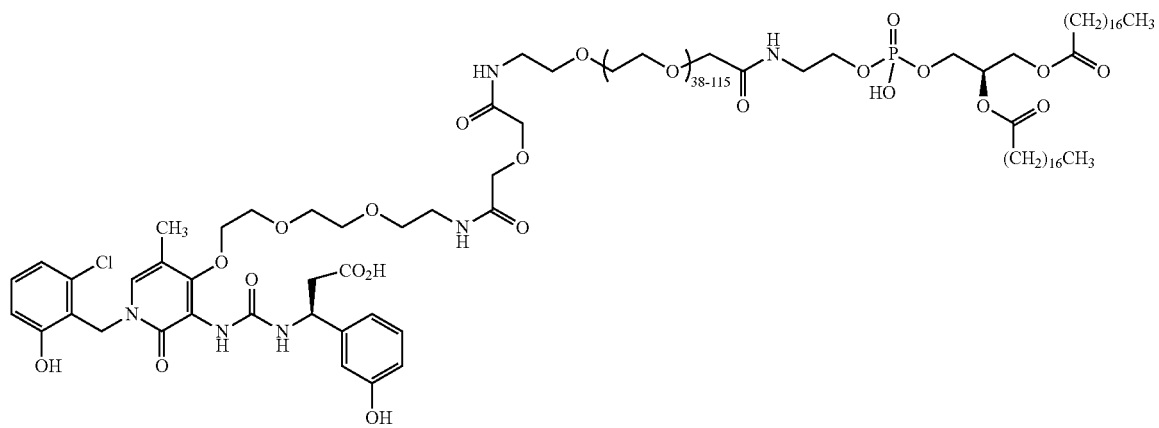
In an embodiment, the integrin targeting component is of the formula:
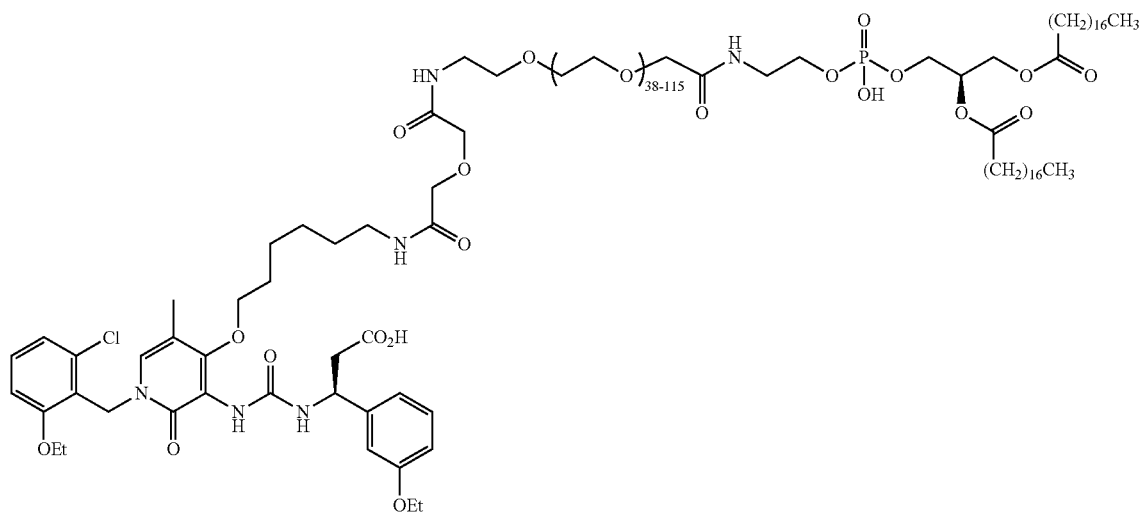

In an embodiment, the liposome enable generation of MRI images. In an embodiment, the liposome enable generation of MRI images at clinically relevant strength, e.g., 1 Tesla field strength.

Further disclosed is a method of producing an integrin targeting agent comprising forming a functionally protected VLA-4 antagonist of the structure, including optical isomers:

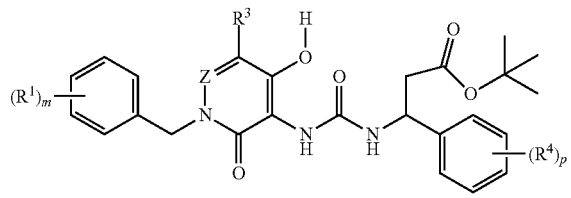

wherein, $R^1$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), —N($C_1$-$C_3$ alkyl)$SO_2$($C_1$-$C_3$ alkyl), —N($C_1$-$C_3$ alkyl)$SO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl, $OCF_2$, $OCH_2CF_3$, aliphatic acyl, O(cycloalkylalkyl), O(aralkyl), —$SO_2$(1-pyrolidinyl), $SO_2$(1-piperidinyl), piperidinyl, pyrrolidinyl, and —C(O)NH(benzyl) groups; Z is N or $CR^2$; $R^2$, when present, and $R^3$ are each independently selected from the group consisting of hydrogen, halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, alkyl)-C(O)($C_1$-$C_3$ alkyl), —NHC(O)N($C_1$-$C_3$ alkyl), —C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$)amino, —C(O)O—($C_1$-$C_3$) alkyl, —C(O)NH—($C_1$-$C_3$)alkyl, —C(O)N($C_1$-$C_3$ alkyl)$_2$, —CH=NOH, —$PO_3H_2$, —$OPO_3H_2$ haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylhelerocyclyl, heterocyclylalkyl, sulfonyl, —$SO_2$—($C_1$-$C_3$ alkyl), —$SO_3$($C_1$-$C_3$ alkyl), sulfonamido, carbamate, aryloxyalkyl and —C(O)NH(benzyl) groups; and wherein $R^2$, when present, and $R^3$ may be taken together to form a ring; $R^4$, at each occurrence, is independently selected horn the group consisting of halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$ alkyl)amino, —C(O)O—($C_1$-$C_3$)alkyl, —C(O)NH—($C_1$-$C_3$ alkyl), —C(O)N($C_1$-$C_3$ alkyl)$_2$, —CH—NOH, —$PO_3H_2$, —$OPO_3H_2$, haloalkyl, alkoxyalkoxy, hydroxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl, O(haloalkyl), O(cycloalkyl), O(cycloalkylalkyl), piperidinyl, pyrrolidinyl and —C(O)NH(benzyl) groups; $R^1$, $R^2$, $R^3$ and $R^4$ are independently unsubstituted or substituted with at least one electron donating or electron withdrawing group; the method comprising synthesizing a phospholipid by alkylating at the pyridone hydroxyl with a functionalized 3-17 atom linking group;

optionally modifying the terminal functional group; and attaching to a polymeric group suitable for liposome formation by means of amide coupling, carbamate formation or triazole formation, and deprotection of functional groups.

In an embodiment, the integrin targeting agent has an average molecular weight of 2000-7000. In an embodiment, the integrin targeting agent enables generation of MRI images. In an embodiment, the integrin targeting agent enables generation of MRI images at clinically relevant field strength, e.g., at 1 Tesla field strength. In an embodiment, the integrin targeting agent is incorporated into a delivery vehicle for drug delivery or diagnostics.

Discussed herein is a method of drug delivery comprising forming a plurality of liposomes having an average diameter of less than 400 nanometers, said liposomes comprising: a first lipid or phospholipid; a second lipid or phospholipid which is derivatized with a polymer, a sterically bulky excipient capable of stabilizing the liposomes; a third lipid or phospholipid derivatized with a polymer terminated with an integrin targeting component having an average molecular weight of 2000-7000; optionally DSPE; encapsulating at least one bio-active agent using said plurality of liposomes; and administering said plurality of liposomes to a patient. In an embodiment, DPPC is used instead of DSPE.

In an embodiment, the bio-active agent comprises doxorubicin, paclitaxel, daunorubicin, vincristine, tretinoin, cisplatin, annamycin, vinorelbine, irinotecan HCl, or floxuridine. In an embodiment, the integrin targeting component including optical isomers and pharmaceutically acceptable salts thereof, is of the formula:

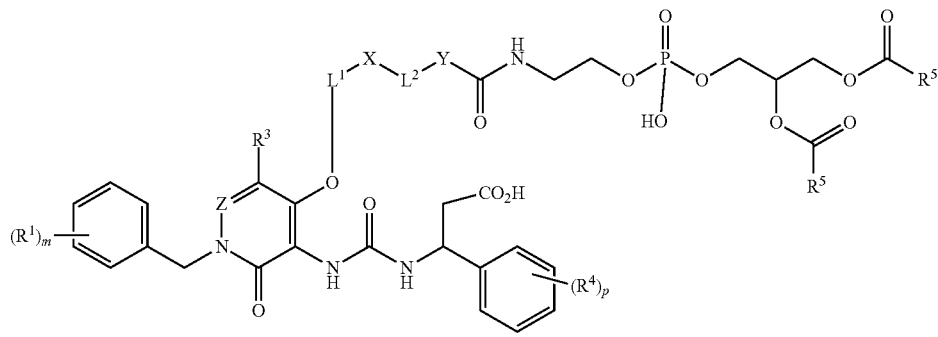

wherein, $R^1$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), —N($C_1$-$C_3$ alkyl)$SO_2$($C_1$-$C_3$ alkyl), —N($C_1$-$C_3$ alkyl)$SO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl, $OCF_2$, $OCH_2CF_3$, aliphatic acyl, O(cycloalkylalkyl), O(aralkyl), —$SO_2$(1-pyrolidinyl), $SO_2$(1-piperidinyl), piperidinyl, pyrrolidinyl, and —C(O)NH(benzyl) groups; Z is N or $CR^2$; $R^2$, when present, and $R^3$ are each independently selected from the group consisting of hydrogen, halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl), —C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$($C_1$-$C_3$ alkyl), sulfonamido, carbamate, aryloxyalkyl and —C(O)NH(benzyl) groups; and wherein $R^2$, when present, and $R^3$ may be taken together to form a ring; $R^4$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$(C1-$C_3$ alkyl), —$NHSO_2$(aryl), alkoxyalkyl, alkylamino, alkenylamino, di($C_1$-$C_3$ alkyl)amino, —C(O)O—($C_1$-$C_3$)alkyl, —C(O)NH—($C_1$-$C_3$ alkyl), —C(O)N($C_1$-$C_3$ alkyl)$_2$, —CH=NOH, —$PO_3H_2$, —$OPO_3H_2$, haloalkyl, alkoxyalkoxy, hydroxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl, O(haloalkyl), O(cycloalkyl), O(cycloalkylalkyl), piperidinyl, pyrrolidinyl and —C(O)NH(benzyl) groups; $R^1$, $R^2$, $R^3$ and $R^4$ are independently unsubstituted or substituted with at least one electron donating or electron withdrawing group; $R^5$ at each occurrence, is independently selected from a $C_7$-$C_{21}$ chain consisting of alkyl or alkenyl group; m and p are independently at each occurrence an integer from 0 to 5; $L^1$ is a chain of 3-14 atoms, containing any combination of —$CH_2$—, —C(O)—, —NH—, —S—, —S(O)—, —O—, —C(O)O— or —S(O)$_2$—;

X is selected from a group consisting of:

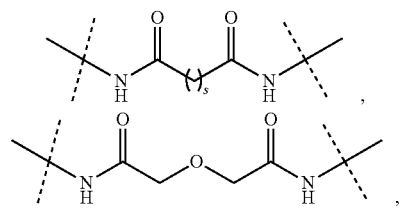

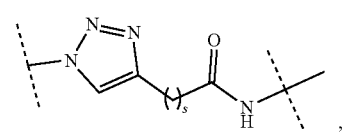

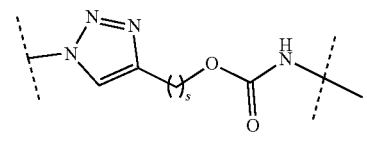

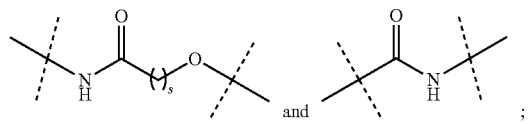

s is an integer from 1-2; $L^1$ is a —($CH_2CH_2O$)$_n$— chain where n is an integer in the range of 38 to 115; and Y is ($CH_2$)$_q$ where q is an integer from 0 to 2.

Disclosed herein is a method of imaging comprising forming a plurality of liposomes having an average diameter of less than 400 nanometers, said liposomes comprising: a first lipid or phospholipid; a second lipid or phospholipid which is derivatized with a polymer; a sterically bulky excipient capable of stabilizing the liposomes; a third lipid or phospholipid derivatized with a polymer terminated with an integrin targeting component having an average molecular weight of 2000-7000; a fourth lipid or phospholipid; incorporating a contrast enhancing agent into said plurality of liposomes; and using an imaging modality selected from the group consisting of CT, micro-CT, mammography, X-ray, MRI, magnetic resonance spectroscopy, bioluminescence imaging, ultrasound, optical imaging, optical spectroscopy, fluorescence spectroscopy, near-infrared spectroscopy, and near-infrared imaging. In an embodiment, the MRI images are generated at 1 Tesla field strength. In an embodiment, the MRI images are generated at field strength greater than 1 Tesla.

In an embodiment, the integrin targeting component including optical isomers and pharmaceutically acceptable salts thereof, is of the formula:

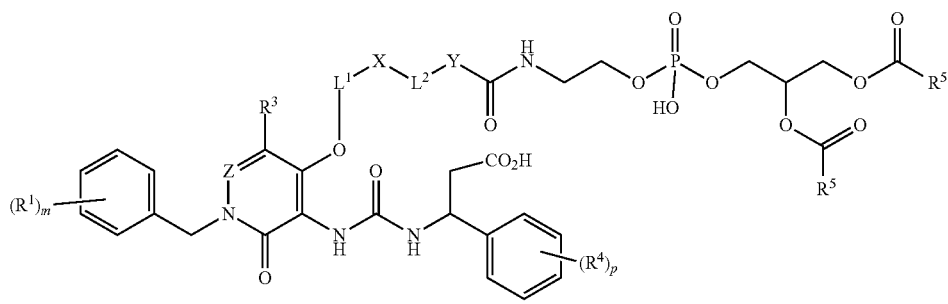

wherein, $R^1$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), —N($C_1$-$C_3$ alkyl)$SO_2$($C_1$-$C_3$ alkyl), —N($C_1$-$C_3$ alkyl)$SO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl, $OCF_2$, $OCH_2CF_3$, aliphatic acyl, O(cycloalkylalkyl), O(aralkyl), —$SO_2$(1-pyrolidinyl), $SO_2$(1-piperidinyl), piperidinyl, pyrrolidinyl, and —C(O)NH(benzyl) groups; Z is N or $CR^2$; $R^2$, when present, and $R^3$ are each independently selected from the group consisting of hydrogen, halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl), —C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$($C_1$-$C_3$ alkyl), sulfonamido, carbamate, aryloxyalkyl and —C(O)NH(benzyl) groups; and wherein $R^2$, when present, and $R^3$ may be taken together to form a ring; $R^4$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$ alkyl)amino, —C(O)O—($C_1$-$C_3$)alkyl, —C(O)NH—($C_1$-$C_3$ alkyl), —C(O)N($C_1$-$C_3$ alkyl)$_2$, —CH=NOH, —$PO_3H_2$, —$OPO_3H_2$, haloalkyl, alkoxyalkoxy, hydroxalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl, O(haloalkyl), O(cycloalkyl), O(cycloalkylalkyl), piperidinyl, pyrrolidinyl and —C(O)NH(benzyl) groups; $R^1$, $R^2$, $R^5$ and $R^4$ are independently unsubstituted or substituted with at least one electron donating or electron withdrawing group;

$R^5$ at each occurrence, is independently selected from a $C_7$-$C_{21}$ chain consisting of alkyl or alkenyl group; m and p are independently at each occurrence an integer from 0 to 5; $L^1$ is a chain of 3-14 atoms, containing any combination of —$CH_2$—, —C(O)—, —NH—, —S—, —S(O)—, —O—, —C(O)O— or —S(O)$_2$—;

X is selected from a group consisting of:

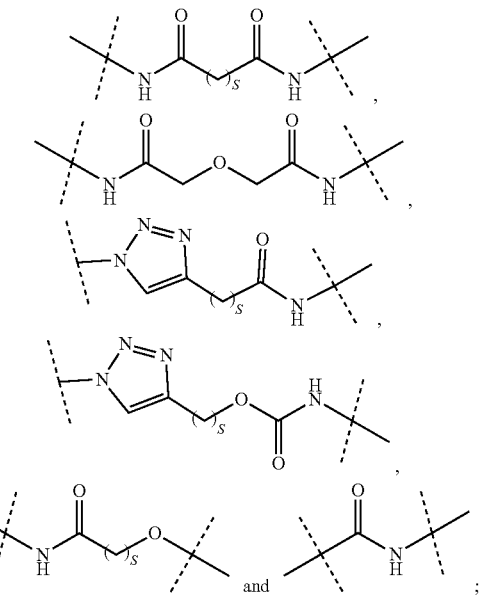

s is an integer from 1-2; $L^2$ is a —($CH_2CH_2O$)$_n$— chain where n is an integer in the range of 38 to 115; and Y is ($CH_2$)$_q$ where q is an integer from 0 to 2.

Herein disclosed is a composition comprising a plurality of liposomes, wherein the plurality of liposomes comprise an integrin-targeting molecule, wherein the integrin-targeting molecule comprises a polymer derivatized lipid or phospholipid moiety and an integrin-targeting moiety. In an embodiment, the integrin-targeting moiety has one of the following structures:

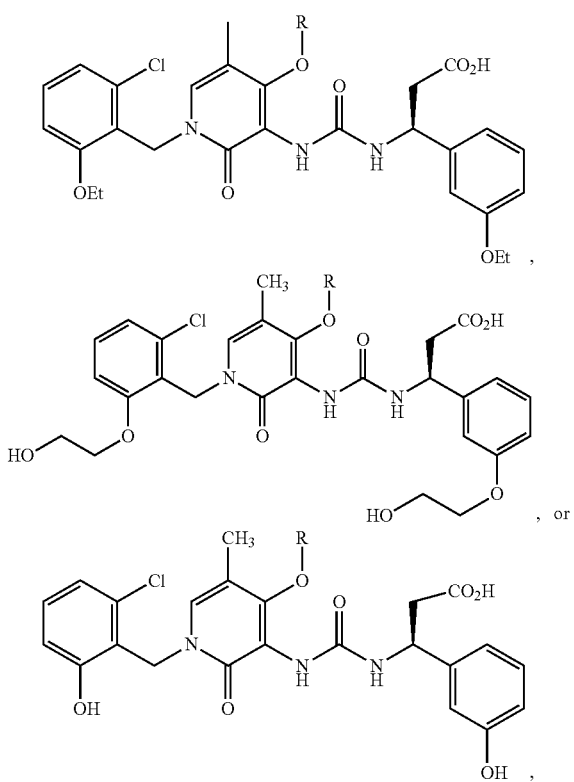

wherein R is the attachment point for the polymer derivatized lipid or phospholipid moiety. In an embodiment, the integrin-targeting molecule is a compound of this disclosure. In an embodiment, the plurality of liposomes have an average diameter of 150 to 175 nm. In an embodiment, the integrin-targeting molecule comprises about 0.05 to 2 mol % of the plurality of liposomes. In an embodiment, the plurality of liposomes further comprise a bio-active agent. In an embodiment, the bio-active agent is encapsulated within the plurality of liposomes.

In an embodiment, the plurality of liposomes further comprise a lipid or phospholipid derivatized with a group binding a contrast enhancing agent. In an embodiment, the lipid or phospholipid derivatized with a group binding a contrast enhancing agent comprises a DTPA-Gd or a DOTA-Gd moiety. In an embodiment, the liposomes comprise 30 to 45 mol % DPPC, 15 to 45 mol % cholesterol, 1 to 6 mol % DSPE-MPEG-2000, 20 to 30 mol % Gd-DOTA-DSPE, and 0.05 to 2 mol % THI-567.

Discussed herein is a method of delivering a bio-active agent to a target cell in a patient, the method comprising administering the composition of this disclosure to the patient. In an embodiment, the bio-active agent is selectively delivered to cells expressing α4β1 integrin. In an embodiment, the cells expressing α4β1 integrin comprise one or more of the following types of cells: $CD11b^+$ mononuclear cells, $CD3^+$ T cells, $CD19^+$ B cells, and $Ly-6G^+$ polymorphonuclear leukocytes.

Further disclosed herein is a method of imaging a biological structure in a subject, the method comprising administering to the subject the composition of this disclosure and detecting the contrast enhancing agent with an imager. In an embodiment, liposomes in the composition become enriched in the biological structure. In an embodiment, the imager performs one of the following techniques: CT, micro-CT, mammography, X-ray, MRI, magnetic resonance spectroscopy, bioluminescence imaging, ultrasound, optical imaging, optical spectroscopy, fluorescence spectroscopy, fluorescence imaging, near-infrared spectroscopy, and near-infrared imaging.

In an embodiment, the imager is an MRI scanner having a field strength of no more than 3T or of no more than 1T. In an embodiment, the biological structure is an atherosclerotic plaque, a plurality of cells expressing α4β1 integrin, or a tumor.

Further disclosed herein is a method of identifying a patient at risk for an acute ischemic event, the method comprising: (a) administering to the subject the composition of this disclosure; (b) detecting the contrast enhancing agent with an MRI scanner to generate an image; (c) evaluating the image for the presence of atherosclerotic plaques; and (d) identifying the patient as being at risk for an acute ischemic event if atherosclerotic plaques are detected.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which:

FIG. 3B displays percent inhibition of maximal signal.

DETAILED DESCRIPTION

Definitions

Figure 1:
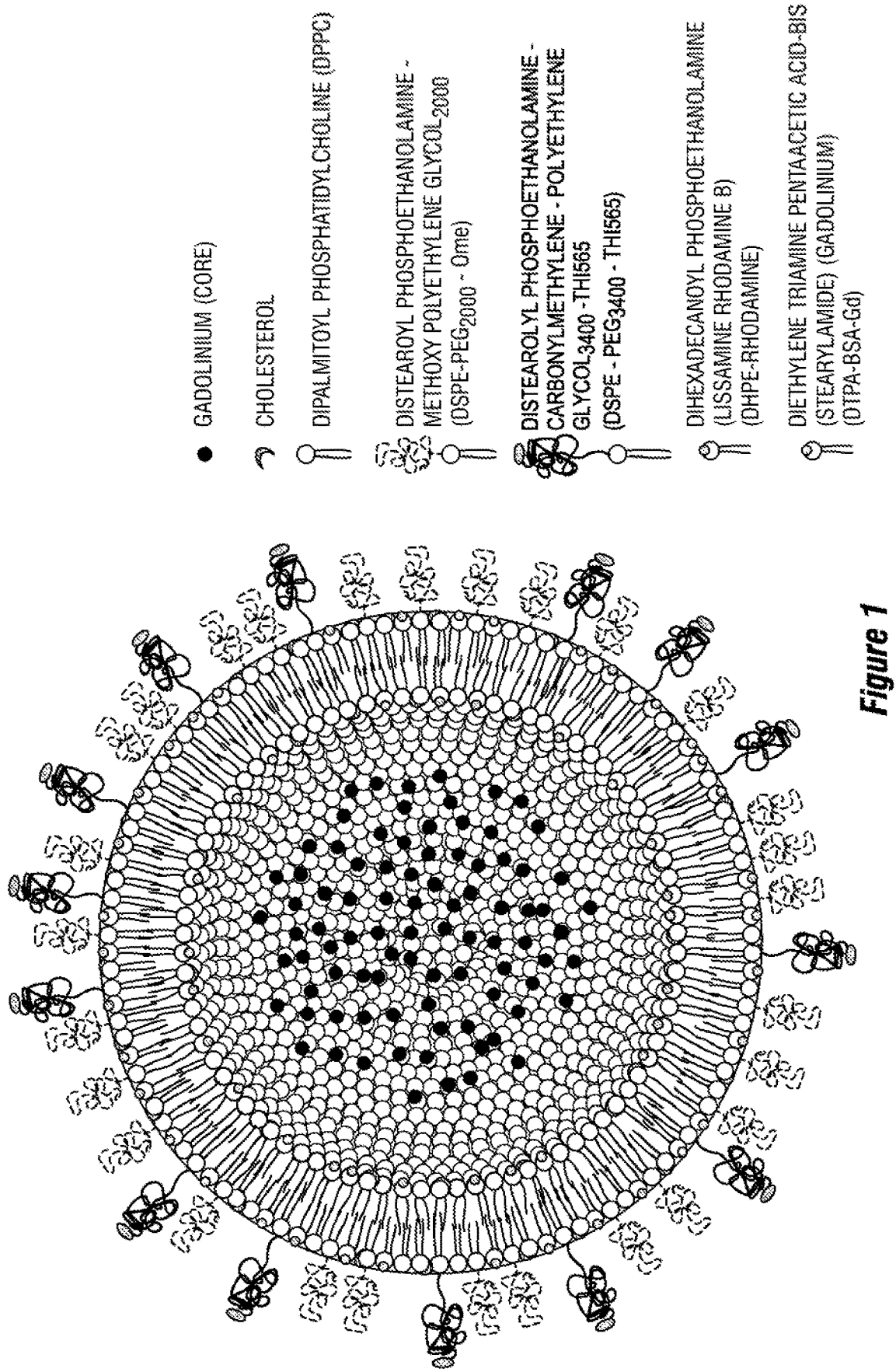
FIG. 1 illustrates the structure of integrin antagonist targeted liposomes. THI567 (Distearoyl phosphoethanolamine-carbonylmethylene-polyethylene $glycol_{3400}$-THI565 (DSPE-PEG3400-THI565)) is shown. THI567 is incorporated at a level of 1% and liposome size is 150 nm.
Figure 2C:
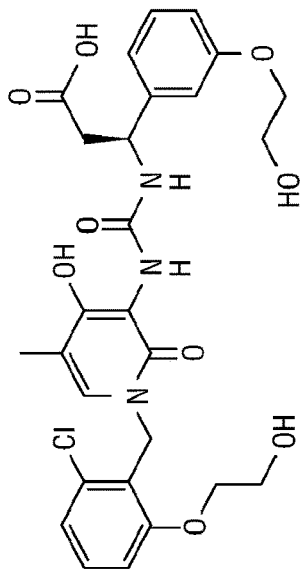
FIG. 2C illustrates THI565 and THI0567 inhibition of α4β1-K562 cell adhesion to VCAM-1 ($Mn^{++}$).
Figure 2C:
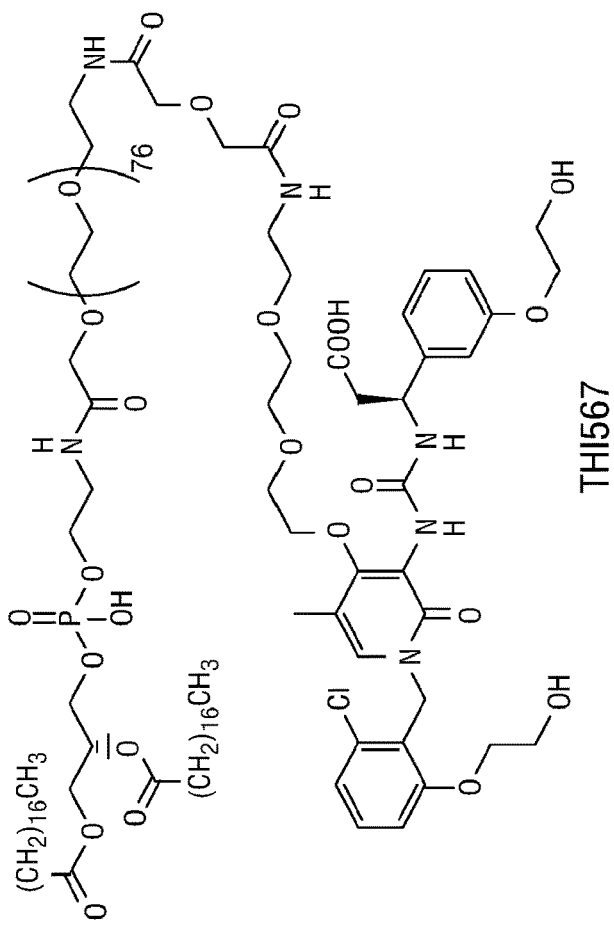
Figure 2C:
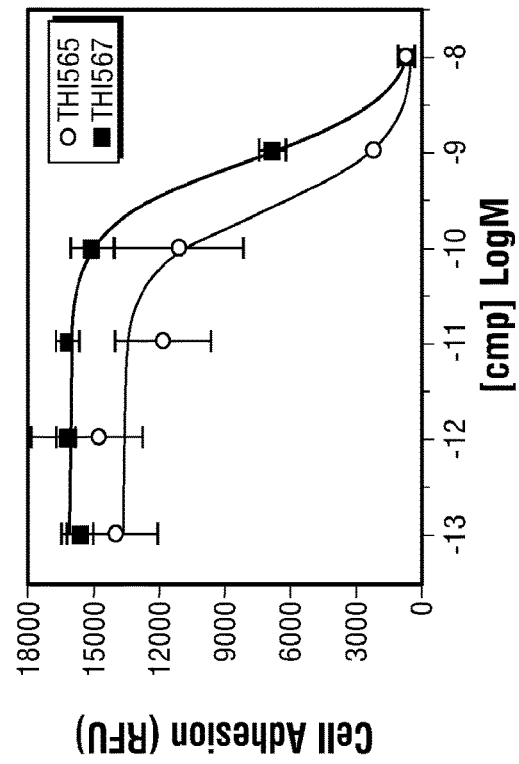
Figure 3A:
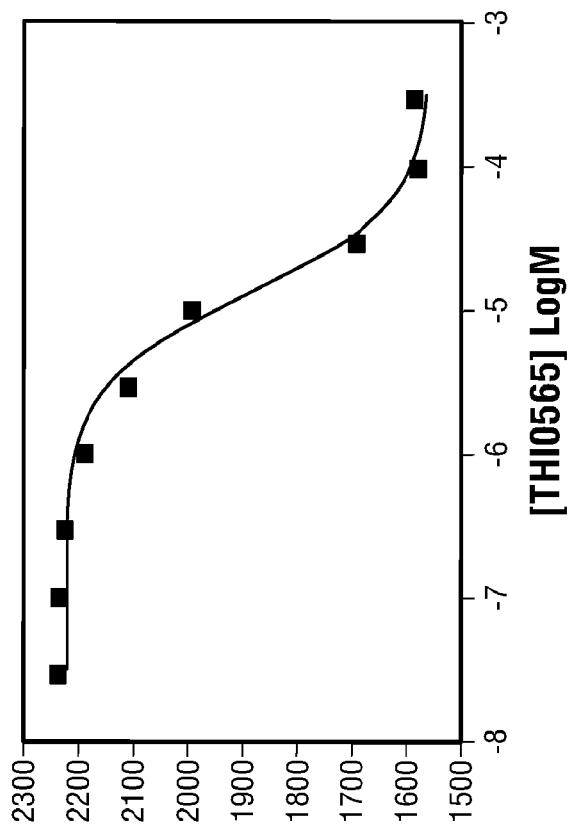
FIG. 3A illustrates THI1565 structure.
Figure 3A:
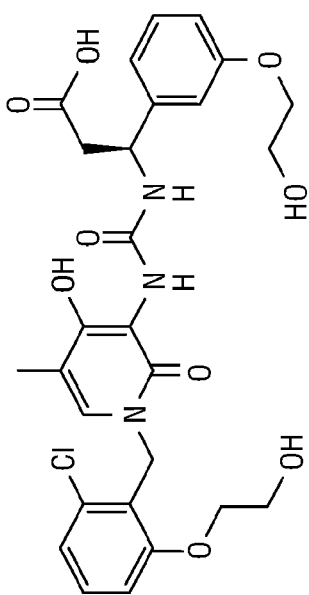
Figure 4A:
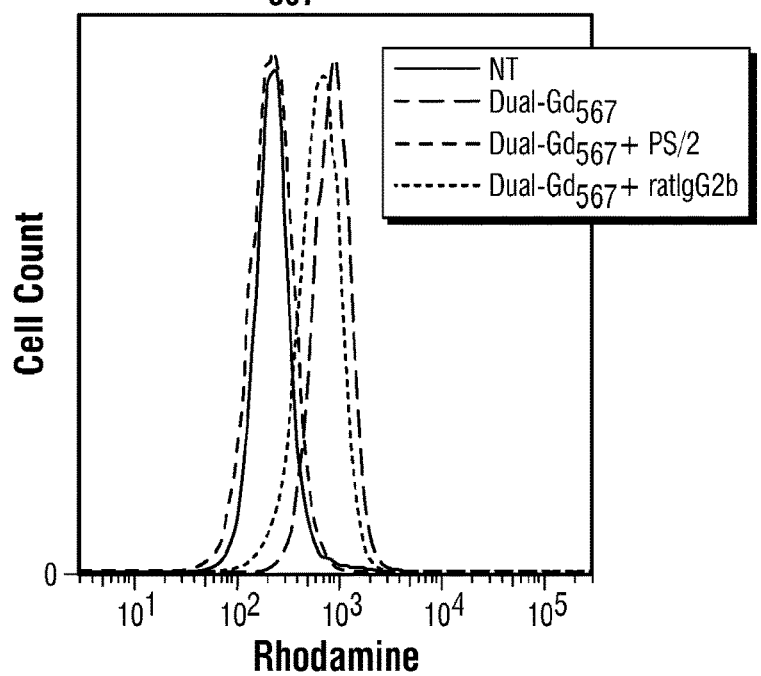
FIG. 4 illustrates specific binding of THI567-targeted liposome binding to integrin α4β1. THI567-targeted liposomes, or non-targeting liposome binding is shown in part A. In part B, anti-α4 integrin mAb PS/2 was used to inhibit THI567-targeted liposomes (150 nm; 1.0%) binding to α4β1-K352 cells. THI567-targeted liposomes (150 nm; 1.0%) were used at a concentration of $2 \times^{-10}$ pM, and PS/2, or iso type control antibody rat IgG2b was used at a concentration of 10 ug/ml). Rhodamine fluorescence was detected by flow cytometry and expressed as geometric mean fluorescence intensity (gMFI) in both panels.
Figure 4B:
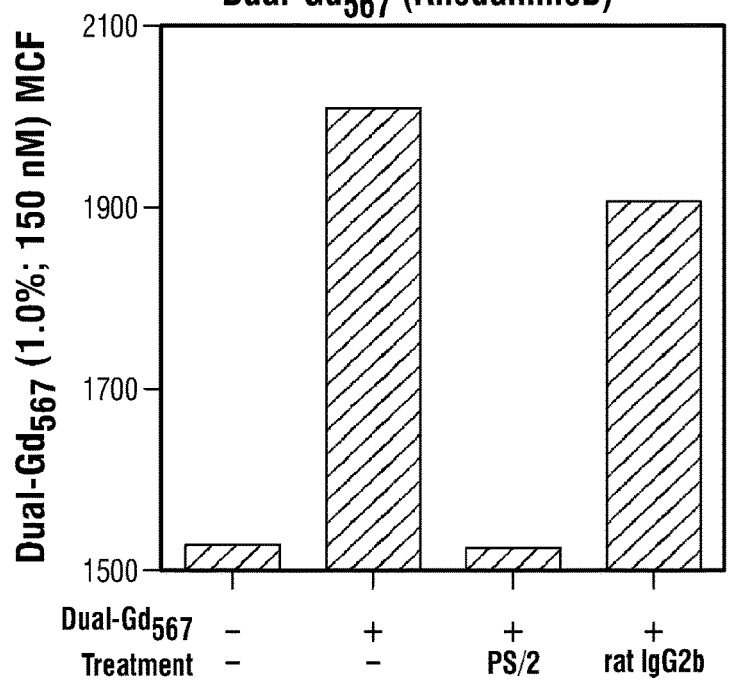
Figure 5A:
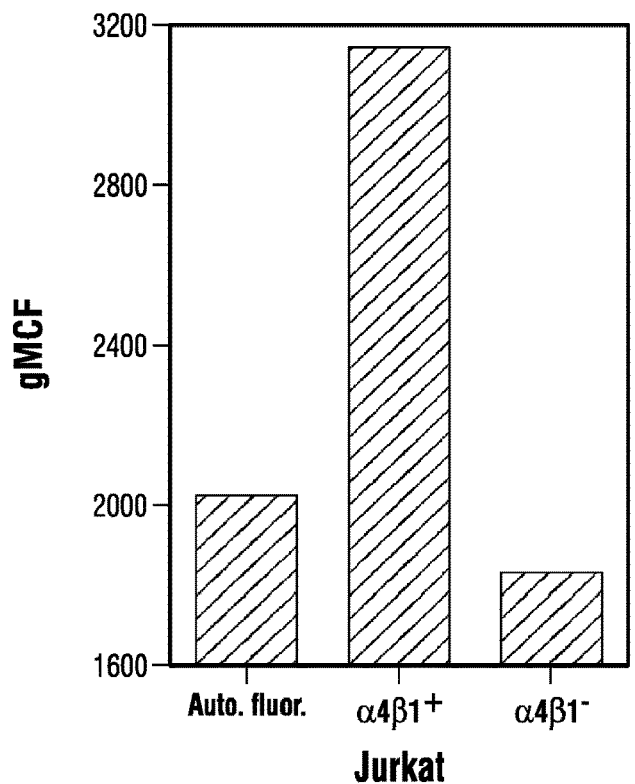
FIG. 5A shows binding to Jurkat cells.
Figure 5B:
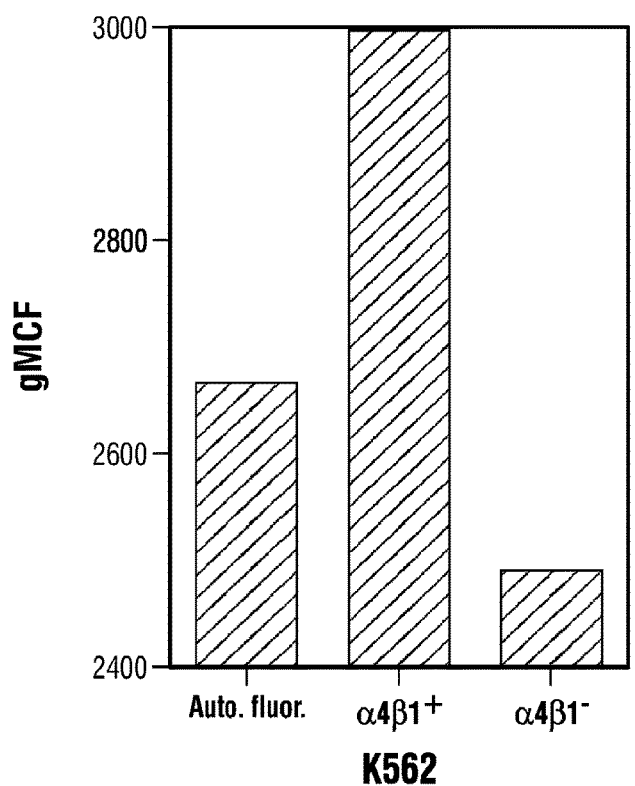
FIG. 5B represents binding to K562. Data is expressed as geometric mean fluorescence intensity (gMFI).

The term "alkyl" as used herein, alone or in combination, refers to C1-C22 straight or branched, substituted or unsubstituted saturated chain radicals derived from saturated hydrocarbons by the removal of one hydrogen atom, unless the term alkyl is preceded by a Cx-Cy designation. Representative examples of alkyl groups include methyl, ethyl, n-propyl, iso-propyl, n-butyl, sec-butyl, iso-butyl, tert-butyl, and stearyl among others.

The term "alkenyl" as used herein, alone or in combination, refers to a substituted or unsubstituted straight-chain or substituted or unsubstituted branched-chain unsaturated hydrocarbon radical containing from 2 to 22 carbon atoms. The term alkenyl as used herein can be taken to mean a chain containing one or more degrees of unsaturation. Examples of such radicals include, but are not limited to, ethenyl, E- and Z-pentenyl, decenyl, docosa-3,6,9,12,15,18-hexaenyl and the like.

The term "alkynyl" as used herein, alone or in combination, refers to a substituted or unsubstituted straight or substituted or unsubstituted branched chain unsaturated hydrocarbon radical containing from 2 to 10 carbon atoms and one or more carbon-carbon triple bonds. Examples of such radicals include, but are not limited to ethynyl, propynyl, propargyl, butynyl, hexynyl, decynyl and the like.

The term "lower" modifying "alkyl", "alkenyl", "alkynyl" or "alkoxy" refers to a C1-C6 unit for a particular functionality. For example lower alkyl means C1-C6 alkyl.

The term "aliphatic acyl" as used herein, alone or in combination, refers to radicals of formula alkyl-C(O)—, alkenyl-C(O)— and alkynyl-C(O)— derived from an alkane-, alkene- or alkyncarboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propionyl and methylpropionyl, among others.

The term "cycloalkyl" as used herein refers to an aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

Substituted "cycloalkyl" includes cis or trans forms. Furthermore, the substituents may either be in endo or exo positions in the bridged bicyclic systems.

The term "cycloalkenyl" as used herein alone or in combination refers to a cyclic carbocycle containing from 4 to 8 carbon atoms and one or more double bonds. Examples of such cycloalkenyl radicals include, but are not limited to, cyclopentenyl, cyclohexenyl, cyclopentadienyl and the like.

The term "cycloalkylalkyl" as used herein refers to a cycloalkyl group appended to a lower alkyl radical, including, but not limited to cyclohexylmethyl.

The term "halo" or "halogen" as used herein refers to I, Br, Cl or F.

The term "haloalkyl" as used herein refers to a lower alkyl radical, to which is appended at least one halogen substituent, for example chloromethyl, fluoroethyl, trifluoromethyl and pentafluoroethyl among others.

The term "alkoxy" as used herein, alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkoxyalkyl" as used herein, refers to $R_Y$—O—RZ, wherein $R_Y$ is lower alkyl as defined above, and Rz is alkylene (—$(CH_2)_w$—) wherein w is an integer of from one to six. Representative examples include methoxymethyl, methoxyethyl, and ethoxyethyl among others.

The term "alkenoxy" as used herein, alone or in combination, refers to a radical of formula alkenyl-O—, provided that the radical is not an enol ether, wherein the term "alkenyl" is as defined above. Examples of suitable alkenoxy radicals include, but are not limited to, allyloxy, E- and Z-3-methyl-2-propenoxy and the like.

The term "alkynoxy" as used herein, alone or in combination, refers to a radical of formula alkynyl-O, provided that the radical is not an -ynol ether. Examples of suitable alkynoxy radicals include, but are not limited to, propargyloxy, 2-butynyloxy and the like.

The term "carboxy" as used herein refers to C(O)OH.

The term "thioalkoxy" refers to a thioether radical of formula alkyl-S—, wherein "alkyl" is as defined above.

The term "sulfonamido" as used herein refers to —$SO_2NH_2$.

The term "carboxaldehyde" as used herein refers to —C(O)R wherein R is hydrogen.

The terms "carboxamide" or "amide" as used herein refer to C(O)$NR_aR_b$ wherein $R_a$ and $R_b$ are each independently hydrogen, alkyl or any other suitable substituent.

The term "alkoxyalkoxy" as used herein refers to $R_cO$—$R_dO$— wherein $R_c$ is lower alkyl as defined above and $R_d$ is alkylene wherein alkylene is —$(CH2)_n$— wherein n is an integer horn 1 to 6. Representative examples of alkoxyalkoxy groups include methoxymethoxy, ethoxymethoxy, t-butoxymethoxy among others.

The term "alkylamino" as used herein refers to $R_c$NH— wherein $R_c$ is a lower alkyl group, for example, ethylamino, butylamino, among others.

The term "alkenylamino" as used herein, alone or in combination, refers to a radical of formula alkenyl-NH— or (alkenyl)$_2$N—, wherein the term "alkenyl" is as defined above, provided that the radical is not an enamine. An example of such alkenylamino radical is the allylamino radical.

The term "alkynylamino" as used herein, alone or in combination, refers to a radical of formula alkynyl-NH— or (alkynyl)$_2$N— wherein the term "alkynyl" is as defined above, provided that the radical is not an —C≡C—$NH_2$ or —C≡C—NH. An example of such alkynylamino radicals as used herein is the propargyl amino radical HC≡C—$CH_2NH$—.

The term "dialkylamino" as used herein refers to $(R_f)(R_g)$N— wherein $R_f$ and $R_g$ are independently selected from lower alkyl, for example diethylamino, and methyl propylamino, among others.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, and isopropoxycarbonyl among others.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group containing at least one endocyclic N, O or S atom such as furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, indolizinyl, indolyl, isoindolyl, 3H-indolyl, indolinyl, benzo[b] furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Aralkyl" and "alkylaryl" employ the term "alkyl" as defined above. Rings may be multiply substituted.

The term "aralkyl" as used herein, alone or in combination, refers to an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "aralkenyl" as used herein, alone or in combination, refers to an aryl substituted alkenyl radical, wherein the terms "aryl" and "alkenyl" are as defined above.

The term "arylamino" as used herein, alone or in combination, refers to a radical of formula aryl-NH—, wherein "aryl" is as defined above. Examples of arylamino radicals include, but are not limited to, phenylamino (anilido), naphthylamino, 2-, 3-, and 4-pyridylamino and the like.

The term "benzyl" as used herein refers to $C_6H_5$—$CH_2$—.

The term "biaryl" as used herein, alone or in combination, refers to a radical of formula aryl-aryl, wherein the term "aryl" is as defined above.

The term "thioaryl" as used herein, alone or in combination, refers to a radical of formula aryl-S— wherein the term "aryl" is as defined above. An example of a thioaryl radical is the phenylthio radical.

The term "aroyl" as used herein, alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The term "heterocyclyl" as used herein, alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "alkylheterocyclyl" as used herein refers to an alkyl group as previously defined appended to the parent molecular moiety through a heterocyclyl group, including but not limited to 4-methylpiperazin-1-yl.

The term "heterocyclylalkyl" as used herein refers to a heterocyclyl group as previously defined appended to the parent molecular moiety through an alkyl group, including but not limited to 2-(1-piperidinyl)ethyl.

The term "heterocycloyl" as used herein refers to radicals of the formula heterocyclyl-C(O)—, wherein the term "heterocyclyl" is as defined above.

The term "aminal" as used herein refers to a hemiacetal of the structure $R_hC(NR_iR_j)(NR_kR_l)$— wherein $R_h$, $R_i$, $R_j$, $R_k$ and $R_l$ are each independently hydrogen, alkyl or any other suitable substituent.

The term "ester" as used herein refers to —$CO_2R_m$, wherein $R_m$ is alkyl or any other suitable sub-stituent.

The term "carbamate" as used herein refers to compounds based on carbamic acid NXC(O)OR, wherein for example, X is hydrogen, alkyl, aryl or aralkyl and independently R is alkyl, aryl or aralkyl.

The term "optical isomers" as used herein refers to compounds which differ only in the stereochemistry of at least one atom, including enantiomers, diastereomers and racemates.

In this disclosure, THI0567 and THI567 are used interchangeably; THI0565 and THI565 are used interchangeably.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboxyalkyl, cycloalkyl, cycloalkylalkyl, heterocyclyl, alkylheterocyclyl, heterocyclylalkyl, oxo, arylsulfonyl and aralkylaminocarbo-nyl or any of the substituents of the preceding paragraphs or any of those substituents either attached directly or by suitable linkers. The linkers are typically short chains of 1-3 atoms containing any combination of —C—, —C(O)—, —NH—, —S—, —S(O)—, —O—, —C(O)O— or —S(O)$_2$—. Rings may be substituted multiple times.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in Advanced Organic Chemistry by J. March, 1985, pp. 16-18, incorporated herein by reference. Electron withdrawing groups include halo, nitro, carboxy, lower alkenyl, lower alkynyl, carboxaldehyde, carboxyamido, aryl, quaternary ammonium, trifluoromethyl, sulfonyl and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio, carboxy lower alkyl, arylalkoxy, alkanoylamino, alkanoyl(lower alkyl)amino, lower alkylsufonylamino, arylsulfonylamino, alkylsulfonyl(lower alkyl)amino, arylsulfonyl(lower alkyl) amino, lower alkylcarboxamide, di(lower alkyl) carboxamide, sulfonamide, lower alkylsulfonamide, di(lower alkyl)sulfonamide, lower alkylsulfonyl, arylsulfonyl and alkyldithio.

Fatty acid esters are intended to be those understood by one skilled in the art as the esters formed by long hydrocarbon chains that may be saturated or with varying degrees of unsaturation terminating in a carboxylic acid functional group. Without limiting the scope of the intent of the inventors, fatty acids, by way of example only, may include: palmitic acid, stearic acid, or oleic acid, dodecanoic acid, tetradecanoic acid, hexadecanoic acid, octadecanoic acid, eicosanoic acid, cis-9-hexadecenoic acid, cis-6-octadecenoic acid, cis-9-octadecenoic acid, cis-11-octadecenoic acid, cis-13-docosenoic acid, cis-15-tetracosenoic acid, 9,12-octadecadienoic acid, 6,9,12-octadecatrienoic acid, 9,12,15-octadecatrienoic acid, 5,8,11,14-eicosatetraenoic acid, 5,8,11,14,17-eicosapentaenoic acid, or 4,7,10,13,16,19-docosahexanoic acid.

Likewise, this disclosure involves using a polymeric linker consisting of polyethylene glycol or alternatively represented as —$(CH_2CH_2O)_n$— units that inherently contains a distributions) of molecular weights making up the average. As a result, molecular weights are expressed as an average molecular weight reflective of the mean across the distribution or distributions of individual masses present. In an embodiment, the number of —$(CH_2CH_2O)$— monomer units in THI567 is from 7 to 115. In an embodiment, the number of —$(CH_2CH_2O)$— monomer units in THI567 is from 38 to 115. In an embodiment, the number of —$(CH_2CH_2O)$— monomer units in THI567 is from 38 to 100. In an embodiment, THI567 is a mixture of molecules having 38-115 —$(CH_2CH_2O)$— monomer units. Thus, by way of example, THI567 is a mixture of molecules and has a target average of 76 —$(CH_2CH_2O)$— monomer units, and in one example an actual average of 70-71 units of —$(CH_2CH_2O)$—.

In one example thereof, the distribution contained a molecular mass +/− about 1500 mass units by mass spectrometry. The invention is meant to encompass the whole of the individual components making up the distribution or distributions of compounds contributing to the average molecular weight. The claimed average therefore includes within its definition the range up to about +/−38-$(CH_2CH_2O)$— monomer units. The term polyethylene glycol is used to represent the L2 linker divalent radical. The term molecular weight is used to represent the average across the distribution of possible products as represented in this paragraph. One skilled in the art would recognize the variance in molecular weight distribution from batch to batch. For example, the reagent DSPE-PEG$_{3400}$-NH$_2$ would be understood to include variations from batch to batch, but remain within the reported specification for that molecular weight range.

Pharmaceutically acceptable salts are well known in the art. For example, S. M. Berge, et al., describe pharmaceutically acceptable salts in detail in j. Pharmaceutical Sciences, 66: 1-19 (1977). The salts can be prepared in situ during the final isolation and purification of the compounds taught herein, or separately by reacting a free base or free acid function with a suitable reagent, as described generally below. For example, a free base function can be reacted with a suitable acid. Furthermore, where the compounds taught herein carry an acidic moiety, suitable pharmaceutically acceptable salts thereof may, without limiting the scope of the invention, include metal salts such as alkali metal salts, e.g., sodium or potassium salts; and alkaline earth metal salts, e.g., calcium or magnesium salts. One skilled in the art would recognize that the second lipid may be substituted with shorter polymer chain lengths, (e.g. DSPE-mPEG (1000)) and still impart stealth properties. One skilled in the art would further recognize that the substitution of the second lipid to shorter chain lengths would allow for substitution of the third lipid to incorporate shorter polymer lengths, (e.g. DSPE-PEG2000-THI565) that maintains a chain length longer than that of the second lipid.

Integrin targeting agent means a molecule designed to recognize an integrin located on the cell surface and has the effect of homing a liposome to the sight of said cells. The integrins anticipated herein are those of the alpha4beta1 (α4β1), alpha4beta7 (α4β7) and alpha9beta1 (α9β1) family of integrins. The integrin targeting agents, such as THI567, are designed for incorporation into delivery mechanisms such as liposomes and each individually require the other for complete functionality, e.g., imaging specific tissues such as atherosclerotic plaques. The term may be used interchangeably with the term "conjugate", such as "THI-565 conjugate" (i.e. THI567).

In an embodiment, the integrin targeting agent has an average molecular weight (MW) of from 2000 to 7000. In an embodiment, the integrin targeting agent has an average molecular weight (MW) of from 3150 to 6850. In an embodiment, the integrin targeting agent has an average molecular weight (MW) of from 3300 to 6700. In an embodiment, the integrin targeting agent has an average molecular weight (MW) of from 3450 to 6550.

The term bio-active agent means, by way of example only and without limitation, chemotherapeutics such as doxorubicin, paclitaxel, daunorubicin, vincristine, tretinoin, cisplalin, annamycin, vinorelbine, irinotecan HCl, floxuridine; Anti-inflammatories; Immune modulators, such as cyclosporine; wherein the bio-active agent may be delivered to the specific tissues expressing the integrin.

In an embodiment, an integrin targeting agent is produced by forming a functionally protected VLA-4 antagonist of the structure:

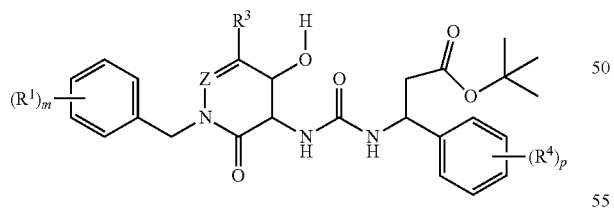

wherein, $R^1$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_3$($C_1$-$C_3$ alkyl), —$NHSO_2$(aryl), —N($C_1$-$C_3$ alkyl)$SO_2$($C_1$-$C_3$ alkyl), —N($C_1$-$C_3$ alkyl)$SO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)?, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl, $OCF_2$, $OCH_2CF_3$, aliphatic acyl, O(cycloalkylalkyl), O(aralkyl), —$SO_2$(1-pyrolidinyl), $SO_2$(1-piperidinyl), piperidinyl, pyrrolidinyl, and —C(O)NH(benzyl) groups;

Z is N or $CR^2$;

$R^2$, when present, and $R^3$ are each independently selected from the group consisting of hydrogen, halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl), —C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$)amino, —C(O)O—($C_1$-$C_3$) alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$($C_1$-$C_3$ alkyl), sulfonamido, carbamate, aryloxyalkyl and —C(O)NH(benzyl) groups; and wherein $R^2$, when present, and $R^3$ may be taken together to form a ring;

$R^4$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$ alkyl)amino, —C(O)O—($C_1$-$C_3$)alkyl, —C(O)NH—($C_1$-$C_3$ alkyl), —C(O)N($C_1$-$C_3$ alkyl)$_2$, —CH=NOH, —$PO_3H_2$, —$OPO_3H_2$, haloalkyl, alkoxyalkoxy, hydroxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl, O(haloalkyl), O(cycloalkyl), O(cycloalkylalkyl), piperidinyl, pyrrolidinyl and —C(O)NH(benzyl) groups;

$R^1$, $R^2$, $R^3$ and $R^4$ are independently unsubstituted or substituted with at least one electron donating or electron withdrawing group;

synthesizing a phospholipid by alkylating at the pyridone hydroxyl with a functionalized 3-17 atom linking group; optionally modifying the terminal functional group; attaching to a polymeric group suitable for liposome formation by means of amide coupling, carbamate formation or triazole formation, and deprotection of functional groups.

In an embodiment, a liposome according to this disclosure is produced by combining DSPE-PEG3400-VLA-4 targeting agent (e.g. DSPE-PEG3400-THI565) in an amount of 0.05 to 1.0% or 0.05 to 2.0% of the total pre-diluted components, with Cholesterol, DSPE-Peg2000, optionally Gd-DTPA-BSA, Gd-DOTA-DSPE or DSPE; and variable amount of DPPC; optionally adding an amount of rhodamine DHPE or pharmaceutically active ingredient; diluting with ethanol; hydrating in 150 mM Saline/10 mM Histine solution; extrusion to form particle size of 400 nm or less; and optionally, purification by various methods known in the art, for example, by dialysis.

In an embodiment, a liposome according to this disclosure is produced by:

Step one: DPPC, Cholesterol, DSPE-MPEG2000, Gd-DTPA-BSA and DSPE-PEG3400-THI565 were respectively constituted based on the desired surface targeting ligand expression at molar proportions shown in the following table:

| Surface Ligand (mol %) | DPPC | Cholesterol | DSPE-MPEG2000 | Gd-DTPA-BSA | DSPE-PEG3400-THI565 (THI567) |
|---|---|---|---|---|---|
| 0.05% | 31.95 | 40 | 3 | 25 | 0.05 |
| 0.25% | 31.75 | 40 | 3 | 25 | 0.25 |
| 1.0% | 31.0 | 40 | 3 | 25 | 1.0 |

Step two: To each of these lipid compositions was added rhodamine DHPE (1.0 to 2.5 mg), and particle formulation as previously described in Ghaghada K B, Ravoori M, Sabapathy D, Bankson J, Kundra V, Annapragada A. New Dual Mode Gadolinium Nanoparticle Contrast Agent for Magnetic Resonance Imaging. Yang S, editor. PLoS ONE. 2009 Oct. 29; 4(10):e7628. Briefly, the lipids (467.4 mgs) were dissolved in ethanol (1.0 to 1.2 mL) followed by hydration at 63-65° C. for 40 minutes in 150 mM saline/10 mM histidine (9 mLs) to achieve a lipid concentration of 50 mM. The mixture was then extruded in a 10 ml Lipex extruder (Northern Lipids Inc., Burnaby, Canada) using a 400 nm polycarbonate track-etch filter (5 passes), to obtain particles with a mean diameter of ~250 nm. For particles with mean diameter of ~150 nm, the ensuing formulation was further extruded through a 200 nm polycarbonate filter (8 passes), and for particles with a mean diameter of ~100 nm, the formulation was further extruded (5 times) through 100 nm filters. The resulting solutions was then dialyzed against 150 mM saline/10 mM histidine. The mean liposome size in the final formulation was determined by dynamic light scattering (DLS), and the gadolinium and phospholipid (equivalent phosphorus) concentration in the formulation, quantified using inductively coupled plasma optical emission spectroscopy (ICP-OES). The number of particles/mL was computed based on the particle size and the final lipid concentration in the formulation.

In an embodiment, a composition of this disclosure comprises a plurality of liposomes, wherein the plurality of liposomes comprise an integrin-targeting molecule, wherein the integrin-targeting molecule comprises a polymer derivatized lipid or phospholipid moiety and an integrin-targeting moiety. In an embodiment, the integrin-targeting moiety has one of the following structures:

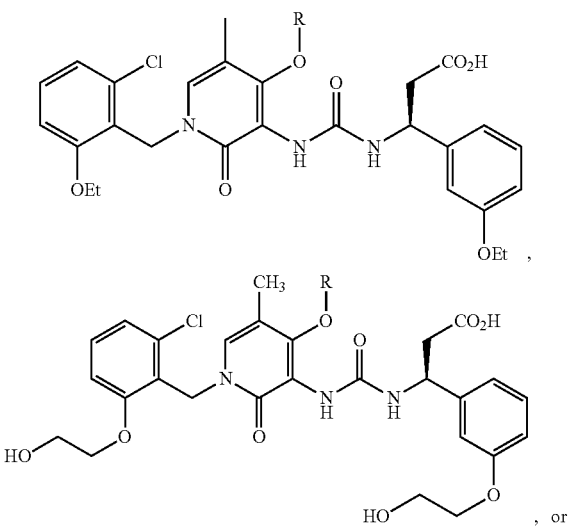

-continued

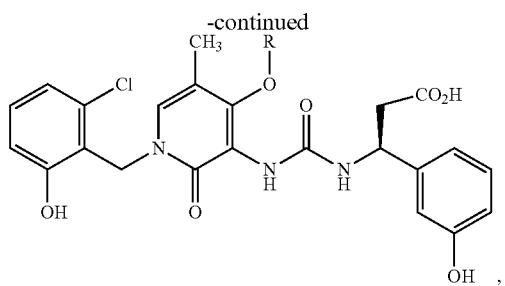

wherein R is the attachment point for the polymer derivatized lipid or phospholipid moiety.

In an embodiment, the integrin-targeting molecule is a compound of this disclosure as discussed herein. In an embodiment, the plurality of liposomes have an average diameter of 150 to 175 nm. In an embodiment, the integrin-targeting molecule comprises about 0.05 to 2 mol % of the plurality of liposomes.

In an embodiment, the plurality of liposomes further comprise a bio-active agent. In an embodiment, the bio-active agent is encapsulated within the plurality of liposomes.

In an embodiment, the plurality of liposomes further comprise a lipid or phospholipid derivatized with a group binding a contrast enhancing agent. In an embodiment, the lipid or phospholipid derivatized with a group binding a contrast enhancing agent comprises a DTPA-Gd or a DOTA-Gd moiety. In an embodiment, the liposomes comprise 30 to 45 mol % DPPC, 15 to 45 mol % cholesterol, 1 to 6 mol % DSPE-MPEG-2000, 20 to 30 mol % Gd-DOTA-DSPE, and 0.05 to 2 mol % THI-567.

In an embodiment, a method of delivering a bio-active agent to a target cell in a patient comprises administering the composition of this disclosure to the patient. In an embodiment, the bio-active agent is selectively delivered to cells expressing α4β1 integrin. In an embodiment, the cells expressing α4β1 integrin comprise one or more of the following types of cells: CD11b+ mononuclear cells, CD3+ T cells, CD19+ B cells, and Ly-6G+ polymorphonuclear leukocytes.

In an embodiment, a method of imaging a biological structure in a subject comprises administering to the subject a composition of this disclosure and detecting the contrast enhancing agent with an imager. In an embodiment, liposomes in the composition become enriched in the biological structure. In an embodiment, the imager performs one of the following techniques: CT, micro-CT, mammography. X-ray, MRI, magnetic resonance spectroscopy, bioluminescence imaging, ultrasound, optical imaging, optical spectroscopy, fluorescence spectroscopy, fluorescence imaging, near-infrared spectroscopy, and near-infrared imaging.

In an embodiment, the imager is an MRI scanner having a field strength of no more than 3T. In an embodiment, the imager is an MRI scanner having a field strength of no more than 1T. In an embodiment, the biological structure is an atherosclerotic plaque, a plurality of cells expressing α4β1 integrin, or a tumor.

In an embodiment, a method of identifying a patient at risk for an acute ischemic event comprises: (a) administering to the subject the composition of any one of claims 11 to 23, 55, or 56; (b) detecting the contrast enhancing agent with an MRI scanner to generate an image; (c) evaluating the image for the presence of atherosclerotic plaques; and (d) identifying the patient as being at risk for an acute ischemic event if atherosclerotic plaques are detected.

Advantages. Without wishing to be limited by theory, it has been surprisingly discovered that the integrin targeting agent of this disclosure has enabled MRI images to be obtained at clinically relevant field strength, e.g., 1 Tesla, as demonstrated in Scientific Reports (2018) 8:3733, the disclosure of which is herein incorporated by reference. Without wishing to be limited by theory, it has been surprisingly discovered that the liposomes of this disclosure has enabled MRI images to be obtained at clinically relevant field strength, e.g., 1 Tesla, as demonstrated in Scientific Reports (2018) 8:3733, the disclosure of which is herein incorporated by reference.

EXAMPLES

The following are intended to be representative of the invention, which is in no way limited by the specific examples shown. One skilled in the art would recognize the general applicability of making other examples without departing from the spirit and scope of this invention. All reagents used in the subsequent examples were obtained from commercial sources and were used without further purification. DSPE-PEG$_{3400}$-NH$_2$ was obtained from Laysan Bio, Inc.

Example 1

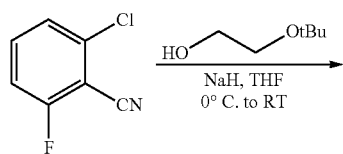

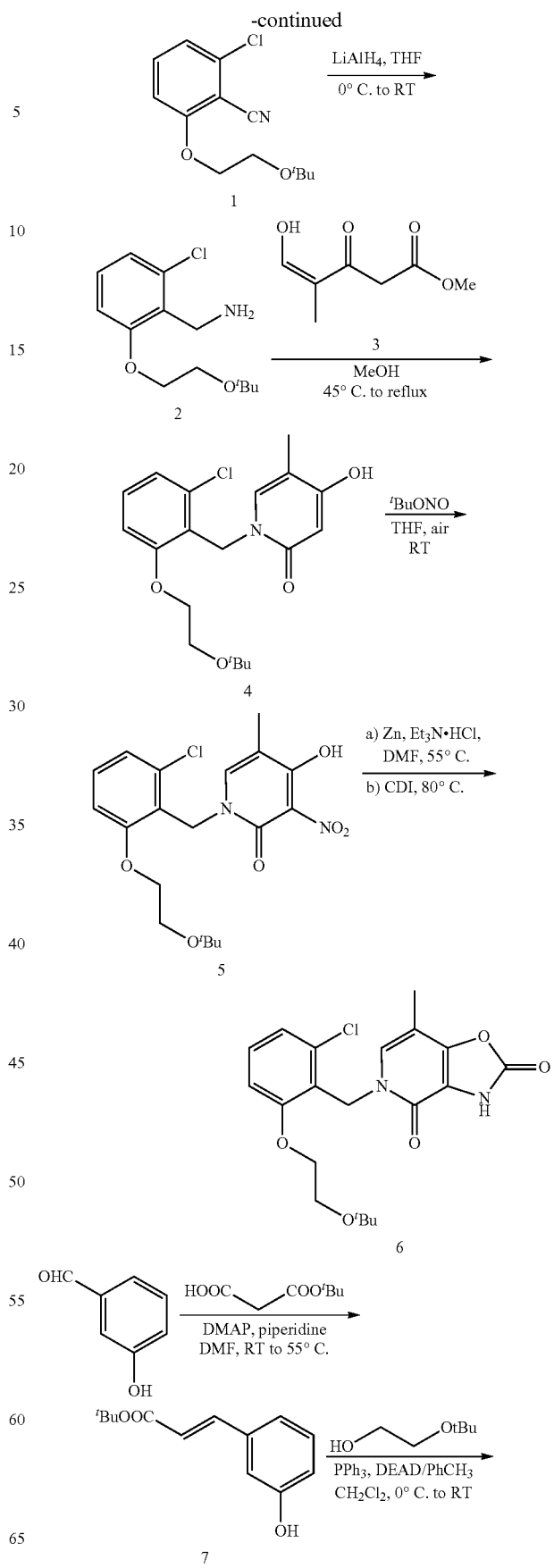

-continued

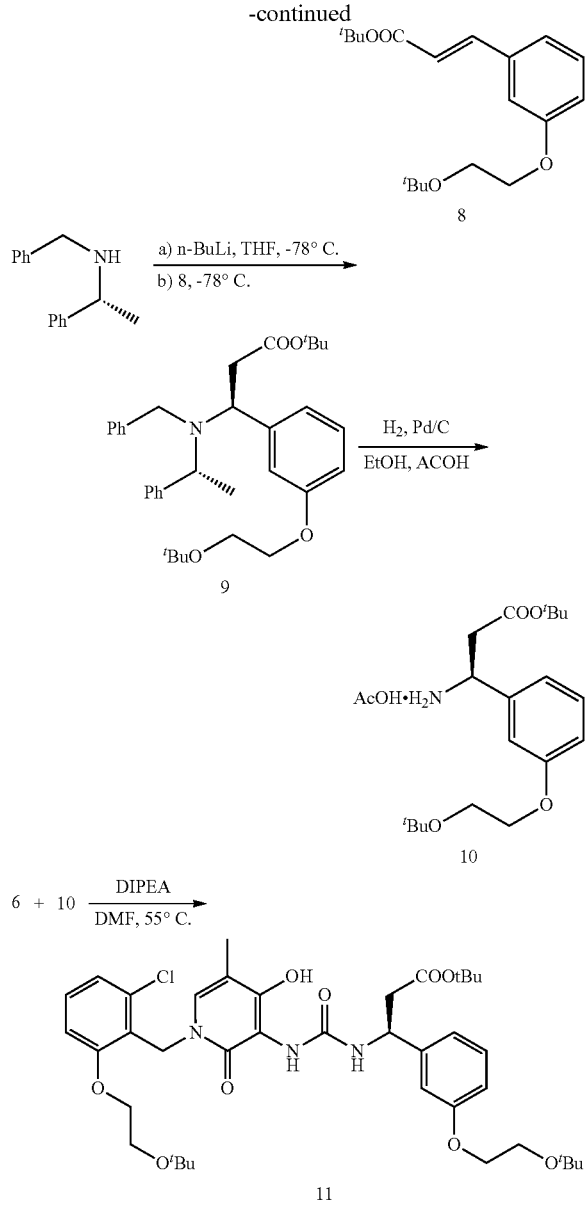

Step One: To a solution of ethylene glycol mono tert-butyl ether (3.44 mL, 3.096 g, 26.2 mmol) in anhydrous tetrahydrofuran (26.2 mL) at 0° C. under argon, sodium hydride (60% dispersion in mineral oil, 655 mg, 16.4 mmol) was added in several portions. The mixture was stirred at 0° C. for 30 minutes and 2-chloro-6-fluorobenzonitrile (2.028 g, 13.1 mmol) was added. The reaction mixture was allowed to slowly warm to room temperature and was stirred overnight. The mixture was diluted with a 1:1 mixture of hexanes:ethyl acetate, and washed with water (twice) and brine. The organic layer was dried over magnesium sulfate, filtered, and concentrated under reduced pressure. The residue was purified by automated silica gel chromatography (Biotage®, SNAP 50 KP-Sil, 0-50% ethyl acetate in hexanes) to give 1 (3.22 g) as a colorless oil.

Step Two: To a solution of 1 (3.21 g, 12.7 mmol) in anhydrous tetrahydrofuran (94 mL) cooled 0° C. under argon, a solution of lithium aluminum hydride (2.0 M in tetrahydrofuran, 12.7 mL, 25.4 mmol) was added dropwise by syringe. The mixture was allowed to gradually warm to room temperature, and was stirred overnight. The mixture was recooled to 0° C., than water (0.97 mL) was added dropwise by syringe. The mixture was vigorously stirred for 10 minutes, then a solution of sodium hydroxide (20% by weight in water, 0.71 mL) was added dropwise and stirring was continued for 10 minutes. Finally, water (3.53 mL) and Celite® filter aid were added. The mixture was diluted with diethyl ether, vigorously stirred for 30 minutes, then filtered through additional Celite®, washing with ether. The filtrate was concentrated under reduced pressure to give 2 (3.27 g) as a pale yellow oil. This material was used without purification.

This procedure was also used to prepare (2-(tert-butoxy)-6-chlorophenyl)methanamine from 12.

Step Three: To a flask containing 3 (prepared according to the procedures described in Step One of Example 25 in U.S. Pat. No. 6,972,296, 2.11 g, 13.3 mmol), a solution of 2 (3.26 g, 12.7 mmol) in methanol (50 mL) was added along with a methanol rinse (14 mL). The resulting mixture was heated to 45° C. overnight, then refluxed for 24 hours. The mixture was cooled to room temperature and concentrated under reduced pressure. The residue was taken up in ethyl acetate and concentrated (twice). The residue was then suspended in ethyl acetate (30 mL), stirred 30 minutes, then filtered, washing with ethyl acetate. The solid was dried under vacuum to give 4 (1.47 g) as a light yellow powder.

This procedure was also used to prepare 1-(2-(tert-butoxy)-6-chlorobenzyl)-4-hydroxy-5-methylpyridin-2(1H)-one from (2-(tert-butoxy)-6-chlorophenyl)methanamine.

Step Four (Reference: D Koley, O C Colón, SN Savinov. Org. Lett. 2009, 11, 4172-75.) To a suspension of 4 (1.789 g, 4.89 mmol) in tetrahydrofuran (25 mL) at room temperature open to air, tert-butyl nitrite (1.74 mL, 14.7 mmol) was added. The resulting mixture was stirred overnight, then was diluted with methanol (10 mL) and concentrated under reduced pressure to give 5 as a dark yellow oil. This material was used without purification.

This procedure was also used to prepare 1-(2-(tert-butoxy)-6-chlorobenzyl)-4-hydroxy-5-methyl-3-nitropyridin-2(1H)-one from 1-(2-(tert-butoxy)-6-chlorobenzyl)-4-hydroxy-5-methylpyridin-2(1H)-one.

Step Five: To a solution of crude 5 (4.89 mmol theoretical from step four) in N,N-dimethylformamide (DMF) (16.3 mL), zinc dust (1.44 g, 22.0 mmol) and triethylamine hydrochloride (3.702 g, 26.9 mmol) were added. The mixture was heated to 55° C. for 3 hours, cooled to room temperature, and 1,1'-carbonyldiimidazole (2.379 g, 14.7 mmol) was added in a single portion. The mixture was heated to 80° C. for 1.5 hours, the was cooled to room temperature. The crude reaction mixture was filtered into a flask containing water (200 mL) washing with a small amount of DMF. The resulting suspension was filtered, washing the collected solid with water. The solid was then partitioned between dichloromethane and aqueous HCl (2N). The aqueous layer was extracted twice with dichloromethane, and the combined organic layers were washed with water, then dried over magnesium sulfate, filtered and concentrated to give 6 (1.91 g) as an orange-tan solid. This material was used without purification.

This procedure was also used to prepare 5-(2-(tert-butoxy)-6-chlorobenzyl)-7-methyloxazolo[4,5-c]pyridine-2,4 (3H,5H)-dione from 1-(2-(tert-butoxy)-6-chlorobenzyl)-4-hydroxy-5-methyl-3-nitropyridin-2(1H)-one.

Step Six: (Reference: B List, et. al. Adv. Synth. Catal. 2005, 347, 1558-60.) To a solution of N,N-dimethyaminopyridine (DMAP) (200 mg, 1.64 mmol) in DMF (41 mL) at room temperature under argon, tert-butyl hydrogen malonate (3.94 g, 24.6 mmol) and 3-hydroxybenzaldehyde (2.00 g, 16.4 mmol) were added. Piperazine (0.16 mL, 1.64 mmol) was added and the mixture was stirred at room temperature three days. Thin layer chromatography (TLC) indicated significant starting material remained, so the mixture was heated to 55° C. overnight, then cooled to room temperature. The mixture was diluted with water (200 mL) and was extracted with 4:1 hexanes:ethyl acetate. The organic layer was washed with saturated aqueous ammonium chloride, water (twice), and brine, then was dried over magnesium sulfate, filtered and concentrated under reduced pressure to give 7 (3.73 g) as a white solid. This material contained trace residual solvent, but was used without further purification.

This procedure was also used to prepare (E)-tert-butyl 3-(3-(tert-butoxy)phenyl)acrylate from 13.

Step Seven: To a solution of 7 (2.04 g, 9.26 mmol) in dichloromethane (46 mL) at 0° C. under argon, ethylene glycol mono tert-butyl ether (1.58 mL, 12.04 mmol) was added by syringe followed by triphenylphosphine (3.65 g, 13.9 mmol). The mixture was stirred 10 minutes, then a solution of diethyl azodicarboxylate (40% by weight in toluene, 6.33 mL, 13.9 mmol) was added. After stirring at room temperature overnight, TLC indicated partial conversion. Additional portions of ethylene glycol mono tert-butyl ether (0.79 mL, 6.0 mmol), triphenylphosphine (1.82 g, 7.0 mmol), and diethyl azodicarboxylate (3.2 mL, 7.0 mmol) were added, and the mixture was stirred an additional 24 hours, then was concentrated under reduced pressure. The residue was taken up in 3:1 hexanes:ethyl acetate and the solution was washed with water (twice) and brine. The organic layer was dried over magnesium sulfate, filtered and concentrated under reduced pressure. The residue was taken up in 9:1 hexanes:dichloromethane with heating to give a clear solution, that was allowed to cool to room temperature and stand overnight. Some crystals adhered to the side of the flask which were by-products from the reaction. The solution was decanted and applied directly to a 5-inch plug of silica gel, which was sequentially eluted with 9:1 hexanes:dichloromethane, 19:1 hexanes:ethyl acetate, 9:1 hexanes:ethyl acetate and finally 3:1 hexanes:ethyl acetate to give 8 (2.029 g) as a pale yellow oil. A small amount of unreacted starting material (0.39 g) was also isolated.

Step Eight: To a solution of (R)-(+)-N-benzyl-α-methylbenzylamine (1.77 g, 8.40 mmol) in tetrahydrofuran (28 mL) cooled to –78° C. under argon, n-butyllithium (1.6 M in hexanes, 4.88 mL, 7.80 mmol) was added dropwise over 10 minutes. The bright red solution was stirred at –78° C. for 30 minutes, and a solution of 8 (2.029 g, 6.33 mmol) in tetrahydrofuran (8 mL) was added dropwise by syringe along with a THF (2 mL) rinse. The resulting solution was stirred at –78° C. for 4 hours, absolute ethanol (3 mL) was added, followed by saturated aqueous ammonium chloride (25 mL). The resulting mixture was allowed to warm until the ice had completely melted, then was extracted with 3:1 hexanes:ethyl acetate. The organic layer was washed with water (twice), a 1:1 mixture of saturated aqueous sodium bicarbonate:water and brine, dried over magnesium sulfate (anhydrous), filtered and concentrated under reduced pressure. The residue was purified by automated chromatography on silica gel (Biotage®, SNAP100 KP-Sil, eluting with 5>20% ethyl acetate in hexanes) to give 9 (2.98 g) as a colorless viscous oil.

This procedure was also used to prepare (S)-tert-butyl 3-(benzyl((R)-1-phenylethyl)amino)-3-(3-(tert-butoxy)phenyl)propanoate from (E)-tert-butyl 3-(3-(tert-butoxy)phenyl)acrylate, and (S)-tert-butyl 3-(benzyl((R)-1-phenylethyl)amino)-3-(3-(ethoxyphenyl)propanoate from 26.

Step Nine: To a solution of 9 (2.97 g, 5.80 mmol) in absolute ethanol (39 mL) at room temperature under argon, glacial acetic acid (0.5 mL), palladium metal on carbon (Degussa type E101 NE/W, 50% H$_2$O, 10% Pd dry weight basis, 0.98 g, 0.46 mmol Pd). The atmosphere was replaced with hydrogen (toggling between vacuum and hydrogen from a balloon several times) and the reaction was stirred overnight. The mixture was filtered through Celite®, wahing with ethanol, and the filtrate was concentrated under reduced pressure. The residue was recrystallized from diethyl ether and hexanes to give 10 (1.373 g) as a white crystalline solid. No further attempts were made to isolate additional material from the mother liquor.

This procedure was also used to prepare (S)-tert-butyl 3-amino-3-(3-(tert-butoxy)phenyl)propanoate acetate from (S)-tert-butyl 3-(benzyl((R)-1-phenylethyl)amino)-3-(3-(tert-butoxy)phenyl)propanoate, and (S)-tert-butyl 3-amino-3-(3-ethoxyphenyl)propanoate acetate from (S)-tert-butyl 3-(benzyl((R)-1-phenylethyl)amino)-3-(3-ethoxyphenyl) propanoate.

Step Ten: A solution of 6 (1.003 g, 2.46 mmol) and 10 (890 mg, 2.24 mmol) in DMF (12.3 mL) and N,N-diisopropylethylamine (DIPEA) (0.59 mL, 3.36 mmol) under argon was heated to 55° C. for 8 hours. An aliquot indicated unreacted 10, so additional 6 (100 mg, 0.25 mmol) was added and the mixture was heated to 55° C. overnight, cooled to room temperature and then diluted with 1:1 hexanes:ethyl acetate and HCl (2N). The organic layer was washed with water (three times) and brine, dried over MgSO$_4$ and filtered. The filtrate was concentrated under reduced pressure and the resulting residue was purified automated chromatography on silica gel (Biotage®, SNAP100 KP-Sil, eluting with 25-50% ethyl acetate in hexanes). A few fractions containing the desired product also contained an impurity. The fractions were concentrated and re-purified (Biotage®, SNAP10 Ultra, eluting with 30-50% ethyl acetate in hexanes). Fractions from both separations containing the only the desired product were combined and concentrated to give 11 (1.25 g) as a pale yellow foam. This material contained approximately 4% ethyl acetate by weight, but was used as is.

This procedure was also used to prepare (S)-tert-butyl 3-(3-(1-(2-(tert-butoxy)-6-chlorobenzyl)-4-hydroxy-5-methyl-2-oxo-1,2-dihydropyridin-3-yl)ureido)-3-(3-(tert-butoxy)phenyl)propanoate (15) from 5-(2-(tert-butoxy)-6-chlorobenzyl)-7-methyloxazolo[4,5-c]pyridine-2,4(3H,5H)-dione and (S)-tert-butyl 3-amino-3-(3-(tert-butoxy)phenyl) propanoate acetate and (S)-tert-butyl 3-(3-(1-(2-chloro-6-ethoxybenzyl)-4-hydroxy-5-methyl-2-oxo-1,2-dihydropyridin-3-yl)ureido)-3-(3-ethoxyphenyl)propanoate from 5-(2-ethoxy-6-chlorobenzyl)-7-methyloxazolo[4,5-c]pyridine-2,4(3H,5H)-dione (U.S. Pat. No. 6,972,296, compound 151 in example 36) and (S)-tert-butyl 3-amino-3-(3-ethoxyphenyl)propanoate acetate.

Example 2

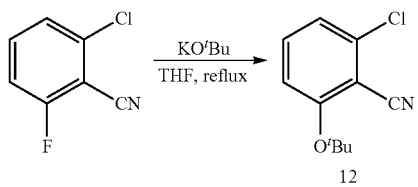

12

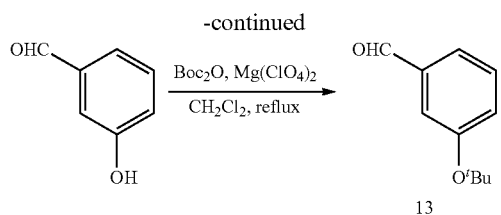

Step One: To a solution of 2-chloro-6-fluorobenzonitrile (1.31 g, 8.4 mmol) in anhydrous tetrahydrofuran (16.8 mL) at room temperature under argon, potassium tert-butoxide (1.04 g, 9.24 mmol) was added. The mixture was heated to reflux overnight, then diluted with a 3:1 mixture of hexanes:ethyl acetate, and washed with water (twice) and brine. The organic layer was dried over magnesium sulfate, filtered, and concentrated under reduced pressure to give 12 (1.655 g) as a pale yellow oil. This material was used without purification.

Step Two: To a solution of 3-hydroxybenzaldehyde (2.059 g, 16.9 mmol) in dichloromethane (26 mL) at room temperature, magnesium perchlorate (379 mg, 1.7 mmol) was added. The mixture was stirred for 10 minutes, then di-tert-butyl dicarbonate (8.48 g, 38.9 mmol) was added. The resulting mixture was heated to reflux for 14 hours, cooled to room temperature, diluted with a 4:1 mixture of hexanes:ethyl acetate, and washed with water (twice) and brine. The organic layer was dried over magnesium sulfate, filtered, and concentrated under reduced pressure. The residue was purified by automated chromatography on silica gel (Biotage®, SNAP100 KP-Sil, eluting with 0-10% ethyl acetate in hexanes) to give 13 (1.64 g) as a colorless oil.

Example 3

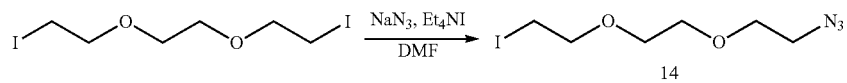

14

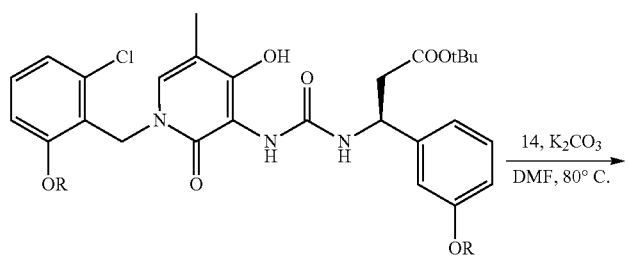

11: R = CH$_2$CH$_2$O$^t$Bu
15: R = $^t$Bu

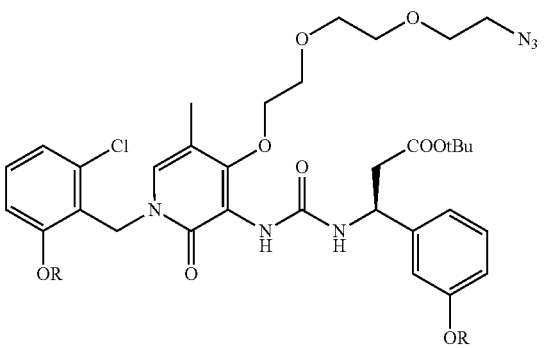

16: R = CH$_2$CH$_2$O$^t$Bu
17: R = $^t$Bu

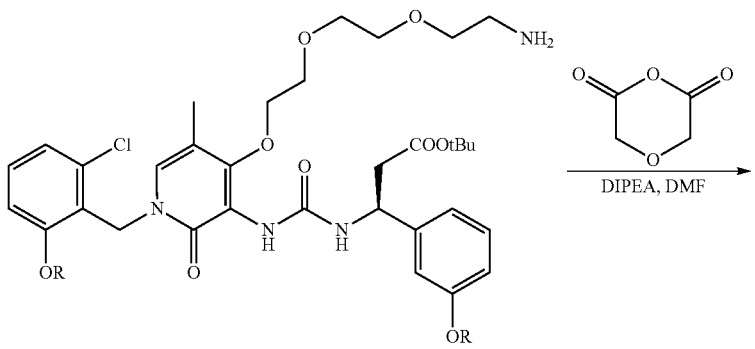

18: R = CH$_2$CH$_2$O$^t$Bu
19: R = $^t$Bu

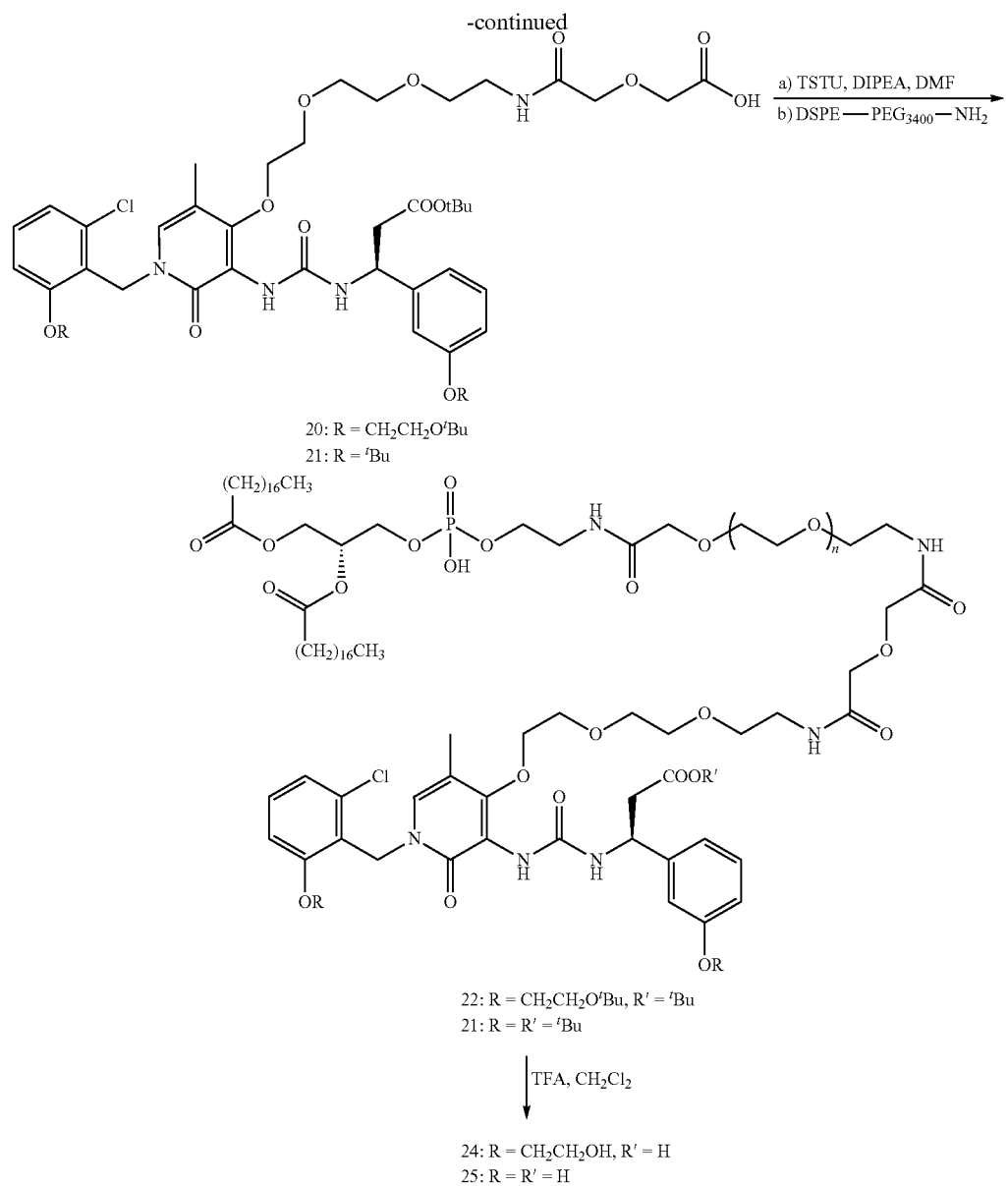

Step One: To a solution of bis-1,2-(2-iodoethoxy)ethane (7.37 g, 19.9 mmol) in DMF (133 mL) at room temperature under argon, sodium azide (1.29 g, 19.9 mmol) and tetraethylammonium iodide (257 mg, 1.00 mmol) were added. The resulting mixture was stirred at room temperature overnight, diluted with water (400 mL), and extracted with 9:1 hexanes:ethyl acetate (100 mL three times). The organic layers were combined, washed with water and brine, dried over magnesium sulfate, filtered, and concentrated under reduced pressure. This gave approximately a statistical mixture of starting material, the desire product, and the bis-azide. This mixture was purified by automated chromatography on silica gel (Biotage®, SNAP100 KP-Sil, eluting with 10-15% ethyl acetate in hexanes) to give 14 (1.95 g) as a yellow oil. Fractions containing both starting material and 14 were concentrated to give approximately a 1:1 mixture (1.15 g) as a yellow oil. No attempt was made to isolate additional 14 from this mixture.

Step Two: to a solution of 11 (1.25 g, 96% 14 by weight, 1.61 mmol) and 14 (918 mg, 3.22 mmol) in DMF (8 mL) at room temperature under argon, potassium carbonate (668 mg, 4.83 mmol) was added. The resulting mixture was heated to 80° C. overnight, cooled to room temperature, diluted with ethyl acetate and washed with water (three times) and brine. The organic layer was dried over magnesium sulfate, filtered, and concentrated under reduced pressure. The residue was purified by automated chromatography on silica gel (Biotage®, SNAP100 KP-Sil, eluting with 50-100% ethyl acetate in hexanes) to give 16 (1.16 g) as a light yellow viscous oil.

This procedure was also used to prepare 17 from 15, and 27 from (S)-tert-butyl 3-(3-(1-(2-chloro-6-ethoxybenzyl)-4-hydroxy-5-methyl-2-oxo-1,2-dihydropyridin-3-yl)ureido)-3-(3-ethoxyphenyl)propanoate (prepared from (S)-tert-butyl 3-amino-3-(3-ethoxyphenyl)propanoate according to the procedures described in Example 34, steps 1-2, Example 36, steps 1-3, and Example 37, step 1 in U.S. Pat. No. 6,972, 296) and f erf-butyl N-(6-bromohexyl)carbamate.

Step Three: To a solution of 16 (1.16 g, 1.29 mmol) in THF (12.9 mL) at room temperature under argon, triphenylphosphine (508 mg, 1.94 mmol) was added. The mixture was stirred for 1.5 hours, water (0.26 mL) was added and stirring w as continued overnight. The mixture was concentrated and the residue was purified by automated chromatography on silica gel (Biotage®, SNAP25 KP-Sil, eluting with 75-100% ethyl acetate in hexanes, then 0-10% methanol with 2% added triethylamine in ethyl acetate, then 10-20% methanol with 2% added triethylamine in dichloromethane) to give 18 (1.101 g) as a brownish yellow viscous oil.

This procedure was also used to prepare 19 from 17.

Step Four: To a solution of 18 (1.10 g, 1.26 mmol) in DMF (6.3 mL) at room temperature under argon, DIPEA (0.66 mL, 3.78 mmol) and diglycolic anhydride (439 mg, 3.78 mmol) were added. The mixture was stirred at room temperature overnight, diluted with ethyl acetate, washed with aqueous HCl (2N), water (3 times), and brine. The organic layer was dried over magnesium sulfate, filtered, and concentrated under reduced pressure. The residue was purified by automated reverse-phase chromatography (Biotage®, SNAP30 C18, eluting with 50-100% acetonitrile in water). Fractions containing 20 were combined, and the acetonitrile was removed by rotary evaporation until a cloudy solution resulted. Enough acetonitrile was added to give a clear solution, which was frozen in a dry ice/acetone bath and lyophilized to give 20 (1.00 g) as a fluffy white powder.

This procedure was also used to prepare 21 from 19, and 29 from 28.

Step Five: To a solution of 20 (580 mg, 0.585 mmol) in DMF (5.9 mL) at room temperature under argon, DIPEA (0.38 mL, 2.19 mmol) and N,N,N',N'-tetramethyl-O—(N-succinimidyl)uronium tetrafluoroborate (TSTU) (283 mg, 0.73 mmol) were added. The resulting mixture was stirred for 1.5 hours, then was cannulated, along with a DMF (0.5 mL) rinse, into a solution of DSPE-PEG$_{3400}$-NH$_2$ (616 mg, approximately 0.146 mmol) in DMF (14.6 mmol) at room temperature under argon. The resulting mixture was stirred for 2.5 days, then was concentrated under reduced pressure. The residue was taken up in toluene and concentrated several times, then was taken up in acetonitrile and water. Acetonitrile was removed by rotary evaporation until slightly cloudy, then acetonitrile was added dropwise until a clear solution resulted. The mixture was frozen in a dry ice/acetone bath and lyophilized. The resulting powder was purified by size exclusion chromatography (Sephadex LH-20) in four portions, eluting with methanol. Individual fractions were spotted on TLC plates (with UV indicator) and visualized by with UV light as well as a phosphomolybdic acid (PMA) stain (10% in ethanol). Material that was both UV and PMA active came off the column in two bands. For the first band, the spots on the TLC plate were very compact with very little spreading beyond the tip of the micropipet spotter. For the second band, the spots were more diffuse, with spreading all the way to the edge of the spotting solvent front. The first band contained the desire product, and fractions from this band were combined and concentrated under reduced pressure to give 22 (690 mg) as a tan-yellow glass.

This procedure was also used to prepare 23 from 21, and 30 from 29.

Step Six: To a solution of 22 (680 mg, approximately 0.13 mmol) in dichloromethane (9 mL), trifluoroacetic acid (9 mL) was added. The mixture was stirred at room temperature for 4 hours, then was concentrated. The residue was dissolved in dichloromethane and concentrated (five times). The residue was then taken up in a 1:1 mixture of acetonitrile and water (30 mL) and allowed to stand overnight. The resulting mixture was diluted with water (60 mL) then the resulting mixture was frozen in a dry ice/acetone bath and lyophilized. The resulting powder was purified by size exclusion chromatography (Sephadex LH-20) in two portions, eluting with methanol. Fractions were spotted as described above and fraction containing material that was both UV and PMA active were combined and concentrated. The residue was taken up in water (50 mL) and acetonitrile (15 mL), the resulting mixture was frozen in a dry ice/acetone bath and lyophilized to give 24 (572 mg) as an off-white solid.

This procedure was also used to prepare 25 from 23, and 31 from 30.

Example 4

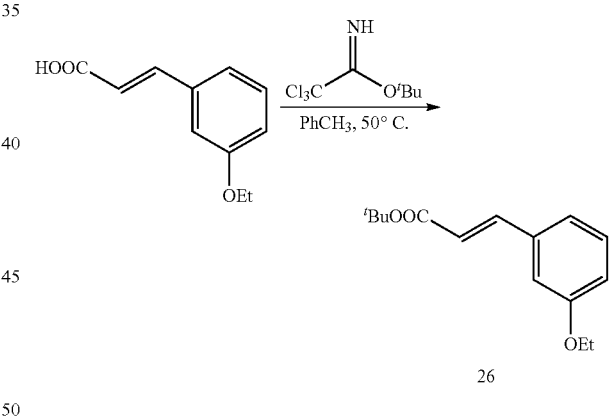

Step One: To a suspension of 3-ethoxycinnamic acid (2.028 g, 10.6 mmol) in toluene (13.3 mL) at room temperature under argon, tert-butyl 2,2,2-trichloroacetimidate (2.37 mL, 13.3 mmol) was added. The mixture was healed to 50° C. overnight, at which time TLC analysis revealed partial conversion. Additional tert-butyl 2,2,2-trichloroacetimidate (1.2 mL) was added and heating was continued for 24 hours. The reaction was still not complete, so more tert-butyl 2,2,2-trichloroacetimidate (1.2 mL) was added and heating was continued for an additional 24 hours. The resulting mixture was filtered, washing with toluene, and the filtrate was concentrated under reduced pressure. The residue was purified by chromatography on silica gel, eluting with 10% ethyl acetate in hexanes to give 26 (2.22 g) as a colorless oil.

Example 5
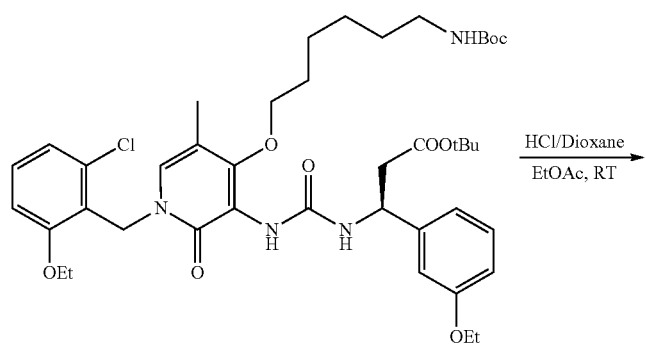
27
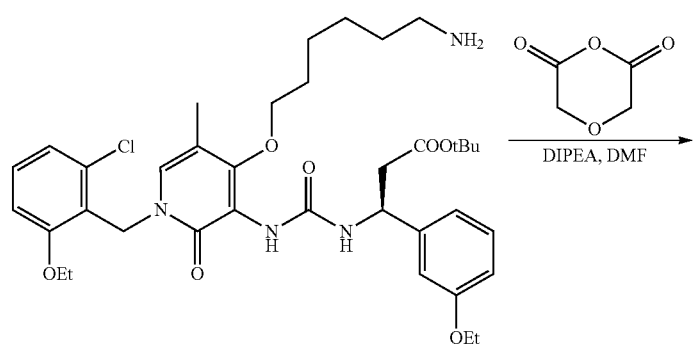
28
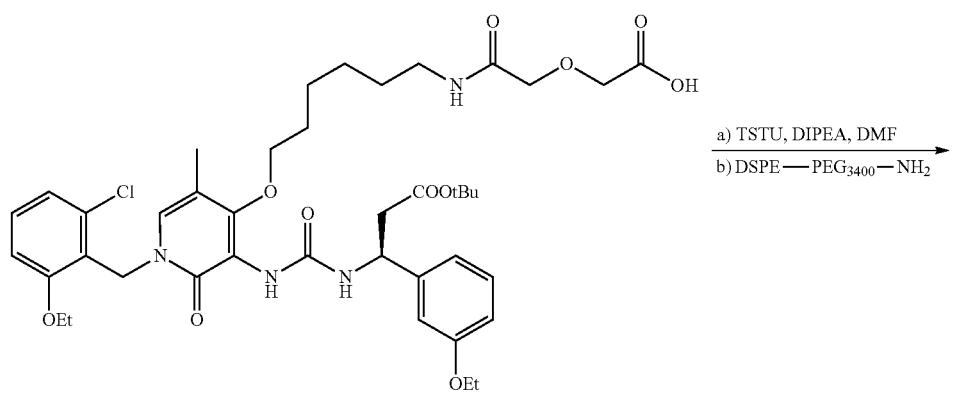
29

-continued

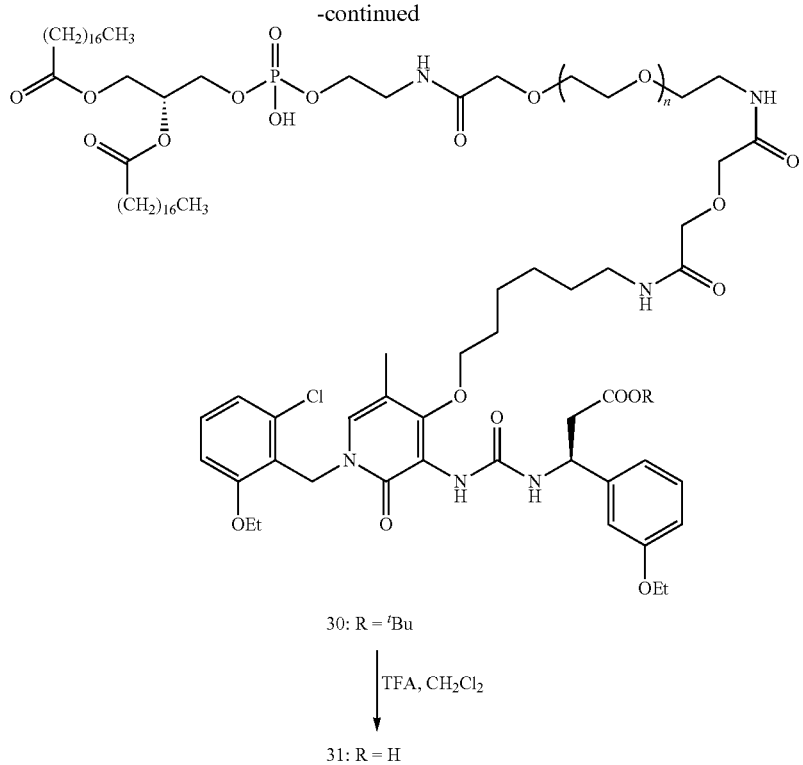

30: R = ⁱBu

↓ TFA, CH₂Cl₂

31: R = H

Step One: To a solution of 27 in ethyl acetate (200 mg, 0.25 mmol) in ethyl acetate (4.0 mL) at room temperature, a solution of hydrogen chloride (4.0 M in dioxane, 1.3 mL, 5.2 mmol) was added. The reaction was stirred for 2 hours, then the excess hydrogen chloride was removed by sparging with argon for 30 minutes. The reaction mixture was concentrated, taken up in water and lyophilized to give a white powder. This material was purified by reverse phase HPLC (Symmetry Shield RP18, 7 μm, 30×250 mm, 30-80% acetonitrile in water with 0.1% trifluoroacetic acid). Fractions containing the desired material were combined, diluted with water and ethyl acetate, made basic with aqueous sodium hydroxide, shaken in a separatory funnel, and the phases separated. The organic layer was washed with water (3 times) and brine, dried over magnesium sulfate, filtered, and concentrated under reduced pressure to give 28 (88 mg) as a colorless oil.

Steps Two to Four: Compound 31 was prepared from 28 following Steps Four to Six of Example 3.

Example 6

Representative Liposome Formulation: 1,2-Dihexadecanoyl-sn-glycero-3-phosphocholine (DPPC) and Cholesterol were purchased from Lipoid Inc., Newark N.J., USA. Diethylenetriaminepentaacetic acid-bis(stearylamide) gadolinium salt (Gd-DTPA-BSA), was purchased from Avanti Polar Lipids, Alabaster Ala., USA. 1,2-Distearoyl-sn-glycero-3-phosphoethanolamine-N-[methoxy(polyethylene glycol)-2000] (DSPE-MPEG2000), was purchased from Corden Pharma, Liestahl, Switzerland. Lissamine™ Rhodamine B 1,2-Dihexadecanoyl-sn-Glycero-3-Phosphoethanolamine, Triethylammonium Salt (rhodamine DHPE), was purchased from ThermoFisher Scientific, USA. All purchased reagents were used without further purification. DSPE-PEG3400-THI565 conjugate was prepared as described in the synthesis protocol above.

Step one: DPPC, Cholesterol, DSPE-MPEG2000, Gd-DTPA-BSA or Gd-DOTA-DSPE and DSPE-PEG3400-THI565 were respectively constituted based on the desired surface targeting ligand expression at molar proportions shown in the following table:

| Surface Ligand (mol %) | DPPC | Cholesterol | DSPE-MPEG2000 | Gd-DTPA-BSA* | DSPE-PEG3400-THI565 (THI567) |
|---|---|---|---|---|---|
| 0.05% | 31.95 | 40 | 3 | 25 | 0.05 |
| 0.25% | 31.75 | 40 | 3 | 25 | 0.25 |
| 1.0% | 31.0 | 40 | 3 | 25 | 1.0 |

*When GD-DTPA-BSA (or Gd-DOTA-DSPE) is not present, the balance may be made with 25% 1,2-distearoyl-sn-glycero-3-phosphoethanolamine (DSPE), HSPC (hydrogenated, soybean phosphatidylcholine), DPPC (Dipalmitoyl Phosphatidylcholine), or HSPC/DPPC (hydrogenated soybean phosphatidylcholine/dipalmitoyl phosphatidylcholine) to maintain the THI567 component constant.

In various embodiments, other suitable Gd chelating agents are included in this disclosure and the use of other suitable Gd chelating agents is also contemplated.

Step two: Optionally, to any of these lipid compositions was added rhodamine DHPE (1.0 to 2.5 mg), iodine contrast agent (e.g. iodixanol) or bioactive agent and particle formulation as previously described in Ghaghada K B, Ravoori M, Sabapathy D, Bankson J, Kundra V, Annapragada A. New Dual Mode Gadolinium Nanoparticle Contrast Agent for Magnetic Resonance Imaging. Yang S, editor. PLoS ONE. 2009 Oct. 29; 4(10):e7628. Briefly, the lipids (467.4 mgs) were dissolved in ethanol (1.0 to 1.2 mL) followed by hydration at 63-65° C. for 40 minutes in 150 mM saline/10 mM histidine (9 mLs) to achieve a lipid concentration of 50 mM. The mixture was then extruded in a 10 ml Lipex extruder (Northern Lipids Inc., Burnaby, Canada) using a 400 nm polycarbonate track-etch filter (5 passes), to obtain particles with a mean diameter of ~250 nm. For particles with mean diameter of ~150 nm, the ensuing formulation was further extruded through a 200 nm polycarbonate filter (8 passes), and for particles with a mean diameter of ~100 nm, the formulation was further extruded (5 times) through 100 nm filters. The resulting solutions was then dialyzed against 150 mM saline/10 mM histidine. The mean liposome size in the final formulation was determined by dynamic light scattering (DLS), and the gadolinium and phospholipid (equivalent phosphorus) concentration in the formulation, quantified using inductively coupled plasma optical emission spectroscopy (ICP-OES). The number of particles/mL was computed based on the particle size and the final lipid concentration in the formulation.

In this disclosure, a liposome incorporated with the integrin targeting a molecule (THI567) is shown to specifically bind T-cells, B-cells, monocytes, and neutrophils. In various embodiments, liposomes modified by the targeting agent of this disclosure (e.g., THI567) are able to bind to both non-activated and activated cells. In addition, this molecule (THI567) has a lipid anchor that allows it to be inserted into a lipid bilayer in a liposome. Furthermore, the molecule (THI567) has a unique hydrophilic character, preventing it from disrupting the lipid bilayer. The molecule is therefore particularly well suited to specifically deliver liposomes to target cells. Liposomes modified with/by or carrying this molecule on the surface could bear imaging agents, for the purpose of imaging/tracking the cells and also bear therapeutic agents that could be delivered to target cells highly specifically.

Preparation of iodine containing VLA-4 targeted CT contrast agent. Another Targeted liposome was prepared by dissolving lipids (HSPC/DPPC, Choi, DSPE-mPEG2000, DSPE-PEG3400-THI0565) in ethanol. The ethanolic lipid solution was hydrated with iodixanol solution and sequentially extruded through Nucleopore membranes to yield nanoparticles of desired particle size. The resulting nanoparticle solution was diafiltered to remove unencapsulated iodixanol. Rhodamine-DHPE may be included at 0.2 mol % for preparation of fluorescent-tagged nanoprobe. We have prepared targeted particles containing 0.25-1.5 mol % targeting ligand, and particle size from 100-300 nm. HSPC is hydrogenated soybean phosphatidylcholine in place of DSPE.

Representative Bioactive Preparation: Preparation of VLA-4 targeted Liposomal-doxorubicin. Lipids (HSPC, Choi, DSPE-mPEG2000, DSPE-PEG3400-THI0565) are dissolved in ethanol at molar ratio 56:40:3:1. The ethanolic lipid solution is hydrated with 350 mM ammonium sulfate solution and sequentially extruded through Nucleopore membranes with 5 passes through 400 nm and 8 passes through 200 nm. The resulting liposomal solution is dialyzed against 150 mM saline/10 mM histidine. The liposomal solution is mixed (1:1 V/V) with doxorubicin solution (5 mg/mL) at 60 C. After 1 hour, the solution is cooled in ice bath and subsequently dialyzed against 150 mM saline/10 mM histidine.

In this disclosure, the use of integrin α4β1 targeting ligand coupled to liposomes to image autoimmune or inflammatory cell foci is discussed. This methodology, for example, may be used to image atherosclerotic plaques, transplant rejection, joint inflammation in rheumatoid arthritis, lung inflammation in acute lung injury, α4β1 expressing tumors such as those found in lymphoma, and immune cell infiltration in solid tumors. Furthermore, drug treatments for these disease states using this delivery methodology are also contemplated.

The targeting molecule/moiety of this disclosure is distinct from and advantageous over those in the art because it has a unique hydrophilic character and lipid anchors that make it suitable for incorporation into a lipid bilayer, providing stable, active liposomes that are able to specifically bind the target cells.

TABLE 1

Compound structures.

| Compound Number | Structure | Activity (IC$_{50}$) Cell Type | Substrate | Cations | Species | General Notes |
|---|---|---|---|---|---|---|
| THI520 | [structure: chlorobenzyl-ethoxy pyridinone with CH$_3$, ONa, urea linkage, CO$_2$Na, ethoxyphenyl group] | 0.11 ± 0.04 nM (n = 2) K562(α4β1) | CS-1 | Mn | Human | α4β1 antagonist not conjugated with lipid anchoring group. cLogP −4.165 |
| | | 6.3 ± 3.1 nM (n = 3) K562(α4β1) | VCAM-1 | Ca/Mg | Human | |
| | | 129 ± 42 nM (n = 3) 70Z3 | VCAM-1 | Ca/Mg | Mouse | |
| | | 0.75 ± 0.07 nM (n = 2) 70Z3 | VCAM-1 | Mn | Mouse | |

TABLE 1-continued

Compound structures.

| Compound Number | Structure | Activity (IC$_{50}$) Cell Type | Substrate | Cations | Species | General Notes |
|---|---|---|---|---|---|---|
| THI565 | (structure shown) | 0.467 ± 0.356 nM (n = 13) K562(α4β1) | VCAM-1 | Mn | Human | α4β1 antagonist not conjugated with lipid anchoring group cLogP −1.361 Lower lipophilicity than THI520 suggests better performance in liposome constructs. |
|  |  | 11.88 ± 4.84 nM (n = 3) K562(α4β1) | VCAM-1 | Ca/Mg | Human |  |
|  |  | 0.320 ± 0.113 nM (n = 3) K562(α4β1) | CS-1 | Mn | Human |  |
|  |  | 7.94 ± 3.7 nM (n = 3) K562(α4β1) | CS-1 | Ca/Mg | Human |  |
| THI567* | (structure shown) | 0.62 ± 0.11 nM (n = 3) K562(α4β1) | VCAM-1 | Mn | Human | THI565 conjugated with lipid anchoring group and hydrophilic linker for incorporation into liposomes. |

*Structure represents the mean target molecular weight across the distribution of compounds represented in the sample.

Figure 2:
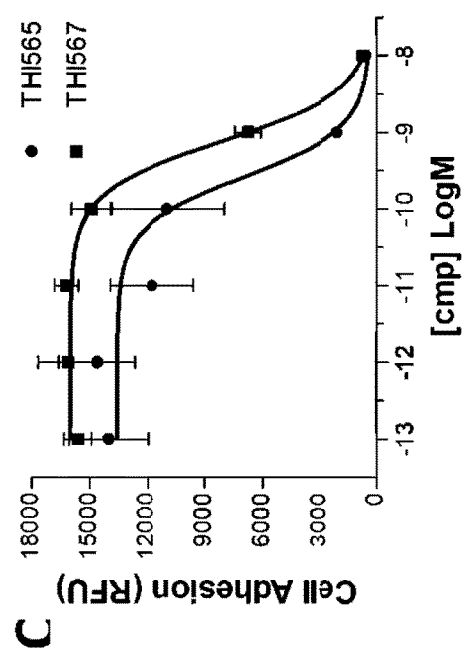
FIG. 2 illustrates the structure of THI565 and attachment of the linker and lipid anchor THI567 for liposome development. Structure of THI565 is shown in FIG. 2A and structure of THI567 is shown in FIG. 2B.
Figure 2:
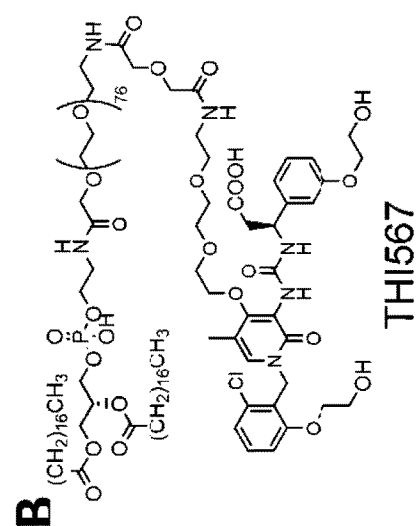
Figure 2:
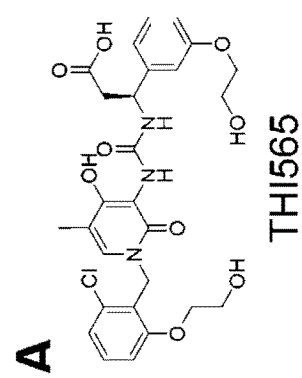

We have generated targeted nanoparticles based on the integrin α4β1 antagonist THI565 as the targeting ligand (see Table 1 for structure). This inhibitor is a potent antagonist of integrin α4β1 under both high affinity (0.467±0356 nM; n=13) and low affinity (11.88±4.84 nM; n=3) cell adhesion assay conditions and has a cLogP preferred over THI520 for liposome incorporation. Modification of THI565 with a linker (DSPE-PEG-3400-NH) designed to be incorporated into liposomes did not significantly affect antagonist activity (THI567 IC$_{50}$=0.48±0.2 nM; n=5). FIG. 2 describes these two compounds.

THI567 was used in the generation of a variety of different liposome formulations (See Table 2).

TABLE 2

Liposome formulations.

| Particle Size (nm) | Est. Particles/mL [M] | Estimated Surface Ligands/particle | Surface Ligand Concentration | Kd (av); SEM [pM] n = 3 |
|---|---|---|---|---|
| THI567 - 0.05% (percentage of targeted ligand) | | | | |
| 250 | 3.21 × 10$^{13}$ 5.33 × 10$^{-8}$ M | 242 | 12.9 μM | 398.6 +/− 78.2 |
| 150 | 6.81 × 10$^{13}$ 1.13 × 10$^{-7}$ M | 116 | 13.1 μM | 567.6 +/− 32.8 |
| 100 | 1.35 × 10$^{14}$ 2.24 × 10$^{-7}$ M | 60 | 13.5 μM | 474.5 +/− 62.3 |
| THI567 - 0.25% (percentage of targeted ligand) | | | | |
| 250 | 3.88 × 10$^{13}$ 6.44 × 10$^{-8}$ M | 1006 | 64.8 μM | 294.9 +/− 33.1 |
| 150 | 7.20 × 10$^{13}$ 1.20 × 10$^{-7}$ M | 549 | 65.7 μM | 303.6 +/− 70.0 |
| 100 | 1.76 × 10$^{14}$ 2.92 × 10$^{-7}$ M | 231 | 67.5 μM | 309.0 +/− 57.6 |
| THI567 - 1.0% (percentage of targeted ligand) | | | | |
| 250 | 3.06 × 10$^{13}$ 5.08 × 10$^{-8}$ M | 5075 | 258.0 μM | 174 +/− 21.5 |

TABLE 2-continued

Liposome formulations.

| Particle Size (nm) | Est. Particles/mL [M] | Estimated Surface Ligands/particle | Surface Ligand Concentration | Kd (av); SEM [pM] n = 3 |
|---|---|---|---|---|
| 150 | $6.21 \times 10^{13}$ $1.03 \times 10^{-7}$ M | 2535 | 261.5 µM | 236.3 +/− 36.0 |
| 100 | $1.15 \times 10^{14}$ $1.91 \times 10^{-7}$ M | 1397 | 266.9 µM | 247.5 +/− 41.2 |

Figure 3:
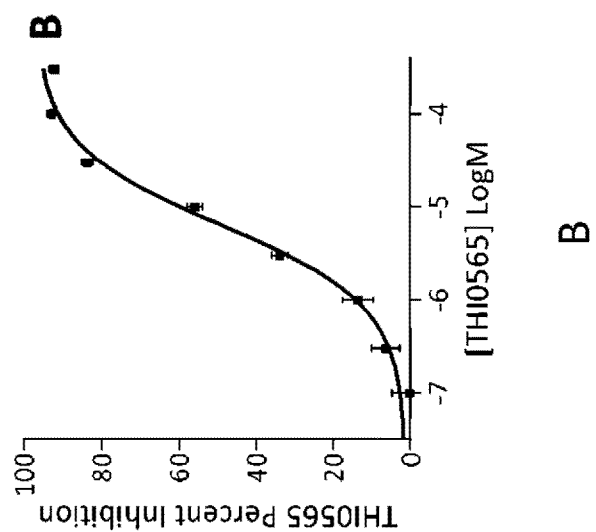
FIG. 3 shows THI565 inhibition of THI567-targeted liposome (150 nm; 1.0%) binding to α4β1-K562 cells. THI567-targeted liposome (150 nm; 1.0%) was used at a concentration of $2 \times 10^{-10}$ pM, and THI565 was used at indicated concentrations. Rhodamine fluorescence was detected by flow cytometry.
Figure 3:
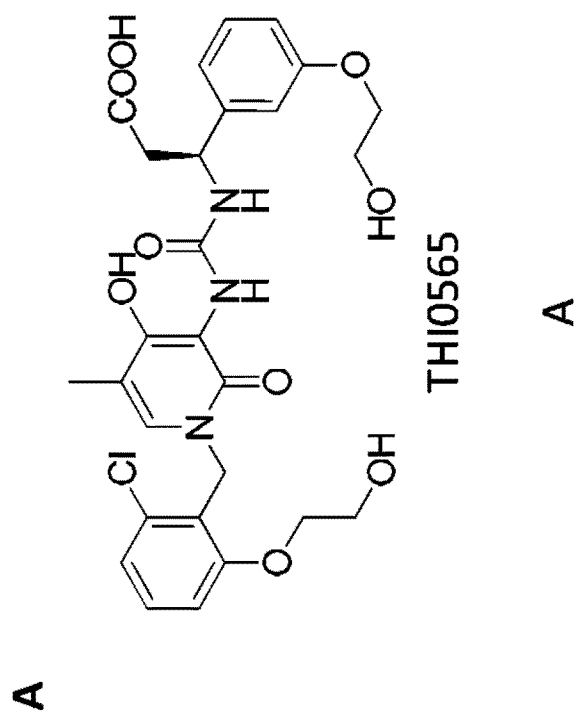

As summarized in Table 2, THI567 was incorporated from concentrations ranging from 0.05% total lipid concentration, to up to 1% total lipid concentration. Particle size is a critical component for acceptable functionality and pharmacokinetics of the liposome in vivo. In an embodiment, the particle size is between 50 and 400 nm. In an embodiment, the particle size is between 85 and 200 nm. In another embodiment, different liposome sizes were developed (250 nm, 150 nm, and 100 nm). Lissamine rhodamine B was incorporated into the liposomes for fluorescence detection, and Gd was incorporated into liposome for MRI-based imaging. Liposomes were termed "$Gd_{567}$" (size nm; % targeted ligand). Table 2 also describes liposome binding constants as measured by their binding to α4β1 expressing K562 cells (measured by flow cytometry). Binding constants are expressed as the molar particle concentration. Binding specificity of liposomes was determined by a number of different means. These include competition with free targeting ligand (FIG. 3), where excess THI565 was used to compete binding of $Gd_{567}$ (150 nm; 1.0%) liposome to integrin α4β1 expressing K562 cells. Complete inhibition of $Gd_{567}$ (150 nm; 1.0%) binding was observed at the highest doses of THI0565 (FIG. 3).

Figure 4:
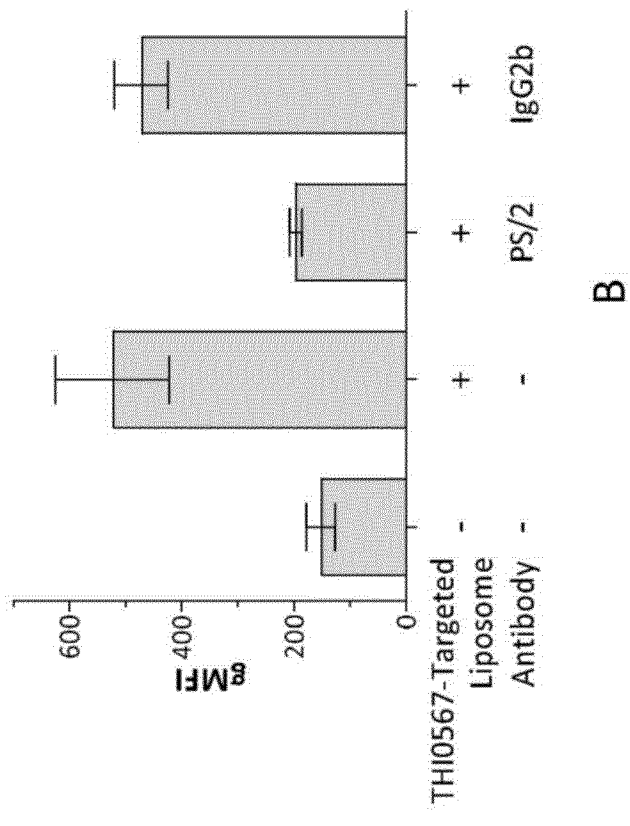
Figure 4:
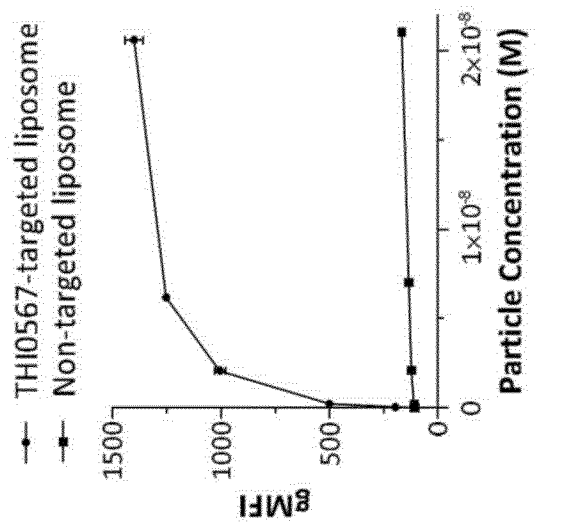

In another set of experiments, non-targeted liposomes (which have 3% inert DSPE-PEG-2000-OMe surface coating for stealth properties while the targeted liposome has 3% DSPE-PEG-2000-OMe and 1% DSPE-PEG-3400-THI565 (termed THI567)) showed minimal binding at the concentrations tested, whereas THI567-targeted liposomes demonstrated dose-dependent binding (FIG. 4). Also, monoclonal antibodies were used to inhibit $Gd_{56}7$ (ISO nm; 1.0%) binding to the murine cell line 70273. Antibodies specific to murine a4 integrin (mAb PS/2), completely inhibited binding of $Gd_{567}$ (ISO nm; 1.0%) to 70273 cells, whereas the isotype control mAb (rat IgG2b) had no effect (FIG. 4). This demonstrates specific binding of $Gd_{567}$ (150 nm; 1.0%) to the integrin α4β1.

Figure 5:
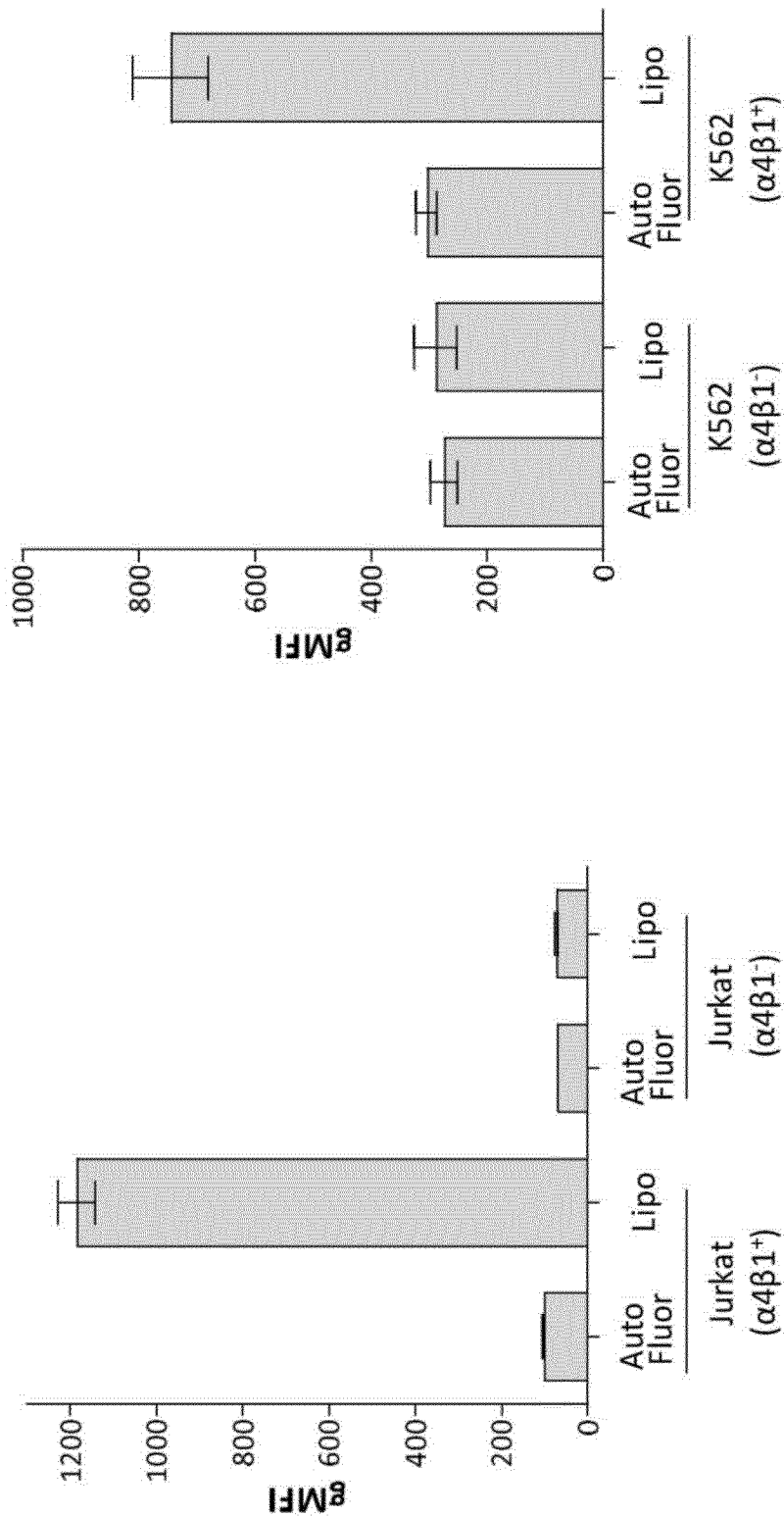
FIG. 5 illustrates THI567-targeted liposomes (150 nm; 1.0%) binding to Jurkat and K562 cells engineered to differentially express integrin α4β1. THI567-targeted liposomes (150 nm; 1.0%) was used at a concentration of $2\times10^{-10}$ pM. Rhodamine fluorescence was detected by flow cytometry.

Further testing of liposome binding specificity took advantage of cell lines that have been engineered to either express integrin α4β1, or cell lines that have been mutated and selected for loss of expression of integrin α4β1. Wild-type K562 cells express little to no integrin α4β1. When used in binding assays with $Gd_{567}$ (ISO nm; 1.0%), there was little binding of liposome to this cell as compared to K562 cells that have been engineered to over-express integrin α4β1 (FIG. 5). Jurkat cells express integrin α4β1. Ceils were mutated and selected for loss of integrin α4β1. Binding of $Gd_{567}$ (ISO nm; 1.0%) to α4β1 expressing Jurkats was detected, with no binding to α4β1⁻ Jurkat cells observed (FIG. 5).

Integrin cell adhesion receptors require divalent cations for their ligand binding activity. Thus, in another experiment designed to demonstrate specificity of liposome binding, EDTA was used in the binding assay to chelate cations and inhibit integrin function. EDTA completely abrogated $Gd_{567}$ (250 nm; 0.05%) binding to Jurkat T lymphocytes even at high concentrations of tested liposome (FIG. 6).

Figure 6A:
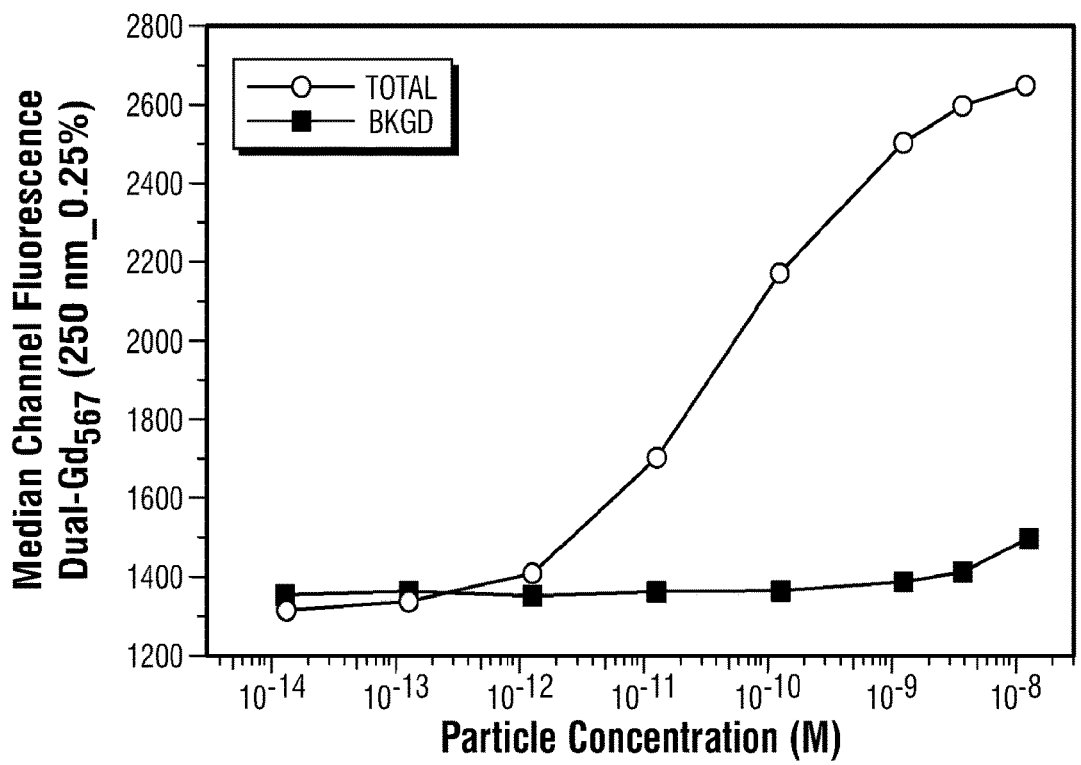
FIG. 6 illustrates THI567-targeted liposome (250 nm; 0.25%) binding to Jurkat cells that express integrin α4β1. THI567-targeted liposome (250 nm; 0.25%) was used at indicated concentrations, and background fluorescence (Bkgd) was determined in the presence of THI567-targeted liposomes and 20 mM EDTA. Rhodamine fluorescence was detected by flow cytometry and presented as geometric mean fluorescence intensity (gMFI).
Figure 6B:
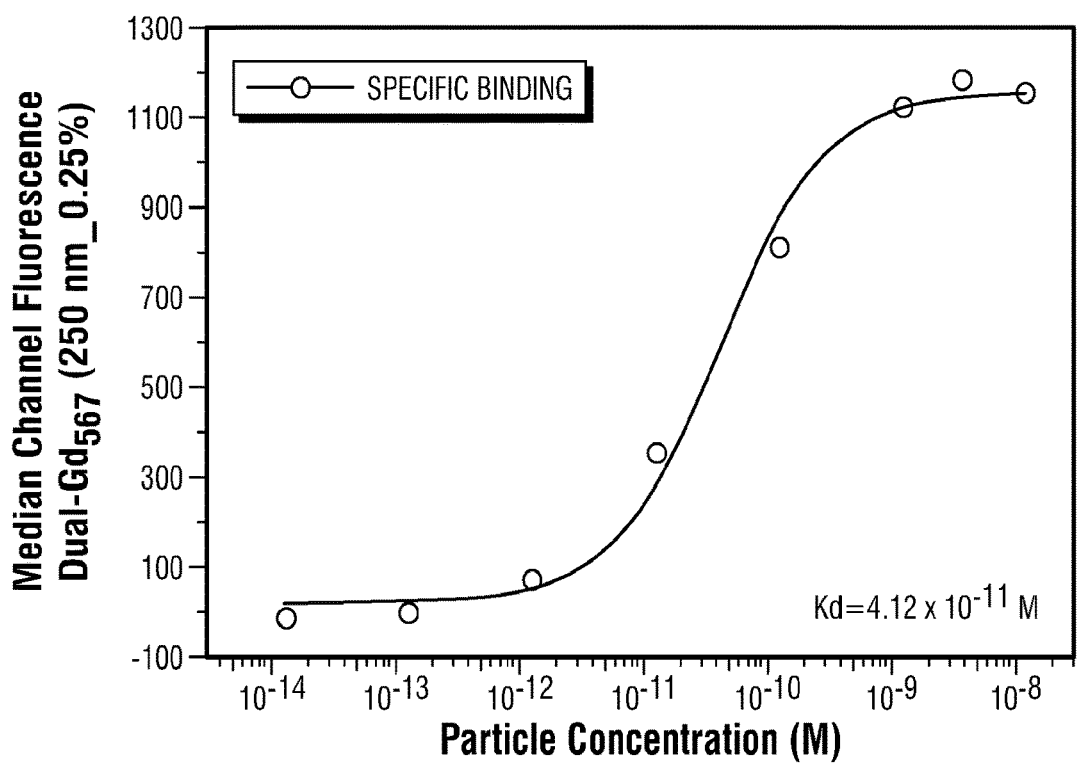
Figure 7A:
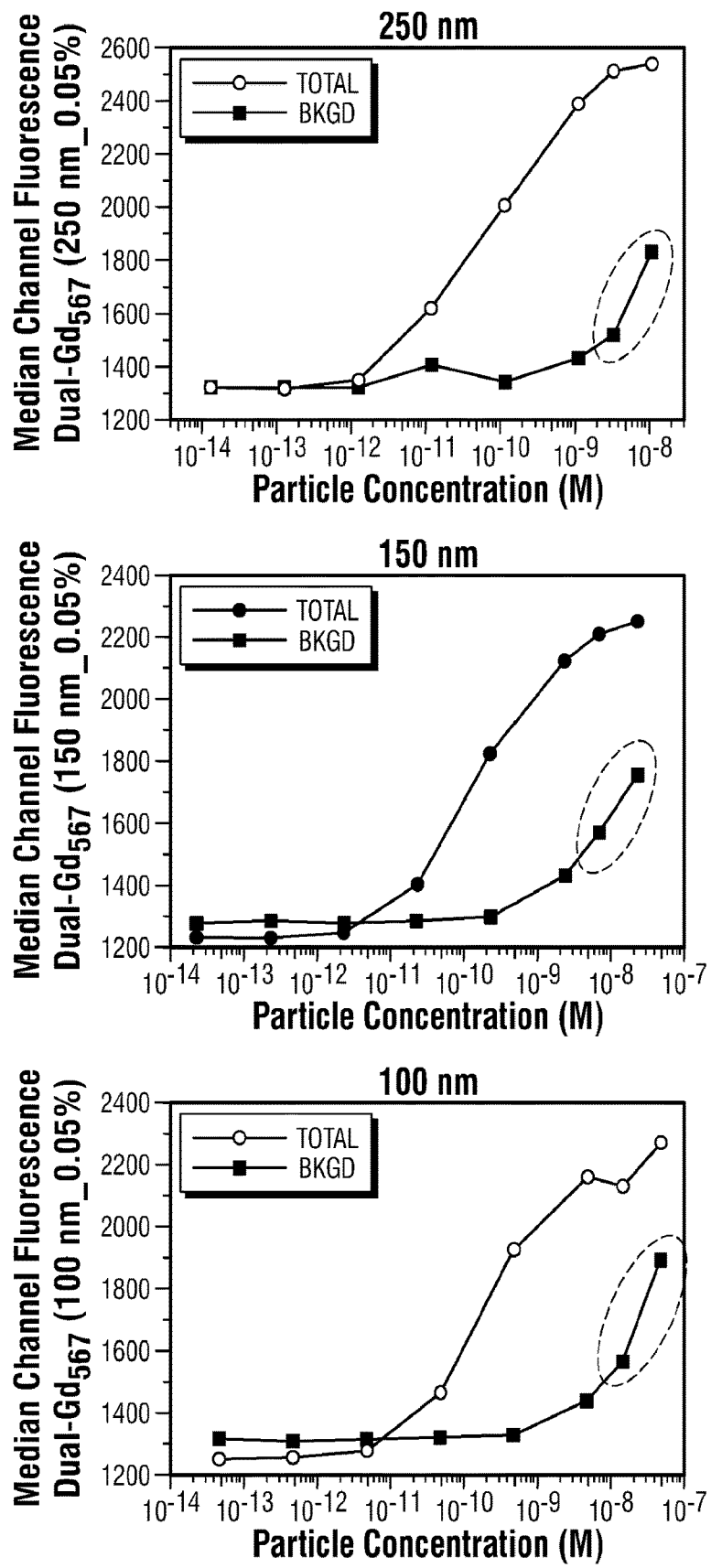
FIG. 7 illustrates a matrix of different sized and targeted-ligand concentrations of THI567-targeted liposome binding to Jurkat cells that express integrin α4β1. THI567-targeted liposome (250 nm; 0.25%) was used at indicated concentrations, and background fluorescence (Bkgd) was determined in the presence of THI567-targeted liposomes and 20 mM EDTA. Rhodamine fluorescence was detected by flow cytometry and presented as geometric mean fluorescence intensity (gMFI).
Figure 7B:
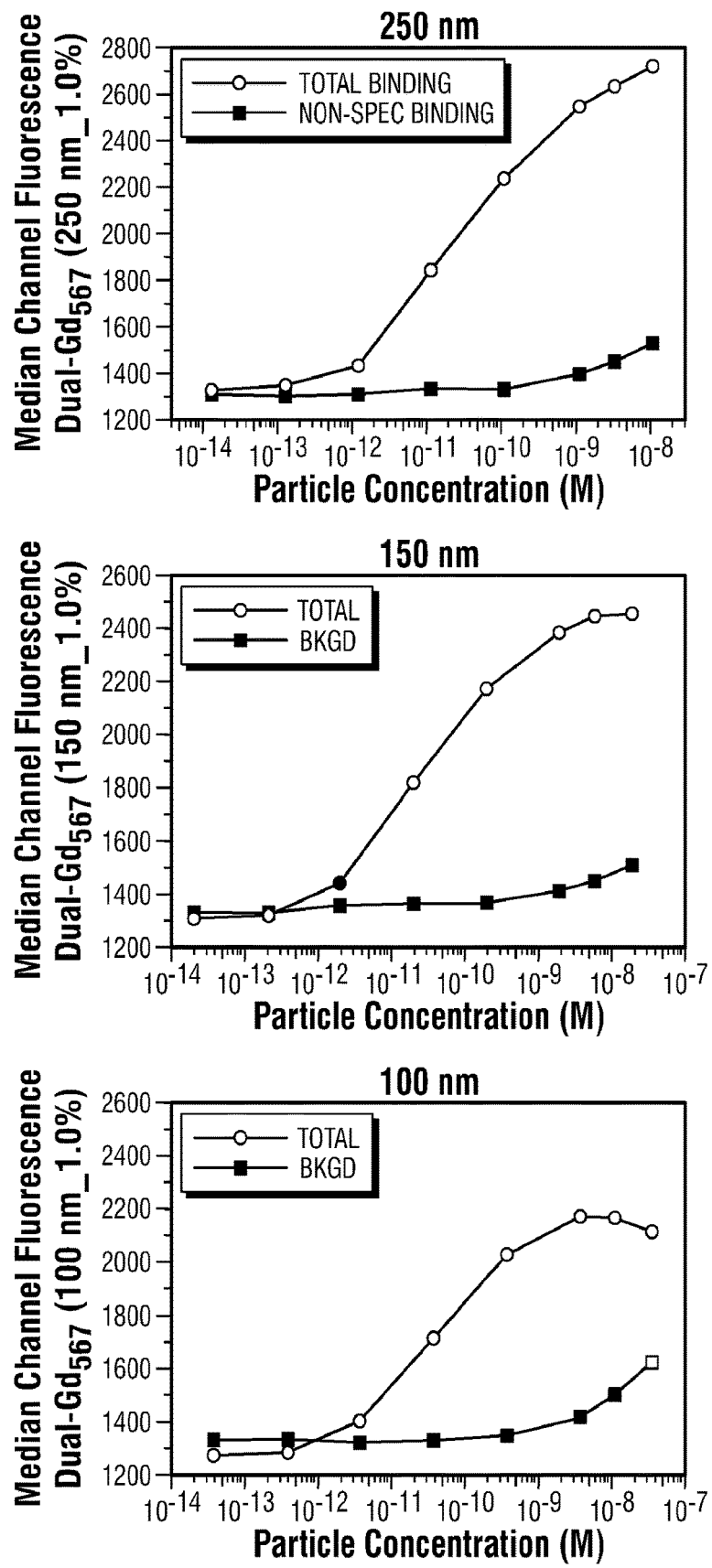
Figure 8A:
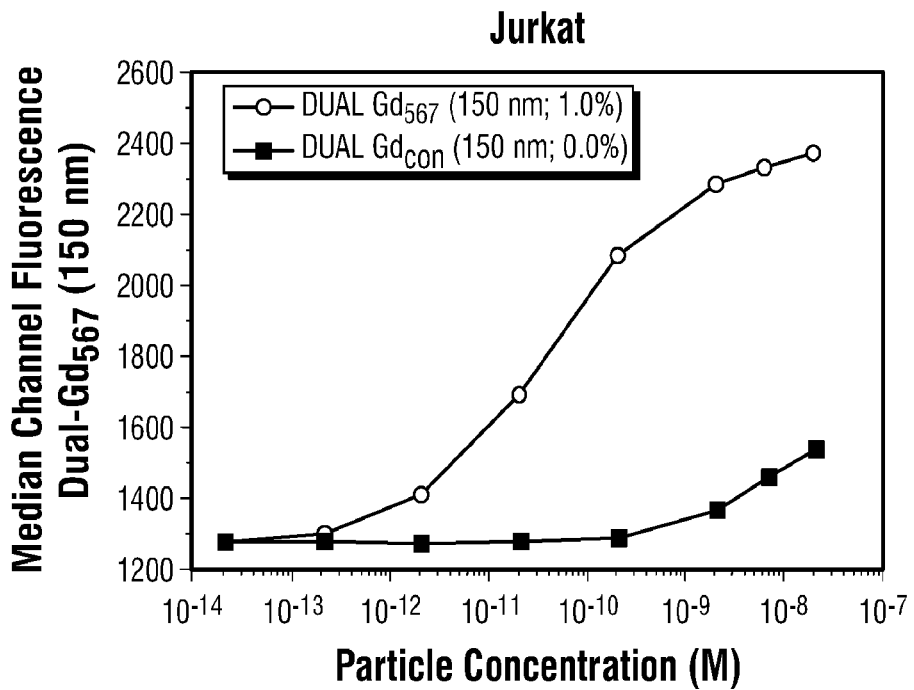
FIG. 8 illustrates specific THI567-targeted liposome binding to lymphocyte subsets. THI567-targeted and non-targeted liposomes were injected (femoral vein) 2 hours prior to whole blood collection by heart puncture. Peripheral blood subsets were identified with FITC-CD11b (monocytes), FITC-Ly-6G (neutrophils), Cy5-CD19 (B cells), and Cy5-CD3 (T cells), and liposome fluorescence (Rhodamine B) in each subset was quantified by flow cytometry. An average±SEM of three independent experiments is shown.
Figure 8B:
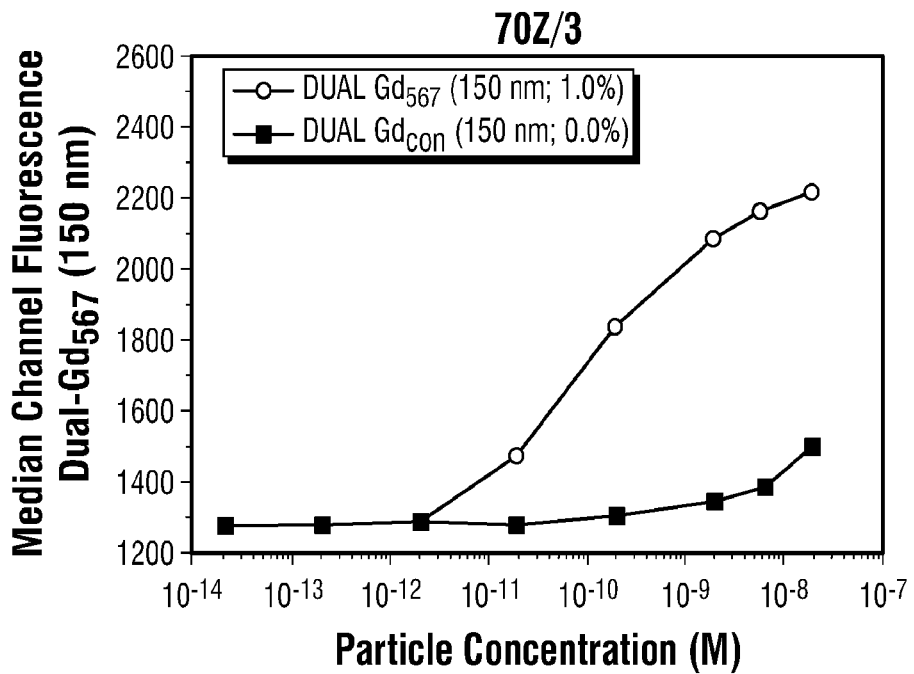
Figure 6:
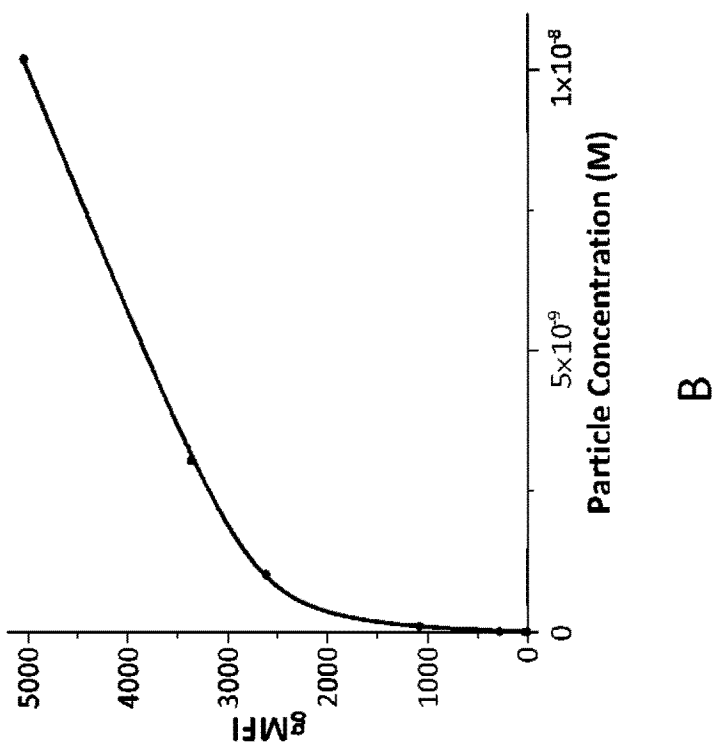
Figure 6:
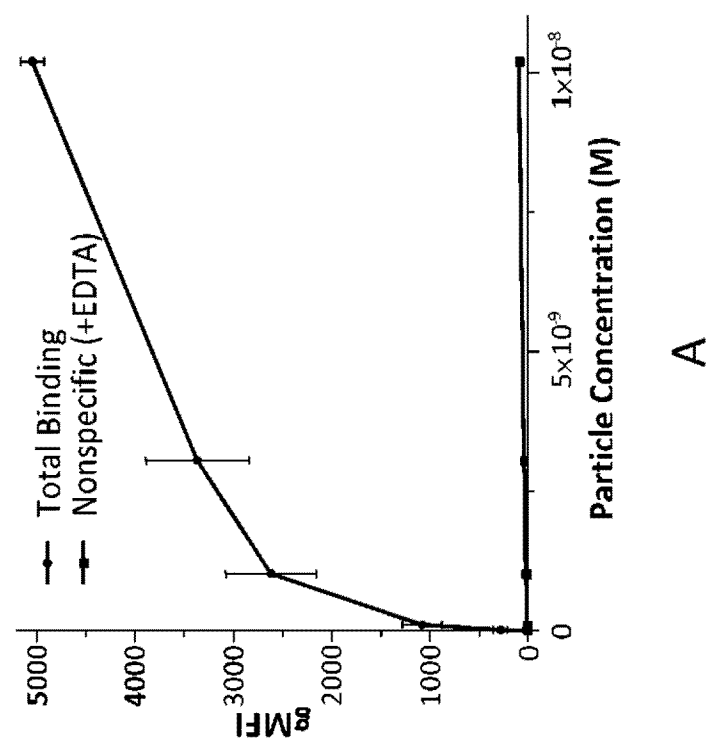
Figure 7:
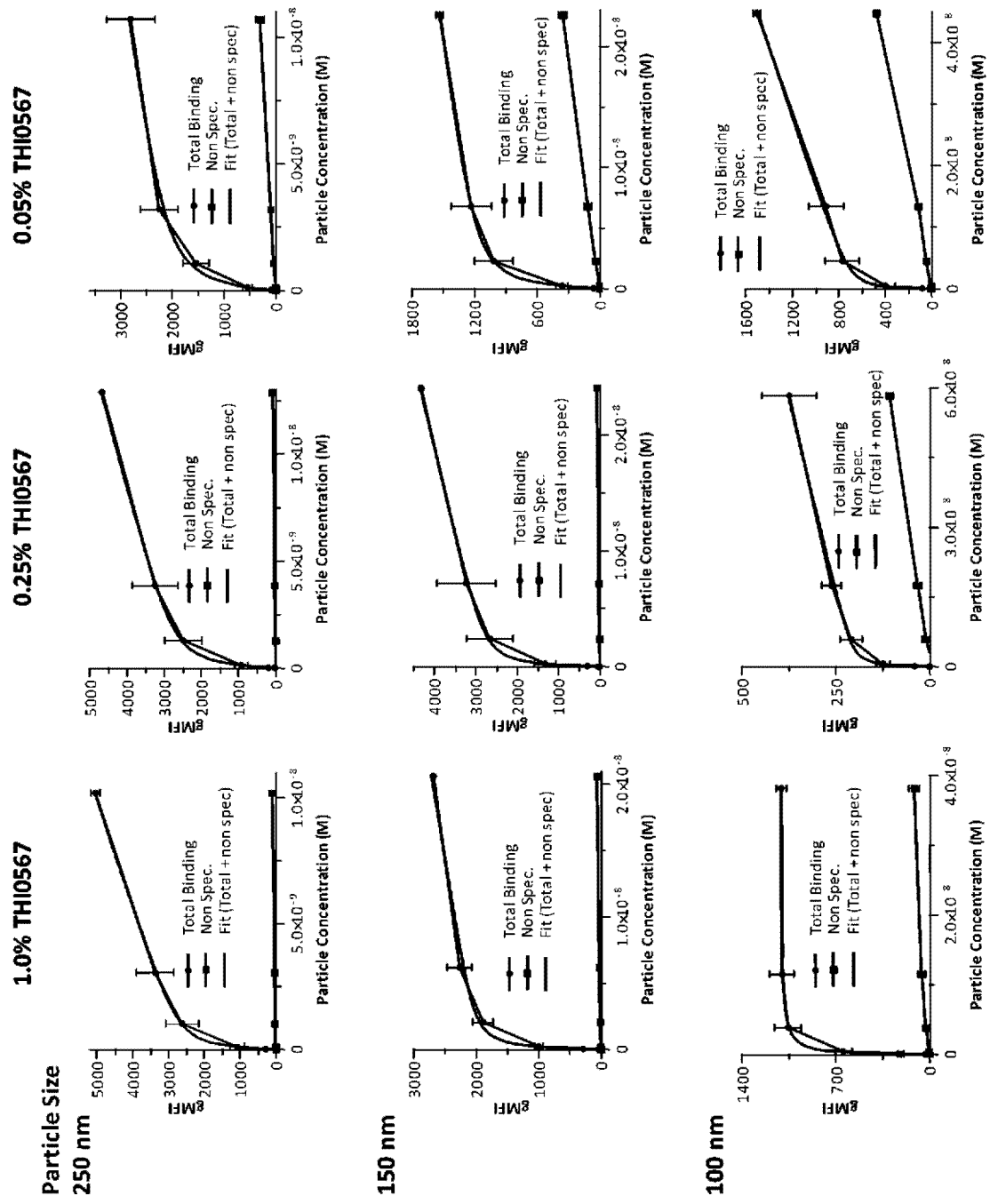

All of the different liposome formulations described in Table 2 were subjected to the analysis performed in FIG. 6. As shown, background fluorescence was determined in the presence of 20 mM EDTA to inhibit integrin function. This background fluorescence was subtracted from the total binding to determine specific binding curves, from which apparent Kd's were determined. Kd's ranged from 22.0-100.5× $10^{-12}$ M (sec Table 2). It was also observed that lower amounts of targeting ligand (e.g. 0.05%) resulted in higher background liposome binding to cells, thus indicating that higher concentrations of targeted ligand in the liposomes would be optimal for specific cell binding (FIG. 7).

From the matrix of liposomes described in Table 2, $Gd_{567}$ (150 nm; 1.0%) was chosen for further in vivo analysis based on the observed Kd and decreased non-specific binding. Also, as another test of binding specificity, control liposome of the same physico-chemical parameters of $Gd_{567}$ (150 nm; 1.0%) were generated without the targeting ligand. These non-targeted particles ($Gd_{con}$ (150 nm; 1.0%)) have 3% inert DSPE-PEG-2000-OMe surface coating for stealth properties while the labeled liposome has 3% DSPE-PEG-2000-OMe and 1% DSPE-PEG-3400-THI565 (termed THI567). A Representative binding assay is shown (FIG. 4).

To analyze binding in vivo, $Gd_{567}$ (150 nm; 1.0%) or $Gd_{con}$ (150 nm; 1.0%) were injected into the femoral vein of healthy C57BL/6 mice. After 2 h, whole blood was collected by heart puncture, and liposome binding to peripheral blood monocytes, neutrophils, T cells, and B cells were analyzed (FIG. 8).

Figure 8:
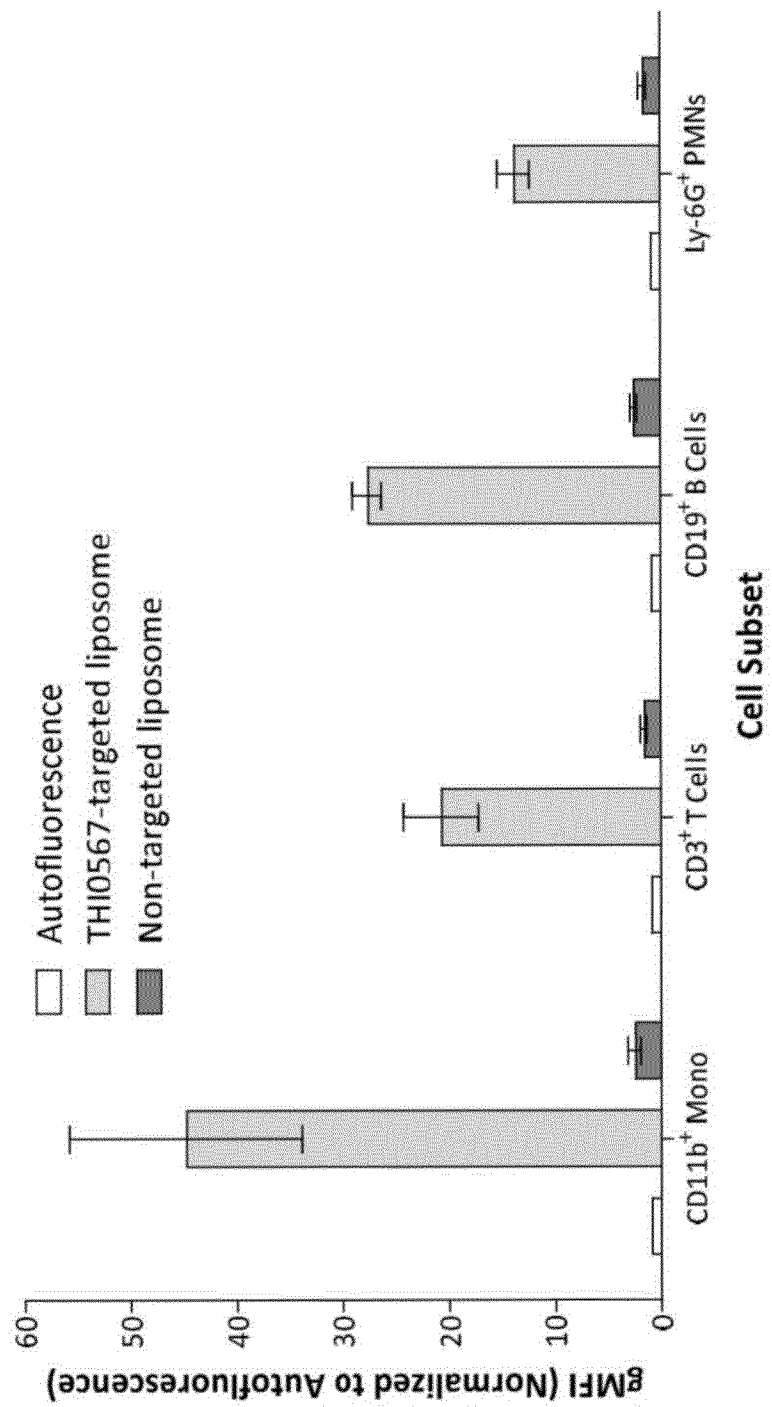
Figure 9:
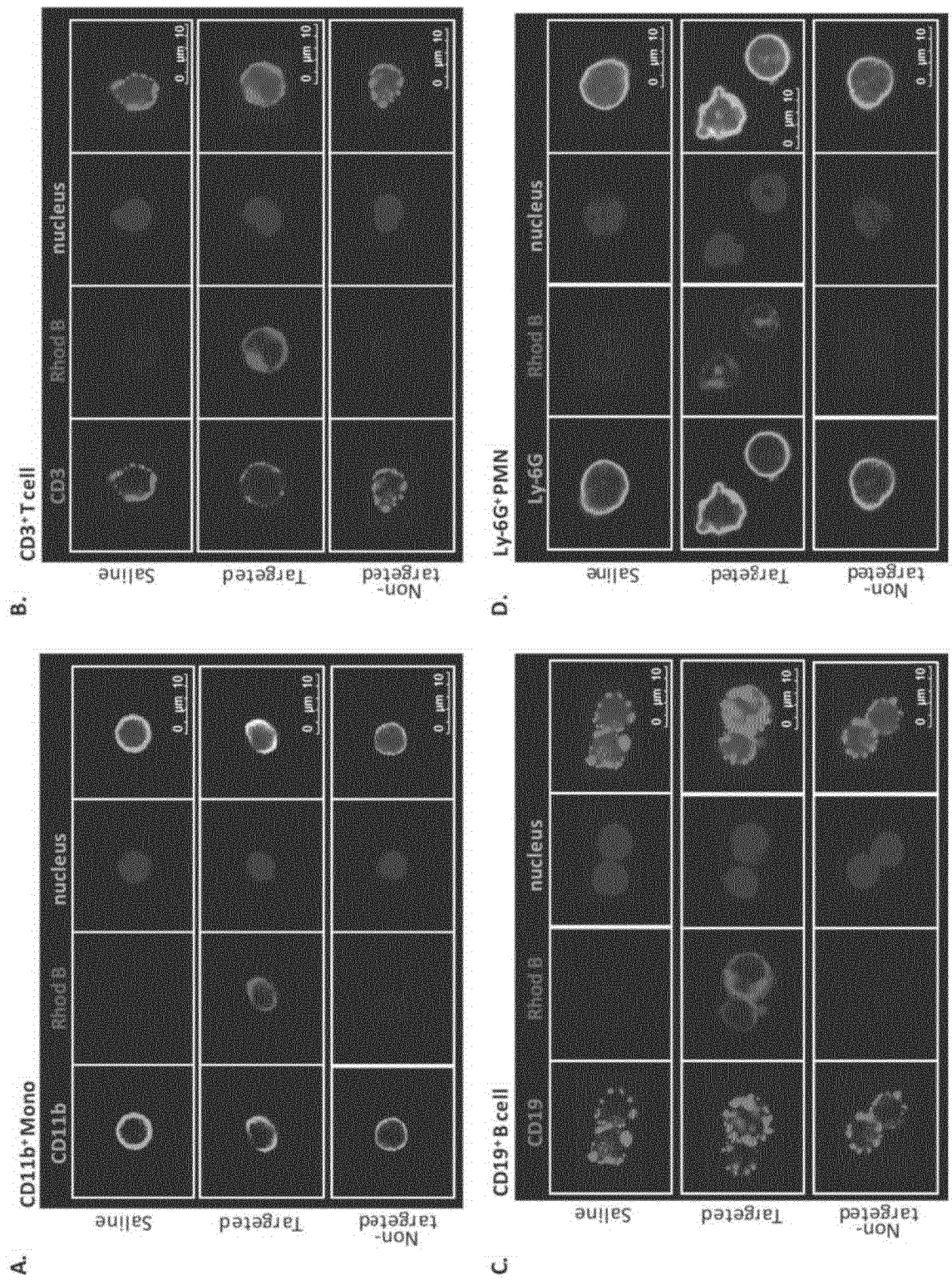
Figure 10:
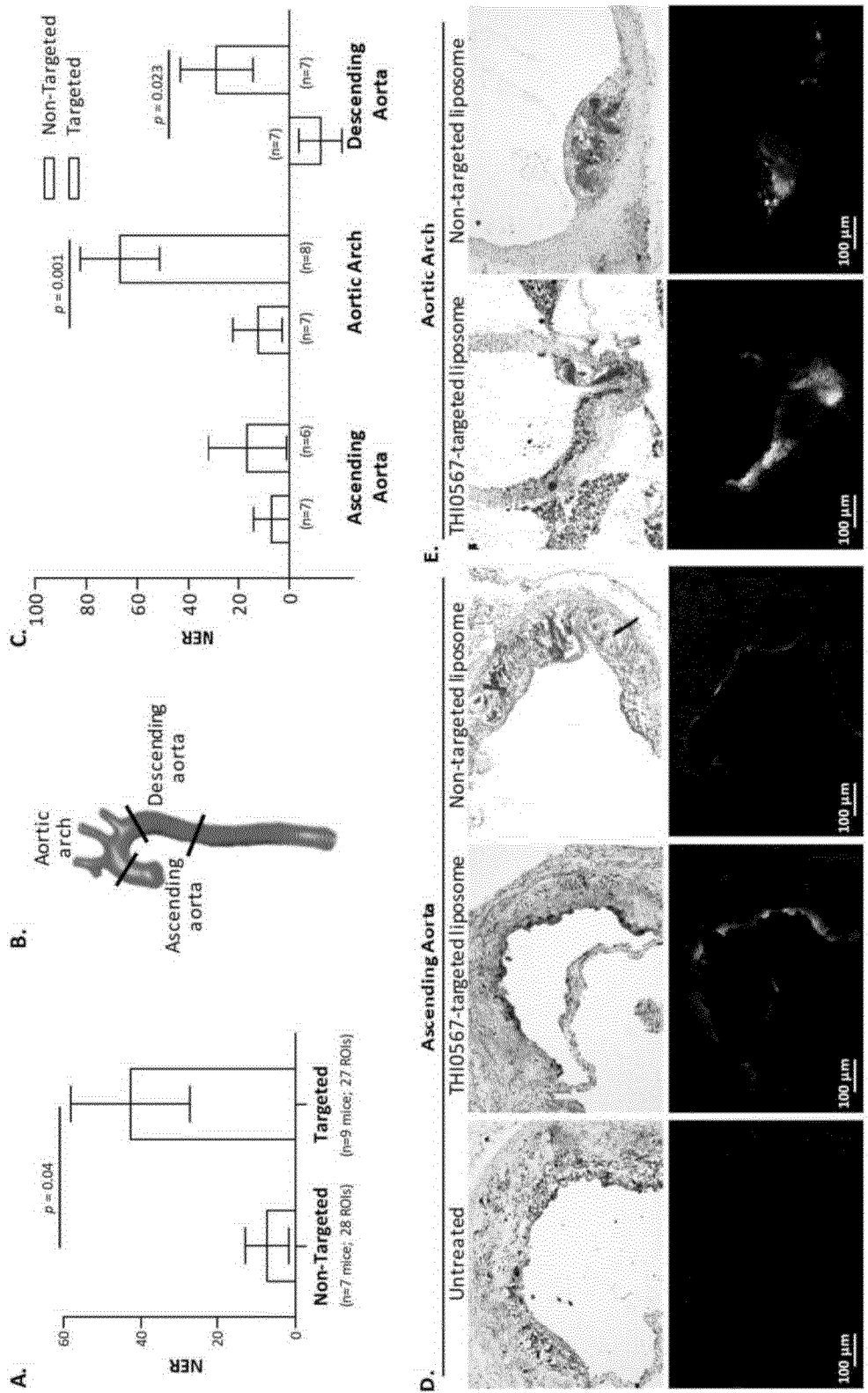

Similarly to the in vitro studies described in FIG. 4, binding of Gd567 (150 nm; 1.0%) was detected, whereas no significant binding of $Gd_{con}$ was observed in vivo (FIG. 8). A summary of three independent experiments (average normalized fluorescence intensity±SEM) is shown in FIG. 8.

Figure 9:
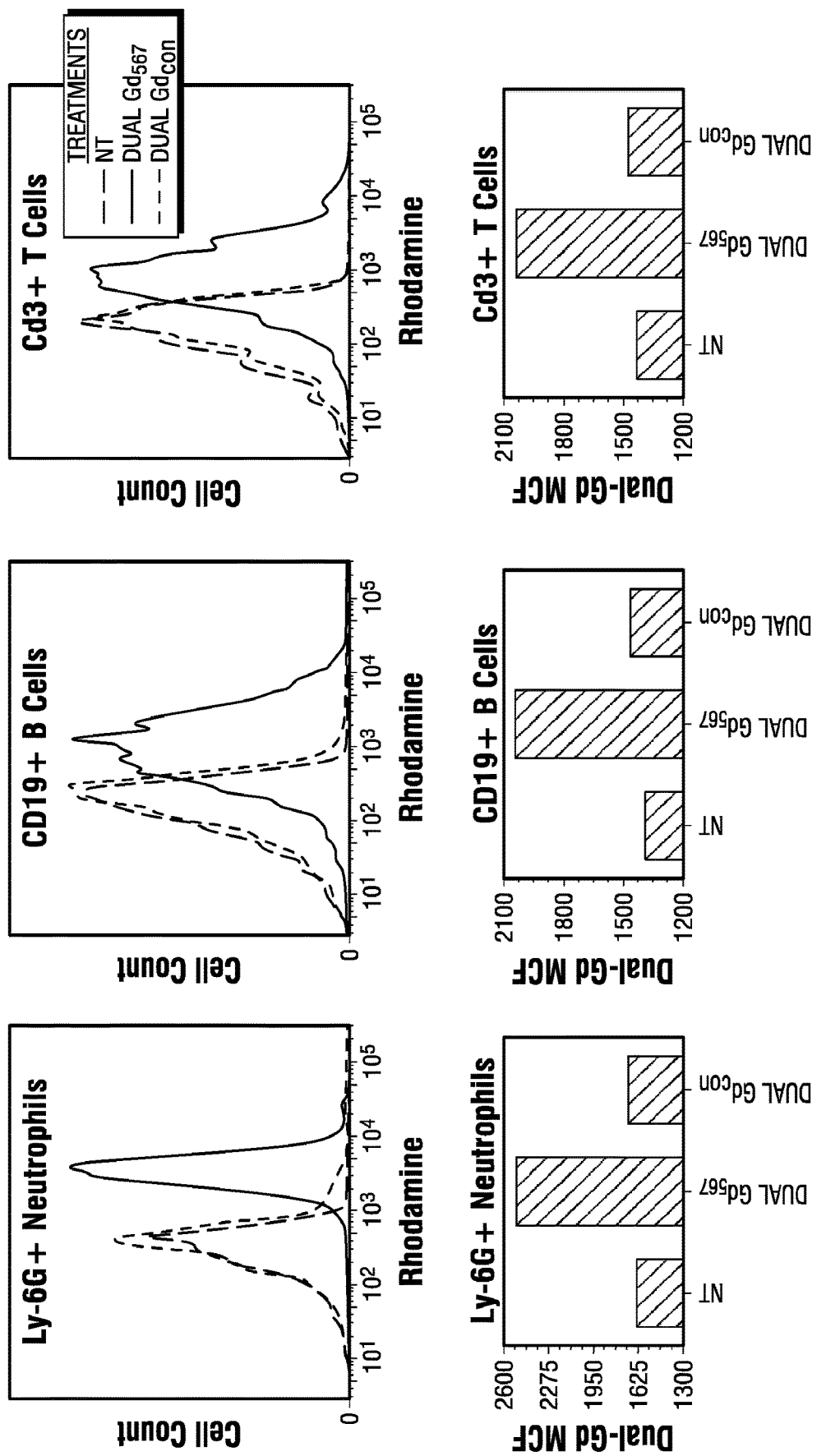
FIG. 9 illustrates THI567-targeted and non-targeted liposome uptake in lymphocyte subsets as imaged with confocal microscopy. Liposomes were injected into C57BL/6 mice (femoral vein) 2 hours prior to whole blood collection by heart puncture. Peripheral blood subsets were sorted based on FITC-Ly-6G (neutrophils), Cy5-CD19 (B cells), and Cy5-CD3 (T cells), and liposome fluorescence (Rhodamine B) was imaged via confocal microscopy. Hoechst 33342 staining was performed to identify cell nuclei. One of three representative experiments are shown.

To visualize liposome fluorescence in each of these cell subsets described in FIG. 8, cell subsets were also sorted and fixed onto glass slides for confocal analysis (FIG. 9). One of three representative experiments is shown.

Figure 10:
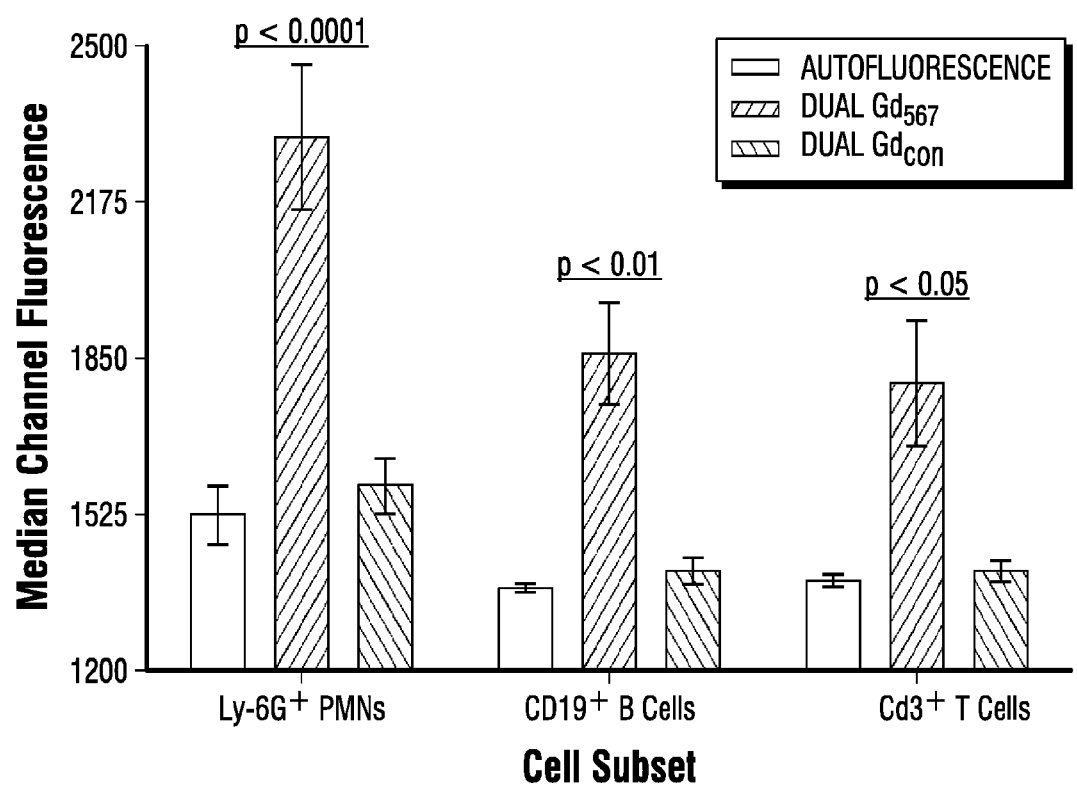
FIG. 10 illustrates quantitative assessment of enhanced THI567-targeted liposome accumulation in the aorta's of ApoE$^{-/-}$ mice fed a high fat diet three days after injection of liposome constructs. (A) Comparison of the normalized enhancement ratio (NER) of atherosclerotic plaques in non-targeted (n=7) and THI0567-targeted groups of mice (n=9). Data are presented as average±SEM. (B) Volume-rendered 3D image of a mouse aorta showing the different aortic segments examined. (C) Comparison of the NER in atherosclerotic plaques in non-targeted (n=7) and targeted groups of mice (n=6-8) for different segments of the aorta. Data are presented as average±SEM. (D, E) Representative sections of oil red staining (upper panels) and Rhodamine B fluorescence (lower panels) from the ascending aorta (D) and aortic arch (E) regions of untreated, THI0567-targeted liposomal-Gd, or non-targeted liposomal-Gd injected mice.
Figure 11A:
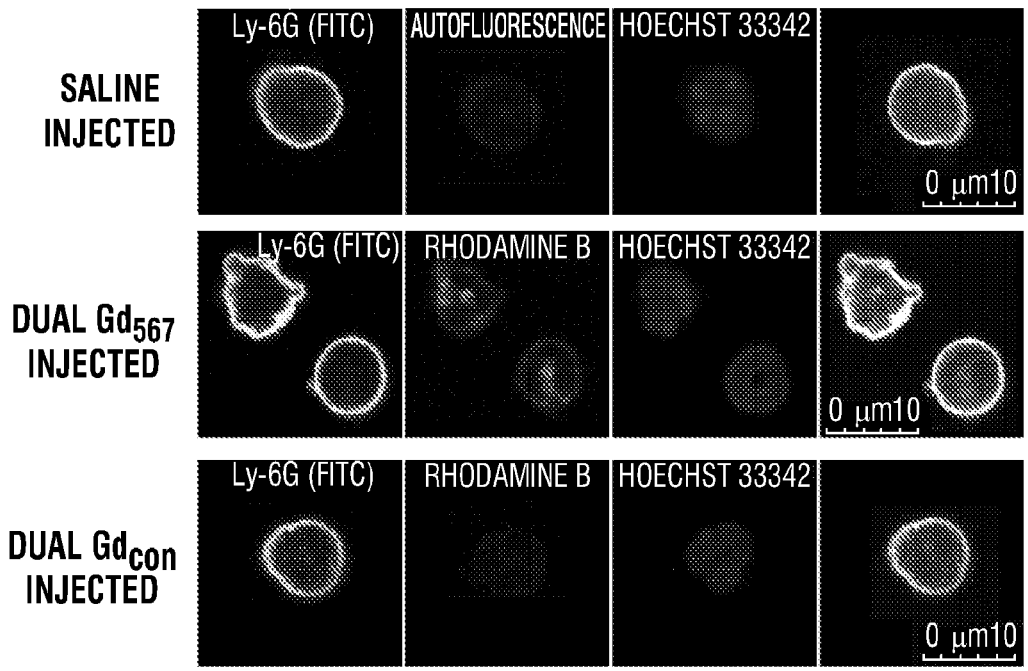
FIG. 11 illustrates THI0567-targeted liposome accumulation in atherosclerotic plaques of ApoE$^{-/-}$ mice. (A) Confocal fluorescence imaging of histological sections of the aortic root from mice injected with THI0567-targeted liposome (Rhodamine B fluorescence). Control IgG staining is represented in the low magnification (10x) image of the aortic root (upper left panel). Other representative sections were stained with anti-CD31 (upper right), anti-F4/80 (lower right), or anti-CD11b (lower left). Nuclei were stained with Hoechst 33342. (B) Partial section through the aortic arch, including the brachiocephalic artery, stained with anti-CD11b and Hoechst 33342. (C) Confocal fluorescence imaging of aortic arch sections of THI0567-targeted liposome treated animals (representative sections from n=8 animals. Fluorescence: THI0567-targeted liposome (Rhodamine B); CD11b (green); CD31 (purple); nuclei (Hoechst 33342; blue).
Figure 11B:
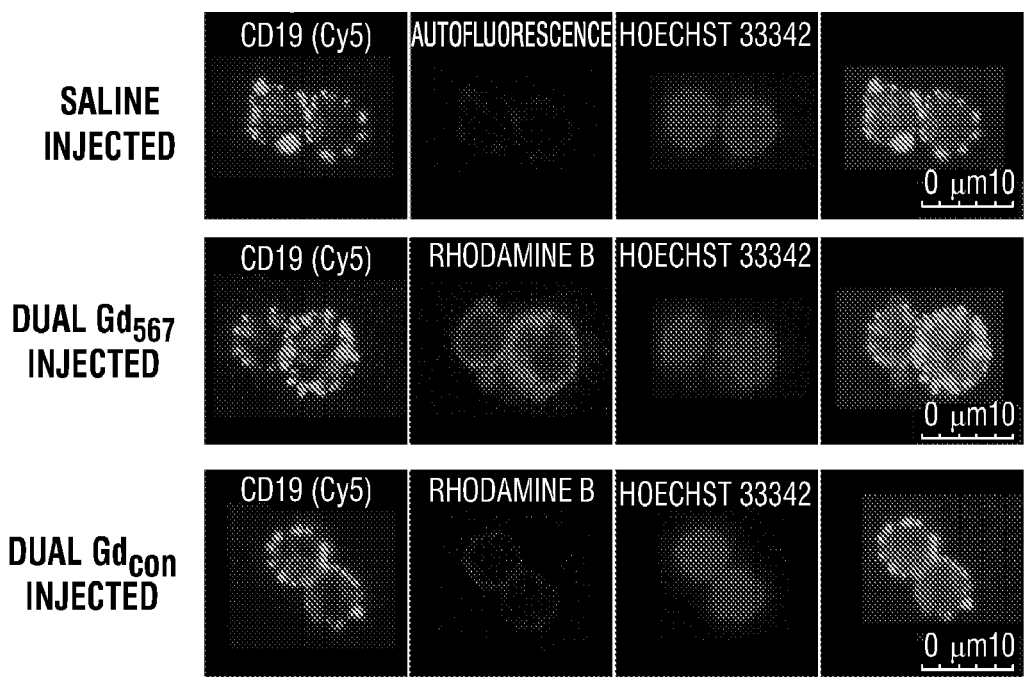
Figure 11C:
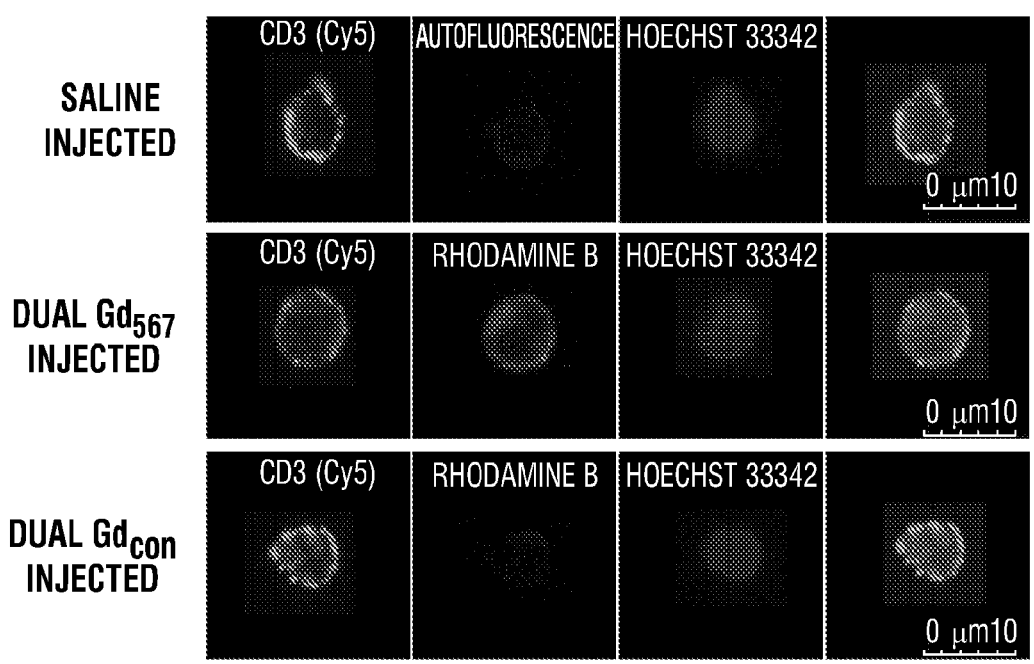
Figure 1:
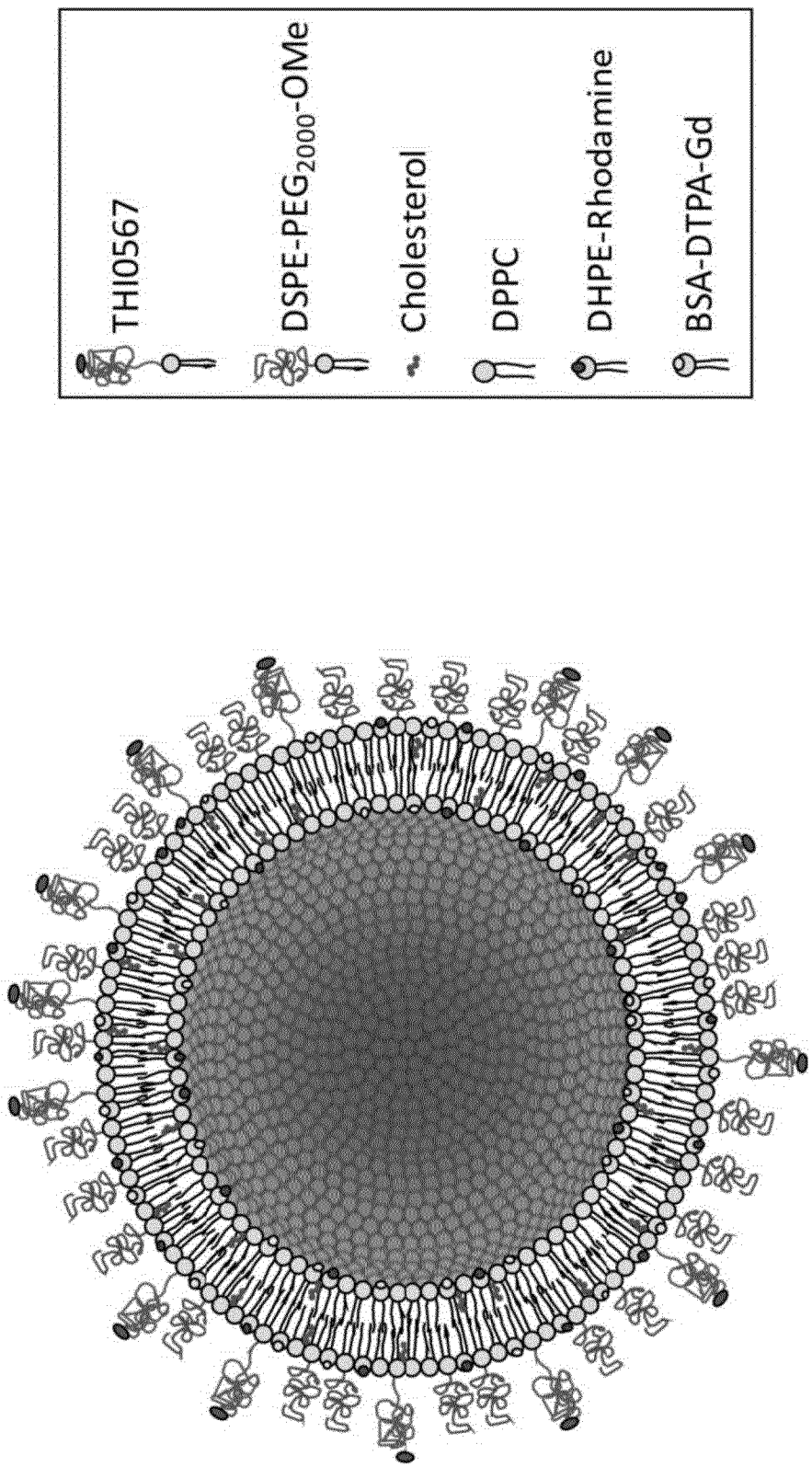

THI567-targetcd liposome uptake was quantified by MR imaging in atherosclerotic plaque in mice. For MRI studies, ApoE−/− mice (12-14 weeks old) were fed a high-fat diet for approximately 10 weeks. Then, the mice were intravenously injected with THI0567-targeted liposomes (0.1 mmol Gd/kg) or non-targeted control liposomes (0.1 mmol Gd/kg). In vivo MR imaging was performed on a 1T permanent magnet using a T1-weighted (T1w) 3D gradient-recalled echo (GRE) sequence. All mice underwent precontrast T1w imaging followed by administration of liposomal-Gd contrast agent (THI0567-targetcd or non-targeted) and an immediate postcontrast scan. To ensure clearance of the contrast agent from the circulation, we acquired delayed postcontrast scans 72 hours after administering the liposomal contrast. The THI0567-targeted liposomal-Gd agent showed significantly higher aortic wall signal enhancement on T1w images at multiple locations along the aorta (FIG. 10); the non-targeted agent did not show comparable signal enhancement. To quantitate signal enhancement in MR images, we calculated normalized enhancement ratios (NER). The overall NER was significantly higher in mice administered the THI0567-targeted liposomal-Gd agent than in those given the non-targeted liposomal-Gd (42.8±45.9 vs. 7.4±14.8, p=0.04) (FIG. 6A). To identify regions with the highest signal enhancement, we determined the NER in multiple aortic segments: the ascending aorta, aortic arch, and descending aorta (FIG. 10). The NER was significantly higher in targeted liposomal-Gd-treated mice than in mice administered non-targeted liposomal-Gd in the aortic arch (66.8±44.0 vs. 12.3±25.4, p=0.001) and the descending aorta (28.7±38.5 vs. −12.2±22.3, p=0.023) (FIG. 6C). In the ascending aorta, although the average NER was higher in the targeted-liposome group, the difference between the two groups did not reach statistical significance. After the delayed postcontrast scans, aortic tissue was harvested and sectioned to examine liposome accumulation patterns. On examination of sections from the ascending aorta and aortic arch, liposome accumulation (as indicated by Rhodamine B fluorescence) was limited to Oil red-positive plaques (FIG. 10). No Rhodamine B fluorescence was observed in plaques from untreated mice (FIG. 10).

Figure 11:
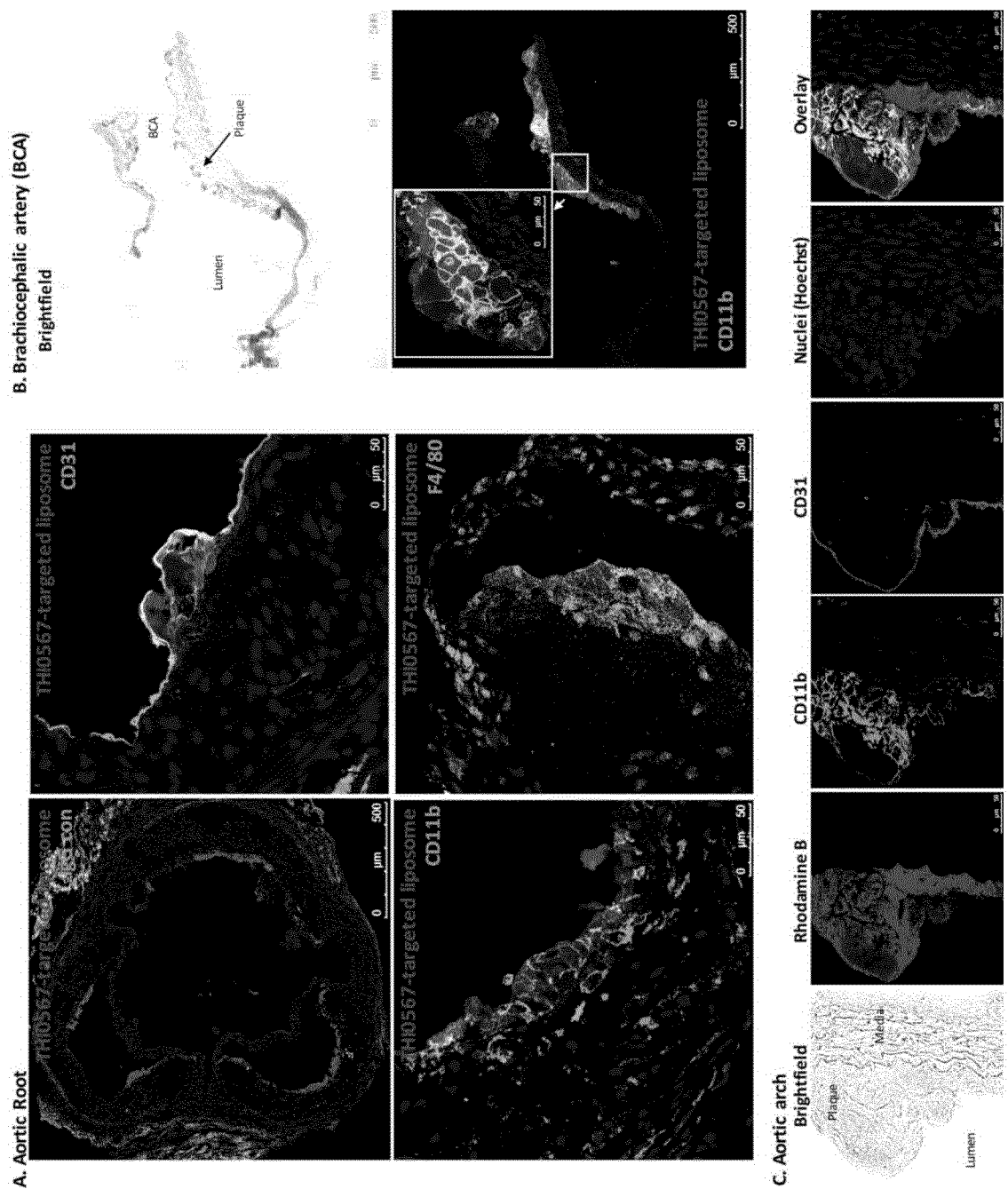

Sections of aortic plaques were examined by immunofluorescence to determine if markers associated with cells of the monocytic lineage colocalized with THI0567-targeted liposomes. Rhodamine B fluorescence (liposome) in the aortic root was limited to subendothelial areas within plaques (FIG. 11). Liposome fluorescence colocalized with both CD11b and F4/80 monocyte/macrophage markers (FIG. 11). Branching arteries, such as the brachiocephalic artery, and the aortic arch region contained dense THI0567-targeted liposome accumulation (FIG. 11), with liposomes internalized within CD11b+ cells in the plaque regions.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference in the Description of the Related Art is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

It should be noted that the term "about" may mean up to and including ±10% of the stated value. For example, "about 10" may mean from 9 to 11.

Furthermore, while the compositions, methods, and so on have been illustrated by describing examples, and while the examples have been described in considerable detail, it is not the intention of the applicant to restrict, or in any way, limit the scope of the appended claims to such detail. Thus, this application is intended to embrace alterations, modifications, and variations that fall within the scope of the appended claims. The preceding description is not meant to limit the scope of the invention. Rather, the scope of the invention is to be determined by the appended claims and their equivalents.

What is claimed is:

1. A compound or an integrin targeting agent, including optical isomers and pharmaceutically acceptable salts thereof, of the formula:

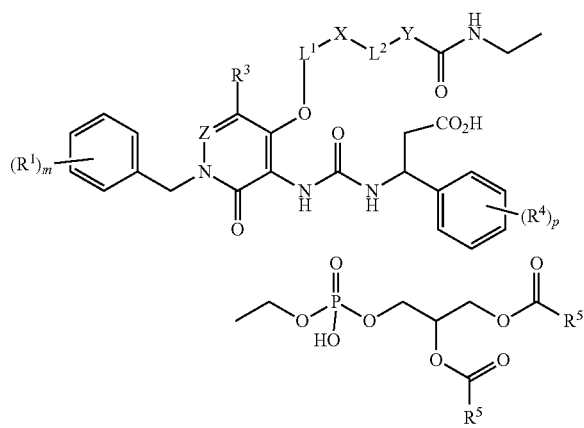

wherein,
R$^1$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N(C$_1$-C$_3$ alkyl)-C(O)(C$_1$-C$_3$ alkyl), —NHC(O)N(C$_1$-C$_3$ alkyl)C(O)NH(C$_1$-C$_3$ alkyl), —NHC(O)NH(C$_1$-C$_6$ alkyl), —NHSO$_2$(C$_1$-C$_3$ alkyl), —NHSO$_2$(aryl), —N(C$_1$-C$_3$ alkyl)SO$_2$(C$_1$-C$_3$ alkyl), —N(C$_1$-C$_3$ alkyl)SO$_2$(aryl), alkoxyalkyl, alkylamino, alkenylamino, di(C$_1$-C$_3$)amino, —C(O)O—(C$_1$-C$_3$)alkyl, —C(O)NH—(C$_1$-C$_3$)alkyl, —C(O)N(C$_1$-C$_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—(C$_1$-C$_3$ alkyl), —SO$_3$—(C$_1$-C$_3$ alkyl), sulfonamido, carbamate, aryloxyalkyl, OCF$_2$, OCH$_2$CF$_3$, aliphatic acyl, O(cycloalkylalkyl), O(aralkyl), —SO$_2$(1-pyrrolidinyl), SO$_2$(1-piperidinyl), piperidinyl, pyrrolidinyl, and —C(O)NH(benzyl) groups;

Z is N or CR$^2$;

R$^2$, when present, and R$^3$ are each independently selected from the group consisting of hydrogen, halogen, lower alkyl, lower alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N(C$_1$-C$_3$ alkyl)-C(O)(C$_1$-C$_3$ alkyl), —NHC(O)N(C$_1$-C$_3$ alkyl), —C(O)NH(C$_1$-C$_3$ alkyl), —NHC(O)NH(C$_1$-C$_6$ alkyl), —NHSO$_2$(C$_1$-C$_3$ alkyl), —NHSO$_2$(aryl), alkoxyalkyl, alkylamino, alkenylamino, di (C₁-C₃)amino, —C(O)O—(C₁-C₃) alkyl, —C(O)NH—(C₁-C₃)alkyl, —C(O)N(C₁-C₃ alkyl)₂, —CH=NOH, —PO₃H₂, —OPO₃H₂, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO₂—(C₁-C₃ alkyl), —SO₃(C₁-C₃ alkyl), sulfonamido, carbamate, aryloxyalkyl and —C(O)NH(benzyl) groups; and wherein R², when present, and R³ may be taken together to form a ring;

R⁴, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —CF₃, —CO₂H, —SH, —CN, —NO₂, —NH₂, —OH, alkynylamino, alkoxycarbonyl, heterocycloyl, carboxy, —N(C₁-C₃ alkyl)-C(O)(C₁-C₃ alkyl), —NHC(O)N(C₁-C₃ alkyl)C(O)NH(C₁-C₃ alkyl), —NHC(O)NH(C₁-C₆ alkyl), —NHSO₂(C1-C₃ alkyl), —NHSO₂(aryl), alkoxyalkyl, alkylamino, alkenylamino, di(C₁-C₃ alkyl)amino, —C(O)O—(C₁-C₃)alkyl, —C(O)NH—(C₁-C₃ alkyl), —C(O)N(C₁-C₃ alkyl)₂, —CH=NOH, —PO₃H₂, —OPO₃H₂, haloalkyl, alkoxyalkoxy, hydroxalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO₂—(C₁-C₃ alkyl), —SO₃—(C₁-C₃ alkyl), sulfonamido, carbamate, aryloxyalkyl, O(haloalkyl), O(cycloalkyl), O(cycloalkylalkyl), piperidinyl, pyrrolidinyl and —C(O)NH(benzyl) groups;

R¹, R², R³ and R⁴ are independently unsubstituted or substituted with at least one electron donating or electron withdrawing group;

R⁵ at each occurrence, is independently selected from a C₇-C₂₁ chain consisting of alkyl or alkenyl group;

m and p are independently at each occurrence an integer from 0 to 5;

L¹ is a chain of 3-14 atoms, containing any combination of —CH₂—, —C(O)—, —NH—, —S—, —S(O)—, —O—, —C(O)O— or —S(O)₂—;

X is selected from a group consisting of:

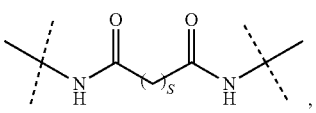

,

-continued

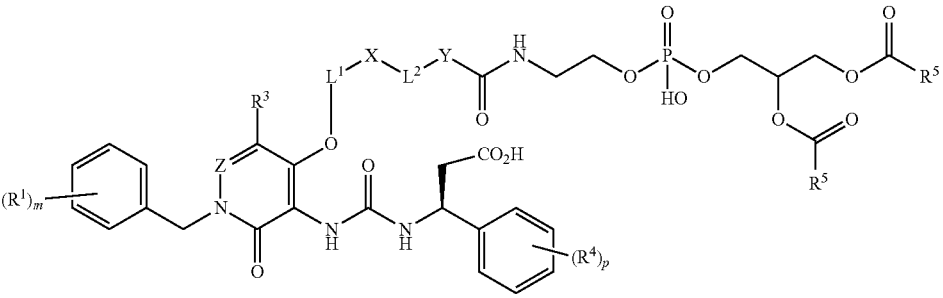

s is an integer from 1-2;

L² is a (CH₂CH₂O)ₙ— chain where n is an integer in the range of 7 to 115; and

Y is (CH₂)_q where q is an integer from 0 to 2; and wherein said compound has an average molecular weight of from 2000 to 7000.

2. The compound of claim 1 of the formula:

wherein,

R¹, at each occurrence, is independently selected from the group consisting of halogen, lower alkyl, alkoxy, thioalkoxy, hydroxyalkyl, —CF₃, —CN, —NO₂, —NH₂, —OH, —NHSO₂(C₁-C₃ alkyl), alkoxyalkyl, alkylamino, cycloalkyl, aralkyl, —SO₂(alkyl), —OCF₂, aliphatic acyl, —OCH₂CF₃, alkoxyalkoxy, —O(cycloalkylalkyl), —O(aralkyl), —SO₂(1-pyrrolidinyl), —SO₂(1-piperidinyl), piperidinyl, and pyrrolidinyl groups and wherein each R¹ is independently unsubstituted or substituted with at least one electron donating or electron withdrawing group;

Z is N or CR²;

R², when present, and R³ are each independently selected from the group consisting of hydrogen, halogen, and lower alkyl, groups; and wherein R², when present, and R³ may be taken together to form a ring and wherein each R², when present, and R³ are independently unsubstituted or substituted with at least one electron donating or electron withdrawing group;

R⁴, at each occurrence, is independently selected from the group consisting of halogen, lower alkyl, alkoxy, thioalkoxy, hydroxyalkyl, hydroxyalkoxy, —CF₃, —NH₂, —OH, —NHSO₂(C1-C₃ alkyl), —NHSO₂ (aryl), alkoxyalkyl, alkylamino, di(C₁-C₃ alkyl) amino, —C(O)O—(C₁-C₃)alkyl, —C(O)NH—(C₁-C₃ alkyl), —C(O)N(C₁-C₃ alkyl)₂, haloalkyl, alkoxyalkoxy, cycloalkyl, aryl, sulfonamido, O(haloalkyl), O(cycloalkyl), O(cycloalkylalkyl), piperidinyl, and pyrrolidinyl groups, wherein each R⁴ is independently unsubstituted or substituted with at least one electron donating or electron withdrawing group;

R⁵ at each occurrence, is independently selected from a C₇-C₂₁ chain consisting of alkyl or alkenyl group;

m and p are independently at each occurrence an integer from 0 to 5;

L¹ is a chain of 3-14 atoms, containing any combination of —CH₂—, —C(O)—, —NH—, —S—, —S(O)—, —O—, —C(O)O— or —S(O)₂—;

X is selected from a group consisting of:

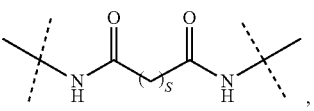

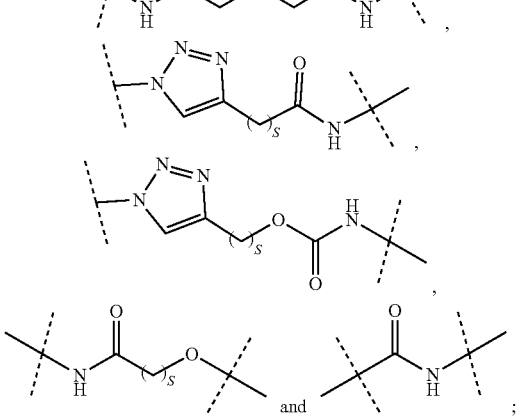

s is an integer from 1-2;

L² is a —(CH₂CH₂O)ₙ— chain where n is an integer in the range of 38 to 115; and

Y is (CH₂)q where q is an integer from 0 to 2.

3. The compound of claim 2, wherein each R⁵ is (CH₂)ᵣCH₃ wherein r is 10-20.

4. The compound of claim 3 of the formula:

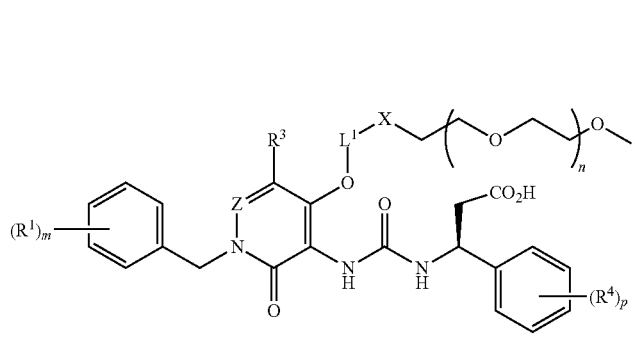

wherein n is an integer in the range of 38 to 115.

5. The compound of claim 4, wherein said L¹ is a 1,8-(3,6-dioxa)octan-di-yl radical, 1,5-(3-oxa)pentan-di-yl radical, or C₃-C₁₂ alkan-di-yl radical.

6. The compound of claim 5 of the formula:

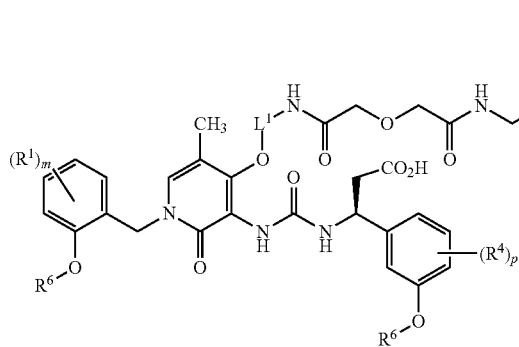
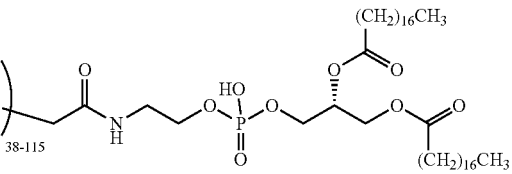

wherein each R⁶ is independently selected from the group consisting of hydrogen, lower alkyl and hydroxyalkyl;
wherein m and p are independently integers from 0-4.
7. The compound of claim 6 having a structure as follows:
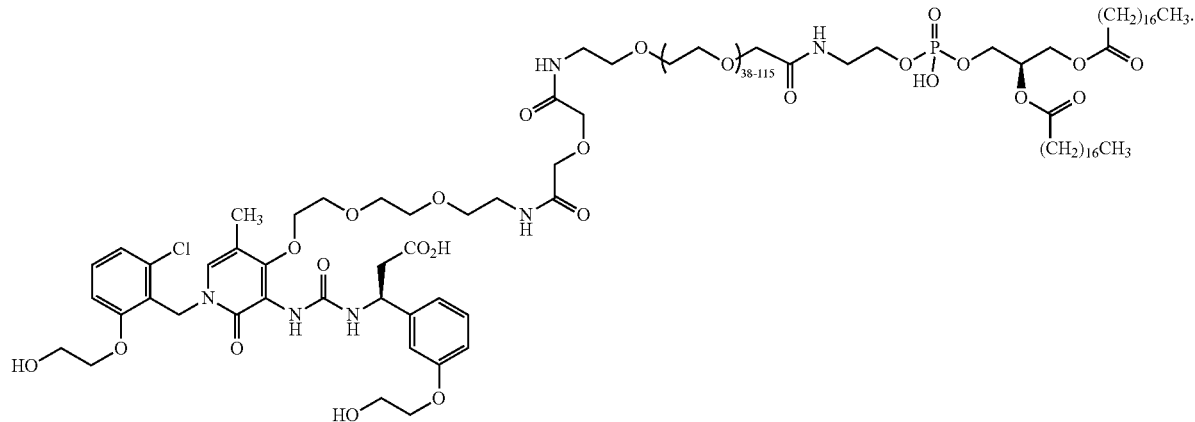
8. The compound of claim 6 having a structure as follows:
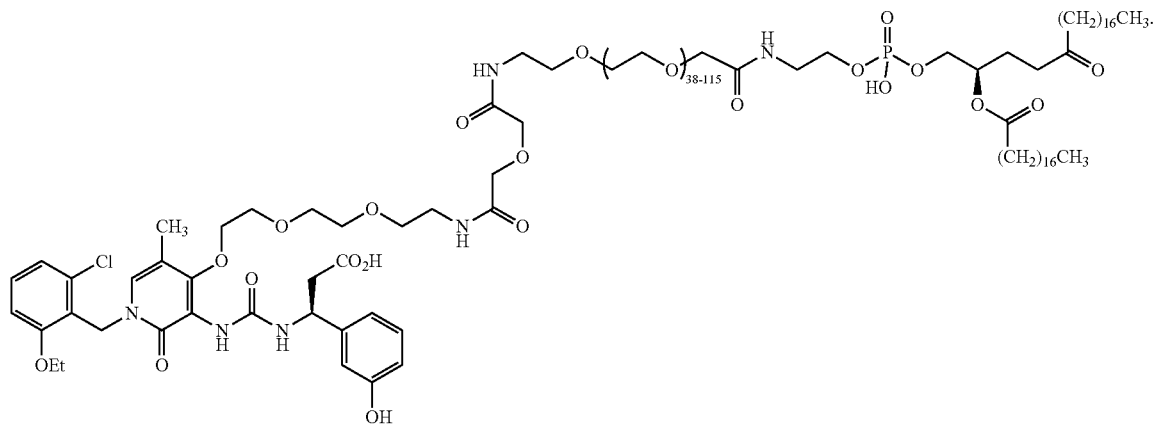
9. The compound of claim 6 of the formula:
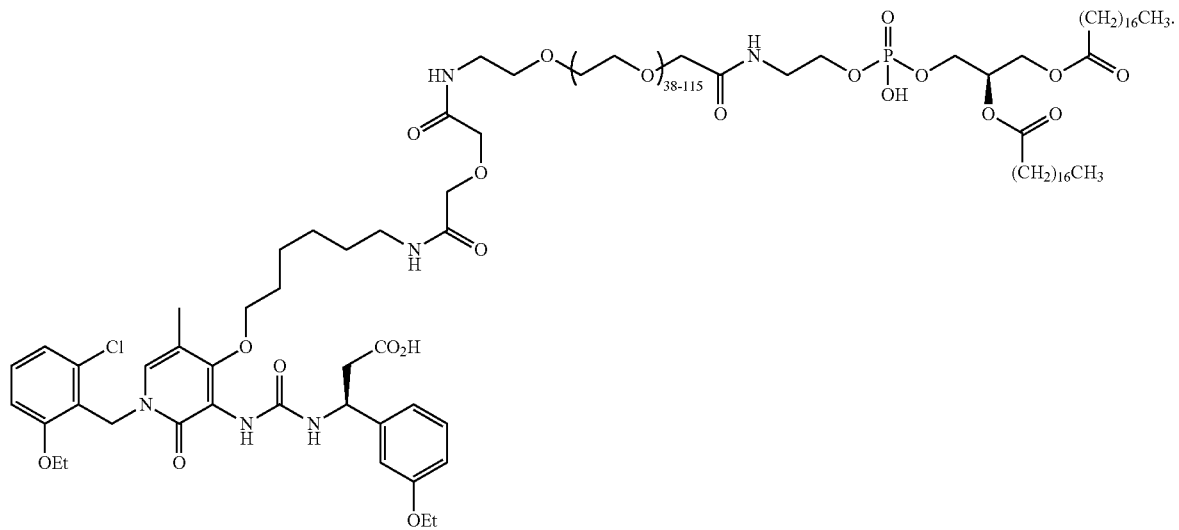

10. The compound of claim 1 enabling the generation of MRI images, optionally at 1 Tesla field strength.

11. A method of producing the compound or integrin targeting agent of claim 1, comprising:

forming a functionally protected VLA-4 antagonist of the structure, including optical isomers:

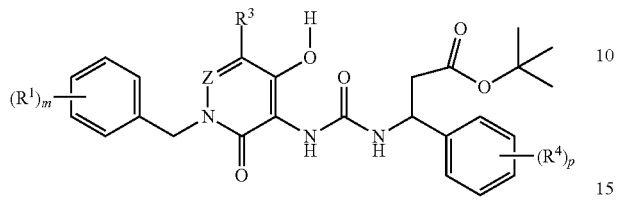

wherein,

R$^1$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N(C$_1$-C$_3$ alkyl)-C(O)(C$_1$-C$_3$ alkyl), —NHC(O)N(C$_1$-C$_3$ alkyl)C(O)NH(C$_1$-C$_3$ alkyl), —NHC(O)NH(C$_1$-C$_6$ alkyl), —NHSO$_2$(C$_1$-C$_3$ alkyl), —NHSO$_2$(aryl), —N(C$_1$-C$_3$ alkyl)SO$_2$(C$_1$-C$_3$ alkyl), —N(C$_1$-C$_3$ alkyl)SO$_2$(aryl), alkoxyalkyl, alkylamino, alkenylamino, di(C$_1$-C$_3$)amino, —C(O)O—(C$_1$-C$_3$)alkyl, —C(O)NH—(C$_1$-C$_3$)alkyl, —C(O)N(C$_1$-C$_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—(C$_1$-C$_3$ alkyl), —SO$_3$—(C$_1$-C$_3$ alkyl), sulfonamido, carbamate, aryloxyalkyl, OCF$_2$, OCH$_2$CF$_3$, aliphatic acyl, O(cycloalkylalkyl), O(aralkyl), —SO$_2$(1-pyrrolidinyl), SO$_2$(1-piperidinyl), piperidinyl, pyrrolidinyl, and —C(O)NH(benzyl) groups;

Z is N or CR$^2$;

R$^2$, when present, and R$^3$ are each independently selected from the group consisting of hydrogen, halogen, lower alkyl, lower alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N(C$_1$-C$_3$ alkyl)-C(O)(C$_1$-C$_3$ alkyl), —NHC(O)N(C$_1$-C$_3$ alkyl), —C(O)NH(C$_1$-C$_3$ alkyl), —NHC(O)NH(C$_1$-C6 alkyl), —NHSO$_2$(C$_1$-C$_3$ alkyl), —NHSO2(aryl), alkoxyalkyl, alkylamino, alkenylamino, di(C$_1$-C$_3$)amino, —C(O)O—(C$_1$-C$_3$)alkyl, —C(O)NH—(C$_1$-C$_3$)alkyl, —C(O)N(C$_1$-C$_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—(C$_1$-C$_3$ alkyl), —SO$_3$(C$_1$-C$_3$ alkyl), sulfonamido, carbamate, aryloxyalkyl and —C(O)NH(benzyl) groups; and wherein R$^2$, when present, and R$^3$ may be taken together to form a ring;

R$^4$, at each occurrence, is independently selected from the group consisting of halogen, lower alkyl, lower alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N(C$_1$-C$_3$ alkyl)-C(O)(C$_1$-C$_3$ alkyl), —NHC(O)N(C$_1$-C$_3$ alkyl)C(O)NH(C$_1$-C$_3$ alkyl), —NHC(O)NH(C$_1$-C$_6$ alkyl), —NHSO$_2$(C1-C$_3$ alkyl), —NHSO$_2$(aryl), alkoxyalkyl, alkylamino, alkenylamino, di(C$_1$-C$_3$ alkyl)amino, —C(O)O—(C$_1$-C$_3$)alkyl, —C(O)NH—(C$_1$-C$_3$ alkyl), —C(O)N(C$_1$-C$_3$ alkyl)$_2$, —CH=NOH, —PO$_3$H$_2$, —OPO$_3$H$_2$, haloalkyl, alkoxyalkoxy, hydroxalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—(C$_1$-C$_3$ alkyl), —SO$_3$—(C$_1$-C$_3$ alkyl), sulfonamido, carbamate, aryloxyalkyl, O(haloalkyl), O(cycloalkyl), O(cycloalkylalkyl), piperidinyl, pyrrolidinyl and —C(O)NH(benzyl) groups;

R$^1$, R$^2$, R$^3$ and R$^4$ are independently unsubstituted or substituted with at least one electron donating or electron withdrawing group;

m and p are independently at each occurrence an integer from 0 to 5;

the method further comprising:

synthesizing a phospholipid by alkylating at the pyridone hydroxyl with a functionalized 3-17 atom linking group;

optionally modifying the terminal functional group;

attaching to a polymeric group suitable for liposome formation by means of amide coupling, carbamate formation or triazole formation, and deprotection of functional groups; and producing an integrin targeting agent, including optical isomers and pharmaceutically acceptable salts thereof, of the formula:

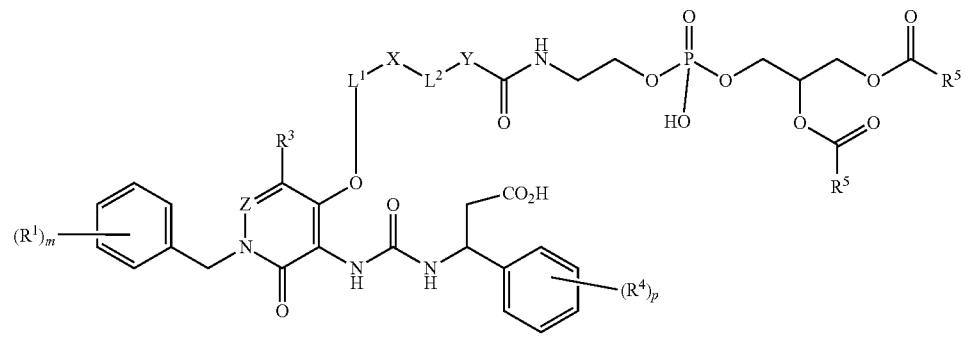

wherein,

R⁵ at each occurrence, is independently selected from a C₇-C₂₁ chain consisting of alkyl or alkenyl group;

L¹ is a chain of 3-14 atoms, containing any combination of —CH₂—, —C(O)—, —NH—, —S—, —S(O)—, —O—, —C(O)O— or —S(O)₂—;

X is selected from a group consisting of:

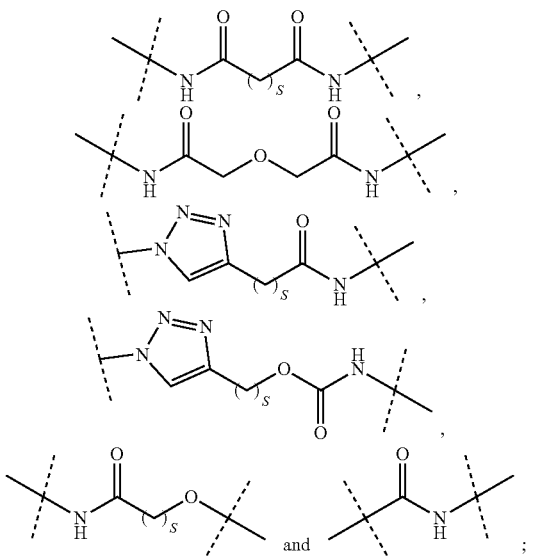

s is an integer from 1-2;

L² is a (CH₂CH₂O)ₙ— chain where n is an integer in the range of 7 to 115; and

Y is (CH₂)q where q is an integer from 0 to 2.

12. The method of claim 11 wherein said integrin targeting agent has an average molecular weight of 2000-7000.

13. The method of claim 11 wherein said integrin targeting agent enabling generation of MRI images, optionally at 1 Tesla field strength.

14. The method of claim 11 wherein said integrin targeting agent is incorporated into a delivery vehicle for drug delivery or diagnostics.

15. The method of claim 11 further comprising producing a liposome, wherein producing the liposome comprises:
combining a first lipid or phospholipid with a second lipid or phospholipid derivatized with a polymer, a sterically bulky excipient to stabilize the liposome, a third lipid or phospholipid derivatized with a polymer terminated with said integrin targeting agent, and optionally DSPE or a fourth lipid or phospholipid capable of binding a non-radioactive contrasting agent, and
extruding to form particles of less than 400 nm,
wherein said integrin targeting agent has a molecular weight of from 2000 to 7000.

16. The method of claim 15 wherein:

R¹ at each occurrence, is independently selected from the group consisting of halogen, lower alkyl, alkoxy, thioalkoxy, hydroxyalkyl, —CF₃, —CN, —NO₂, —NH₂, —OH, —NHSO₂(C₁-C₃ alkyl), alkoxyalkyl, alkylamino, cycloalkyl, aralkyl, —SO₂(alkyl), —OCF₂, aliphatic acyl, —OCH₂CF₃, alkoxyalkoxy, —O(cycloalkylalkyl), —O(aralkyl), —SO₂(1-pyrrolidinyl), —SO₂(1-piperidinyl) piperidinyl, and pyrrolidinyl groups and wherein each R¹ is independently unsubstituted or substituted with at least one electron donating or electron withdrawing group;

R², when present, and R³ are each independently selected from the group consisting of hydrogen, halogen, and lower alkyl, groups;

R⁴, at each occurrence, is independently selected from the group consisting of halogen, lower alkyl, alkoxy, thioalkoxy, hydroxyalkyl, hydroxyalkoxy, —CF₃, —NH₂, —OH, —NHSO₂(C1-C₃ alkyl), —NHSO₂(aryl), alkoxyalkyl, alkylamino, di(C₁-C₃ alkyl)amino, —C(O)O-(C₁-C₃)alkyl, —C(O)NH-(C₁-C₃ alkyl), —C(O)N(C₁-C₃ alkyl)₂, haloalkyl, alkoxyalkoxy, cycloalkyl, aryl, sulfonamido, O(haloalkyl), O(cycloalkyl), O(cycloalkylalkyl), piperidinyl, and pyrrolidinyl groups, wherein each R⁴ is independently unsubstituted or substituted with at least one electron donating or electron withdrawing group; and L² is a —(CH₂CH₂O)ₙ— chain where n is an integer in the range of 38 to 115.

17. The method of claim 16, wherein each R⁵ is (CH₂)ᵣCH₃ wherein r is 10-20.

18. The method of claim 17, wherein the integrin targeting component is of the formula:

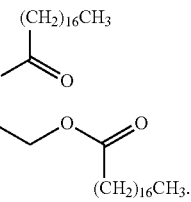

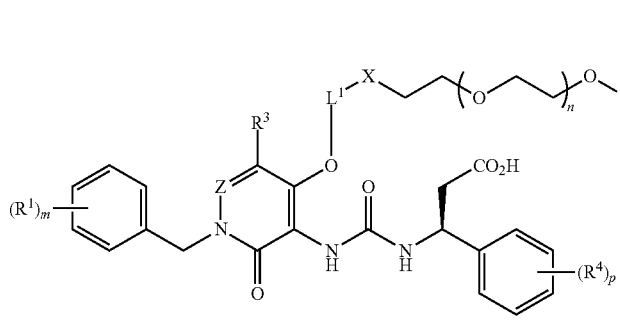

19. The method of claim 18, wherein said L¹ is a 1,8-(3,6-dioxa)octan-di-yl radical, 1,5-(3-oxa)pentan-di-yl radical, or C₃-C₁₂ alkan-di-yl radical.

20. The method of claim 19, wherein the integrin targeting component is of the formula:

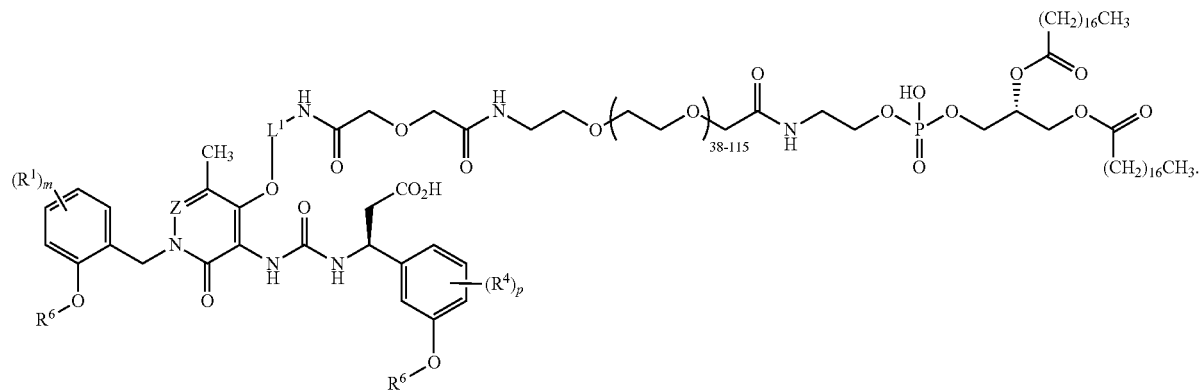
wherein each $R^6$ is independently selected from the group consisting of hydrogen, lower alkyl and hydroxyalkyl, wherein m and p are independently each an integer from 0-4.
21. The method of claim 20, wherein the integrin targeting component has a structure as follows:
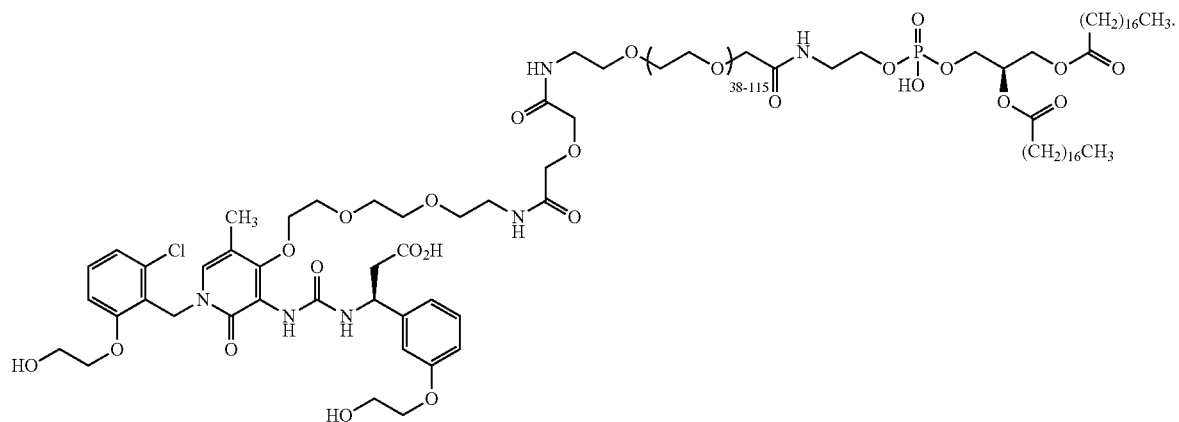
22. The method of claim 20, wherein the integrin targeting component has a structure as follows:
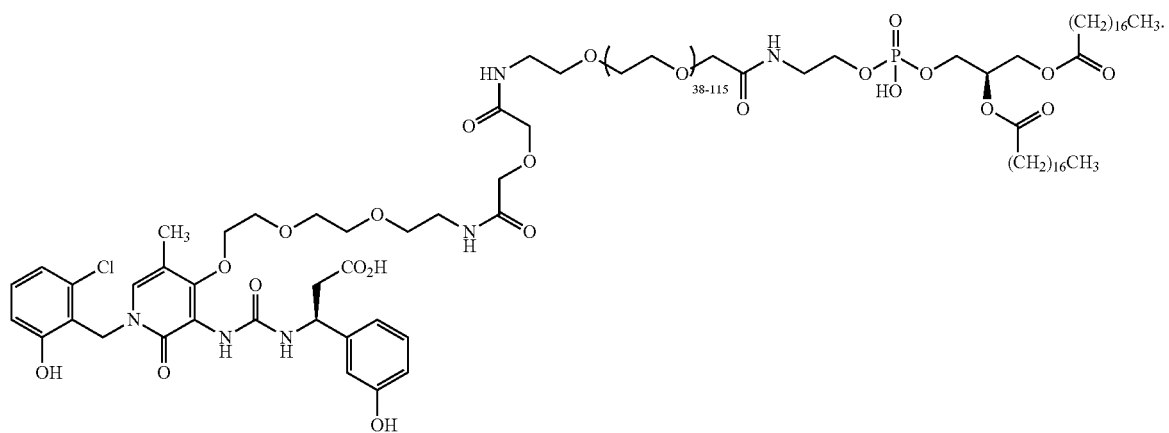

23. The method of claim 20, wherein the integrin targeting component is of the formula:

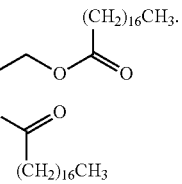
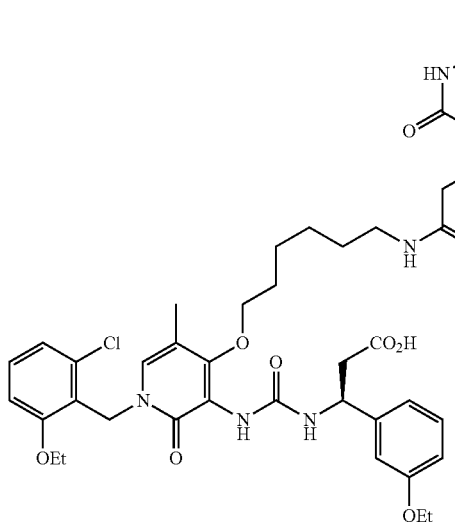

24. The method of claim 15 wherein said liposome enables generation of MRI images, optionally at 1 Tesla field strength.

25. A method of drug delivery using the compound or integrin targeting agent of claim 1, said method comprising:
forming a plurality of liposomes having an average diameter of less than 400 nanometers, said liposomes comprising:
a first lipid or phospholipid;
a second lipid or phospholipid which is derivatized with a polymer;
a sterically bulky excipient capable of stabilizing the liposomes;
a third lipid or phospholipid derivatized with a polymer terminated with an integrin targeting component, wherein said integrin targeting component has an average molecular weight of 2000-7000;
optionally DSPE;
encapsulating at least one bio-active agent using said plurality of liposomes; and administering said plurality of liposomes to a patient.

26. A method of imaging using the compound or integrin targeting agent of claim 1, said method comprising:
forming a plurality of liposomes having an average diameter of less than 400 nanometers, said liposomes comprising:
a first lipid or phospholipid;
a second lipid or phospholipid which is derivatized with a polymer;
a sterically bulky excipient capable of stabilizing the liposomes;
a third lipid or phospholipid derivatized with a polymer terminated with an integrin targeting component, wherein said integrin targeting component has an average molecular weight of 2000-7000;
a fourth lipid or phospholipid;
incorporating a contrast enhancing agent into said plurality of liposomes; and
using an imaging modality selected from the group consisting of CT, micro-CT, mammography, chest X-ray, MRI, magnetic resonance spectroscopy, bioluminescence imaging, ultrasound, optical imaging, optical spectroscopy, fluorescence spectroscopy, near-infrared spectroscopy, and near-infrared imaging.

27. A composition comprising the compound or integrin targeting agent of claim 1, said composition comprising a plurality of liposomes, said liposomes comprising:
a first lipid or phospholipid;
a second lipid or phospholipid which is derivatized with a polymer;
a sterically bulky excipient capable of stabilizing the liposomes;
a third lipid or phospholipid derivatized with a polymer terminated with an integrin targeting component; and
optionally DSPE or a fourth lipid or phospholipid derivatized with a group binding a nonradioactive contrast enhancing agent,
wherein the plurality of liposomes optionally encapsulates a payload component consisting of one or more bioactive agents, rhodamine, DHPE or iodine contrast agent;
wherein the plurality of liposomes have an average diameter of less than 400 nanometers,
wherein the first lipid or phospholipid, the second lipid or phospholipid which is derivatized with a polymer, and the sterically bulky excipient capable of stabilizing the liposomes, and the fourth lipid or phospholipid derivatized with a group binding a nonradioactive contrast enhancing agent are present in a molar ratio of about 30-32:3:40:25,
wherein the third lipid or phospholipid derivatized with a polymer terminated with an integrin targeting component consists of 0.05 to 2.0% (mole percent) the compound of claim 1.

28. The composition of claim 27, wherein the composition is usable in an imaging modality.

29. The composition of claim 28 wherein said imaging modality is selected from the group consisting of CT, micro-CT, mammography, X-ray, MRI, magnetic resonance spectroscopy, bioluminescence imaging, ultrasound, optical imaging, optical spectroscopy, fluorescence spectroscopy, fluorescence imaging, near-infrared spectroscopy, and near-infrared imaging.

30. The composition of claim 29 enabling generation of MRI images, optionally at 1 Tesla field strength.

31. A method of delivering a bio-active agent to a target cell in a patient, the method comprising administering the composition of claim 27 to the patient.

32. The method of claim 31, wherein the bio-active agent is selectively delivered to cells expressing α4β1 integrin.

33. The method of claim 32, wherein the cells expressing α4β1 integrin comprise one or more of the following types of cells: CD11b+ mononuclear cells, CD3+ T cells, CD19+ B cells, and Ly-6G+ polymorphonuclear leukocytes.

34. A method of imaging a biological structure in a subject, the method comprising administering to the subject the composition of claim 27 and detecting the contrast enhancing agent with an imager.

35. The method of claim 34, wherein liposomes in the composition become enriched in the biological structure.

36. The method of claim 34, wherein the imager performs one of the following techniques: CT, micro-CT, mammography, X-ray, MRI, magnetic resonance spectroscopy, bioluminescence imaging, ultrasound, optical imaging, optical spectroscopy, fluorescence spectroscopy, fluorescence imaging, near-infrared spectroscopy, and near-infrared imaging.

37. The method of claim 34, wherein the imager is an MRI scanner having a field strength of no more than 3T or of no more than 1T.

38. The method of claim 34, wherein the biological structure is an atherosclerotic plaque, a plurality of cells expressing α4β1 integrin, or a tumor.

39. A method of identifying a patient at risk for an acute ischemic event, the method comprising:
(a) administering to the subject the composition of claim 27;
(b) detecting the contrast enhancing agent with an MRI scanner to generate an image;
(c) evaluating the image for the presence of atherosclerotic plaques; and
(d) identifying the patient as being at risk for an acute ischemic event if atherosclerotic plaques are detected.

40. A composition comprising the compound or integrin targeting agent of claim 1, said composition comprising a plurality of liposomes,
wherein the plurality of liposomes comprise an integrin-targeting molecule,
wherein the integrin-targeting molecule comprises a polymer derivatized lipid or phospholipid moiety and an integrin-targeting moiety,
wherein the integrin-targeting moiety has one of the following structures:

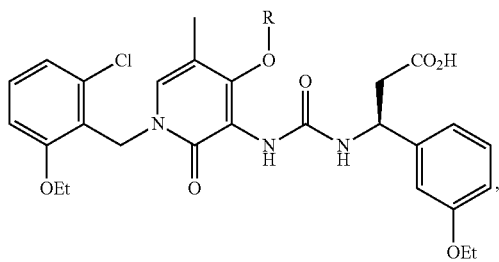

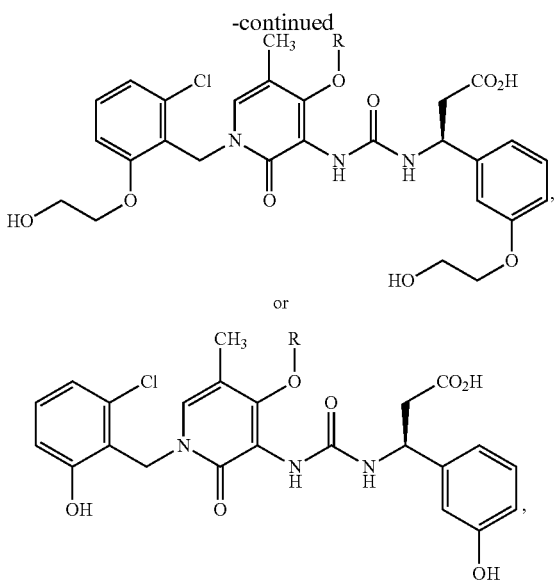

wherein R is the attachment point for the polymer derivatized lipid or phospholipid moiety.

41. The composition of claim 40, wherein the plurality of liposomes have an average diameter of 150 to 175 nm.

42. The composition of claim 40, wherein the integrin-targeting molecule comprises about 0.05 to 2 mol% of the plurality of liposomes.

43. The composition of claim 40, wherein the plurality of liposomes further comprise a bio-active agent.

44. The composition of claim 43, wherein the bio-active agent is encapsulated within the plurality of liposomes.

45. The composition of claim 40, wherein the plurality of liposomes further comprise a lipid or phospholipid derivatized with a group binding a contrast enhancing agent.

46. The composition of claim 45, wherein the lipid or phospholipid derivatized with a group binding a contrast enhancing agent comprises a DTPA-Gd or a DOTA-Gd moiety.

47. The composition of claim 40, wherein the liposomes comprise 30 to 45 mol% DPPC, 15 to 45 mol% cholesterol, 1 to 6 mol% DSPE-MPEG-2000, 20 to 30 mol% Gd-DOTA-DSPE, and 0.05 to 2 mol% THI-567.

48. A method of delivering a bio-active agent to a target cell in a patient, the method comprising administering the composition of claim 43 to the patient.

49. The method of claim 48, wherein the bio-active agent is selectively delivered to cells expressing α4β1 integrin.

50. The method of claim 49, wherein the cells expressing α4β1 integrin comprise one or more of the following types of cells: CD11b+ mononuclear cells, CD3+ T cells, CD19+ B cells, and Ly-6G+ polymorphonuclear leukocytes.

51. A method of imaging a biological structure in a subject, the method comprising administering to the subject the composition of claim 45 and detecting the contrast enhancing agent with an imager.

52. The method of claim 51, wherein liposomes in the composition become enriched in the biological structure.

53. The method of claim 51, wherein the imager performs one of the following techniques: CT, micro-CT, mammography, X-ray, MRI, magnetic resonance spectroscopy, bioluminescence imaging, ultrasound, optical imaging, optical spectroscopy, fluorescence spectroscopy, fluorescence imaging, near-infrared spectroscopy, and near-infrared imaging.

54. The method of claim 51, wherein the imager is an MRI scanner having a field strength of no more than 3T or of no more than 1T.

55. The method of claim 51, wherein the biological structure is an atherosclerotic plaque, a plurality of cells expressing α4β1 integrin, or a tumor.

56. A method of identifying a patient at risk for an acute ischemic event, the method comprising:
   (a) administering to the subject the composition of claim 45;
   (b) detecting the contrast enhancing agent with an MRI scanner to generate an image;
   (c) evaluating the image for the presence of atherosclerotic plaques; and
   (d) identifying the patient as being at risk for an acute ischemic event if atherosclerotic plaques are detected.

* * * * *

UNITED STATES PATENT AND TRADEMARK OFFICE
CERTIFICATE OF CORRECTION

| | | |
|---|---|---|
| PATENT NO. | : 11,312,685 B2 | |
| APPLICATION NO. | : 16/607554 | |
| DATED | : April 26, 2022 | |
| INVENTOR(S) | : Darren Woodside et al. | |

It is certified that error appears in the above-identified patent and that said Letters Patent is hereby corrected as shown below:

On the Title Page

Delete the title page and substitute therefore with the attached title page.

In the Drawings

Sheets 1-13 of the drawings should be replaced by the appended sheets.

In the Specification

In Column 57, Line 9, "FIG. 6A" should read --FIG. 10A--.

In Column 57, Line 16, "FIG. 6C" should read --FIG. 10C--.

Signed and Sealed this
Twenty-fifth Day of October, 2022

Katherine Kelly Vidal
*Director of the United States Patent and Trademark Office*

(12) United States Patent
Woodside et al.

(10) Patent No.: US 11,312,685 B2
(45) Date of Patent: Apr. 26, 2022

(54) TARGETING NANOPARTICLES

(71) Applicants: Texas Children's Hosptial, Houston, TX (US); Texas Heart Institute, Houston, TX (US)

(72) Inventors: Darren Woodside, Pearland, TX (US); Peter Vanderslice, Houston, TX (US); Robert Market, Houston, TX (US); Ronald Biediger, Houston, TX (US); Richard Dixon, Houston, TX (US); James T. Willerson, Houston, TX (US); Ananth Annapragada, Houston, TX (US); Eric Tanifum, Houston, TX (US)

(73) Assignees: Texas Heart Institute, Houston, TX (US); Texas Children's Hospital, Houston, TX (US)

(*) Notice: Subject to any disclaimer, the term of this patent is extended or adjusted under 35 U.S.C. 154(b) by 20 days.

(21) Appl. No.: 16/607,554

(22) PCT Filed: Apr. 27, 2018

(86) PCT No.: PCT/US2018/029991
§ 371 (c)(1),
(2) Date: Oct. 23, 2019

(87) PCT Pub. No.: WO2018/201069
PCT Pub. Date: Nov. 1, 2018

(65) Prior Publication Data
US 2021/0188774 A1 Jun. 24, 2021

Related U.S. Application Data

(60) Provisional application No. 62/491,349, filed on Apr. 28, 2017.

(51) Int. Cl.
C07D 213/69 (2006.01)
A61K 49/00 (2006.01)
A61K 49/10 (2006.01)
A61K 49/18 (2006.01)

(52) U.S. Cl.
CPC ........ C07D 213/69 (2013.01); A61K 49/0002 (2013.01); A61K 49/0084 (2013.01); A61K 49/106 (2013.01); A61K 49/1812 (2013.01)

(58) Field of Classification Search
CPC .. C07D 213/64; C07D 213/69; C07D 213/75; A61K 49/00
See application file for complete search history.

(56) References Cited

U.S. PATENT DOCUMENTS

| | | |
|---|---|---|
| 6,224,903 B1 | 5/2001 | Martin et al. |
| 6,972,296 B2 | 12/2005 | Biediger et al. |
| 2003/0082103 A1 | 5/2003 | Wartchow et al. |
| 2013/0079383 A1 | 3/2013 | Bennett et al. |

FOREIGN PATENT DOCUMENTS

WO 2000067746 A1 11/2000

OTHER PUBLICATIONS

Wissam Beaino et al., PET Imaging of very Late Antigen-4 in Melanoma: Comparison of 68Ga- and 64Cu-Labeled NODAGA and CB-TE1A1P-LLP2A Conjugates, J Nucl Med 55, 1856-1863. (Year: 2014).*
March, J., Advanced Organic Chemistry, Localized Chemical Bonding (1985), pp. 16-18.
Woodside, Darren, et al., Magnetic Resonance Imaging of Atherosclerotic Plaque at Clinically Relevant Field Strengths, Scientific Reports (2018) 8:3733.
Koley, D., et al., Chemoselective Nitration of Phenols with tert-Butyl Nitrite in Solution and on Solid Support, Organic Letters (2009), vol. 11, No. 18, pp. 4172-4175.
List, Benjamin, et al. Practical Synthesis—Unsaturated Esters From Aldehydes, Advanced Synthesis Catalysis (2005), vol. 347, pp. 1558-1560.
Ghaghada, Ketan B., et al. New Dual Mode Gadolinium Nanoparticle Contrast Agent for Magnetic Resonance Imaging. Yang S, editor. PLoS ONE. Oct. 29, 2009;4(10):e7628.
Beaino, W., and Anderson, C.J. (2014). PET imaging of very late antigen-4 in melanoma: comparison of 68Ga- and 64Cu-labeled NODAGA and CB-TE1A1P-LLP2A conjugates. J Nucl Med 55, 1856-1863.
Beaino, W., Nedrow, J.R., and Anderson, C.J. (2015). Evaluation of (68Ga- and (177)Lu-DOTA-PEG4-LLP2A for VLA-4-Targeted PET Imaging and Treatment of Metastatic Melanoma. Mol Pharm 12, 1929-1938.
Carpenter, R.D., Andrei, M., Lau, E.Y., Lightstone, F.C., Liu, R., Lam, K.S., and Kurth, M.J. (2007). Highly potent, water soluble benzimidazole antagonist for activated alpha 4 beta 1 integrin. J Med Chem 50, 5863-5867.
Carpenter, R.D., Natarajan, A., Lau, E.Y., Andrei, M., Solano, D.M., Lightstone, F.C., Denardo, S.J., Lam, K.S., and Kurth, M.J. (2010). Halogenated benzimidazole carboxamides target integrin alpha4beta1 on T-cell and B-cell lymphomas. Cancer Res 70, 5448-5456.
Denardo, S.J., Liu, R., Albrecht, H., Natarajan, A., Sutcliffe, J.L., Anderson, C., Peng, L., Ferdani, R., Cherry, S.R., and Lam, K.S. (2009). 111In-LLP2A-DOTA Polyethylene Glycol-Targeting {alpha}4{beta}1 Integrin: Comparative Pharmacokinetics for Imaging and Therapy of Lymphoid Malignancies. J Nucl Med 50, 625-634.

(Continued)

Primary Examiner — Michael G. Hartley
Assistant Examiner — Jagadishwar R Samala
(74) Attorney, Agent, or Firm — Jonathan Pierce; Pierre Campanac; Porter Hedges LLP

(57) ABSTRACT

Disclosed herein is a composition comprising a plurality of liposomes having an average diameter of less than 400 nanometers, wherein the plurality of liposomes comprise: a first lipid or phospholipid; a second lipid or phospholipid which is derivatized with a polymer; and a sterically bulky excipient capable of stabilizing the liposomes; a third lipid or phospholipid derivatized with a polymer terminated with an integrin targeting component; DSPE or a fourth lipid or phospholipid derivatized with a group binding a contrast enhancing agent wherein the plurality of liposomes optionally encapsulates a payload component consisting of one or more bioactive agents.

56 Claims, 11 Drawing Sheets